US006376503B1

(12) United States Patent
Patane et al.

(10) Patent No.: US 6,376,503 B1
(45) Date of Patent: Apr. 23, 2002

(54) ALPHA 1A ADRENERGIC RECEPTOR ANTAGONISTS

(75) Inventors: Michael A. Patane, Harleysville; Mark G. Bock, Hatfield; Randall C. Newton, West Point, all of PA (US); Bharat Lagu, Maywood, NJ (US)

(73) Assignees: Merck & Co., Inc, Rahway; Synaptic Pharmaceutical Corporation, Paramus, both of NJ (US)

( * ) Notice: Subject to any disclaimer, the term of this patent is extended or adjusted under 35 U.S.C. 154(b) by 0 days.

(21) Appl. No.: 09/097,947

(22) Filed: Jun. 17, 1998

Related U.S. Application Data

(60) Provisional application No. 60/050,959, filed on Jun. 18, 1997.

(51) Int. Cl.$^7$ .................. A61K 31/513; C07D 401/12
(52) U.S. Cl. .................. 514/274; 544/295; 544/296; 544/283; 544/284; 544/316; 514/252; 514/259; 514/253
(58) Field of Search ................... 514/274, 252, 514/259, 253; 544/295, 296, 283, 284, 316

(56) References Cited

U.S. PATENT DOCUMENTS

| | | | |
|---|---|---|---|
| 4,661,491 A | 4/1987 | Regnier | 514/260 |
| 4,769,371 A | 9/1988 | Atwal | 544/58.5 |
| 4,847,379 A | 7/1989 | Atwal | 544/316 |
| 4,855,301 A | 8/1989 | Atwal et al. | 514/269 |
| 5,202,330 A | 4/1993 | Atwal et al. | 514/274 |
| 5,574,044 A | 11/1996 | Thompson et al. | 514/316 |
| 5,618,827 A | 4/1997 | Oxford | 514/326 |

FOREIGN PATENT DOCUMENTS

| | | |
|---|---|---|
| EP | 0 234 830 | 9/1987 |
| EP | 0 236 902 | 9/1987 |
| FR | 1329617 | 5/1963 |
| WO | 92/00073 | 1/1992 |
| WO | 92/16213 | 10/1992 |
| WO | 94/08040 | 4/1994 |
| WO | 94/10989 | 5/1994 |
| WO | 94/22829 | 10/1994 |
| WO | 96/14846 | 5/1996 |
| WO | 97/17969 | 5/1997 |
| WO | 97/42956 | 11/1997 |

OTHER PUBLICATIONS

W. C. Wong et al., "Design and Synthesis of Dihydropyrimidines as Alpha 1a Adrenoceptor Selective Antagonists", Abstract No. MEDI 064, 215th ACS National Meeting, Dallas, TX (Mar. 29–Apr. 2, 1998).

B. Lagu et al., "Design, Synthesis and Evaluation of Dihydropyrimidinones as Alpha 1a Selective Antagonists", Abstract No., MEDI 065, 215th ACS National Meeting, Dallas, TX (Mar. 29–Apr. 2, 1998).

D. Nagarathnam et al., "Design, Synthesis and Evaluation of Dihydropyrimidinones as Alpha 1a Selective Antagonists: 6. Synthesis and Structure–Activity Relationship of SNAP 6553 and Analogs", Abstract No. MEDI 066, 215th ACS National Meeting, Dallas, TX (Mar. 29–Apr. 2, 1998).

M. R. Marzabadi et al, "Design, Synthesis and Evaluation of Dihydropyrimidinones and Dihydropyrimidines as Alpha 1a Selective Antagonists: Modification of the Diarylpiperidine Moiety", Abstract No. MEDI 067, 215th ACS National Meeting, Dallas, TX (Mar. 29–Apr. 2, 1998).

Derwent CPI Abstracts No. 90–041598, "Remedy for Dysuria", Abstract of JP01–319418, Nippon Chemifar (1990).

Derwent CPI Abstracts No. 87–027600, "New 1,3–oxazolidin–2–one derivatives", Abstract of JP61–286375, Nippon Chemifar (1987).

G. C. Rovnyak et al., "Dihydropyrimidine Calcium Channel Blockers. 4. Basic 3–Substitutued–4–aryl–1, 4–dihydropyrimidine–5–carboxylic Acid Esters. Potent Antihypertensive Agents", J. Med. Chem., 35 (17), 3254–63 (1992).

K. S. Atwal et al., "Dihydropyrimidine Calcium Channel Blockers. 3. 3–Carbamoyl–4–aryl–1,2,3, 4–tetrahydro–6–methyl–5–pyrimidinecarboxylic Acid Esters as Orally Effective Antihypertensive Agents", J. Med. Chem., 34(2), 806–11 (1991).

K. S. Atwal et al., "Dihydropyrimidine Calcium Channel Blockers. 2. 3–Substituted–4–aryl–1, 4–dihydro–6–methyl–5–pyrimidinecarboxylic Acid Esters as Potent Mimics of Dihydropyridines", J. Med. Chem., 33(9), 2629–35 (1990).

K. S. Atwal et al., "Substituted 1,4–Dihydropyrimidines. 3. Synthesis of Selectively Functionalized 2–Hetero–1,4–dihydropyrimidines", J. Org. Chem., 54(25), 5898–907 (1989).

*Primary Examiner*—John M. Ford
(74) *Attorney, Agent, or Firm*—Kenneth R. Walton; Melvin Winokur

(57) ABSTRACT

This invention relates to certain novel compounds and derivatives thereof, their synthesis, and their use as alpha 1a adrenergic receptor antagonists. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia are achieved.

17 Claims, No Drawings

ALPHA 1A ADRENERGIC RECEPTOR ANTAGONISTS

This application claims the benefit of U.S. Provisional Application No. 60/050,959, filed Jun. 18, 1997.

FIELD OF THE INVENTION

This invention relates to certain novel compounds and derivatives thereof, their synthesis, and their use as alpha 1a adrenoceptor antagonists. More particularly, the compounds of the present invention are useful for treating benign prostatic hyperplasia (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., *a-Adrenoreceptors: Molecular Biology, Biochemistry and Pharmacology*, (Progress in Basic and Clinical Pharmacology series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., Naunyn-Schmiedeberg's Arch. Pharmacol. (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5a-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-a reductase, which converts testosterone into 5a-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/0073, the selective ability of the R(+) enantiomer of terazosin to bind to adrenergic receptors of the alpha$_1$ subtype was reported. In addition, in WO 92/161213, combinations of 5a-reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The recent cloning of the human alpha 1a adrenergic receptor (ATCC CRL 11140) and the use of a screening assay utilizing the cloned human alpha 1a receptor enables identification of compounds which specifically interact with the human alpha 1a adrenergic receptor. [PCT International Application Publication Nos. WO94/08040, published Apr. 14, 1994 and WO94/10989, published May, 26, 1994] As disclosed in the instant patent disclosure, a cloned human alpha 1a adrenergic receptor and a method for identifying compounds which bind the human alpha 1a receptor has now made possible the identification of selective human alpha 1a adrenergic receptor antagonists useful for treating BPH. The instant patent disclosure discloses novel compounds which selectively bind to the human alpha 1a receptor. These compounds are further tested for binding to other human alpha 1 receptor subtypes, as well as counter-screened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

It has now been found that the compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides compounds for the treatment of urinary obstruction caused by benign prostatic hyperplasia (BPH). The compounds antagonize the human alpha 1a adrenergic receptor at nanomolar and subnanomolar concentrations while exhibiting at least ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc. The compounds of the present invention have the structure:

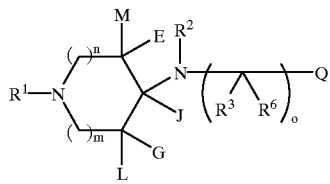

wherein Q is selected from

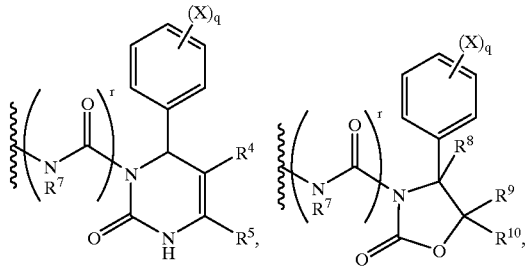

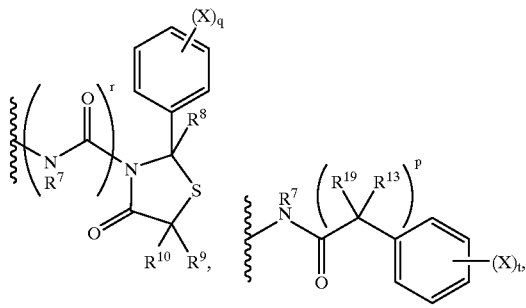

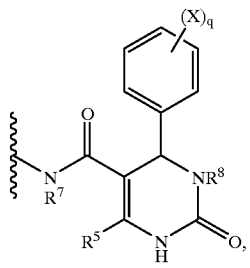

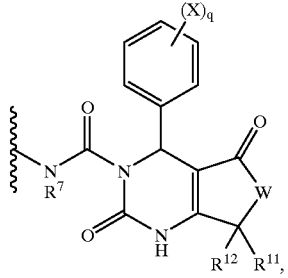

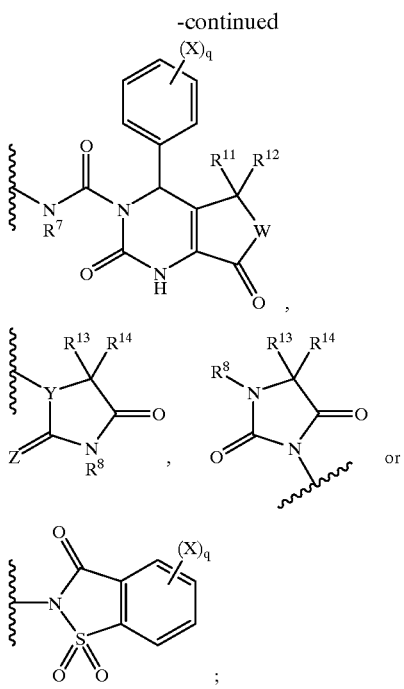

E, G, L and M are each independently selected from hydrogen, $C_{1-8}$ alkyl, $C_{3-8}$ cycloakl, $(CH_2)_{0-4}OR^{15}$, $(CH_2)_{0-4}N(R^{16})_2$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{16}$, or $(CH_2)_{0-4}SO_2N(R^{16})_2$;

J is selected from hydrogen, $C_{1-8}$ alkyl, $C_{3-8}$ cycloalkyl, $(CH_2)_{1-4}OR^{15}$, $(CH_2)_{1-4}N(R^{16})_2$, $(CH_2)_{1-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{16}$, or $(CH_2)_{0-4}SO_2N(R^{16})_2$;

$R^1$ is selected from unsubstituted, mono- or poly-substituted phenyl wherein the substituents on the phenyl are independently selected from halogen, $CF_3$, cyano, nitro, $N(R^{16})_2$, $NR^{16}COR^{18}$, $NR^{16}COR^{20}$, $NR^{16}CON(R^{18})_2$, $NR^{16}CONR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$ or $C_{1-4}$ alkyl; or unsubstituted, mono- or poly-substituted pyridyl, pyrazinyl, pyrimidinyl, thienyl, thiazolyl, furanyl, isoquinolinyl, quinazolinyl or naphthyl wherein the substituents on the pyridyl, pyrazinyl, pyrimidinyl, thienyl, thiazolyl, furanyl, isoquinolinyl, quinazolinyl or naphthyl are independently selected from $CF_3$, cyano, nitro, amino, $NR^{16}COR^{18}$, $NR^{16}COR^{20}$, $NR^{16}SO_2R^{18}$, $NR^{16}CONR^{16}CON(R^{18})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$, phenyl, $OR^{15}$, halogen, $C_{1-4}$ alkyl or $C_{3-8}$ cycloalkyl;

$R^2$ and $R^7$ are each independently selected from hydrogen, $C_{1-8}$ alkyl, $C_{4-8}$ cycloalkyl, $(CH_2)_{0-4}CO_2R^{16}$, $(CH_2)_{0-4}CON(R^{16})_2$, $(CH_2)_{0-4}COR^{16}$, $(CH_2)_{2-4}OR^{15}$, $(CH_2)_{1-4}CF_3$, $(CH_2)_{0-4}SO_2R^{16}$, $(CH_2)_{0-4}SO_2N(R^{16})_2$ or $(CH_2)_{1-4}CN$;

$R^3$, $R^6$, $R^9$ and $R^{10}$ are each independently selected from hydrogen, $C_{1-8}$ alkyl, $C_{3-8}$ cycloalkyl, $(CH_2)_{2-4}OR^{15}$ or $(CH_2)_{0-4}CF_3$;

$R^4$ is selected from hydrogen, $(CH_2)_{0-4}COR^{15}$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{15}$ or $(CH_2)_{0-4}SO_2N(R^{16})_2$;

$R^5$ is selected from hydrogen, $C_{1-8}$ alkyl, $C_{3-8}$ cycloalkyl, $(CH_2)_{1-4}OR^{15}$ or $(CH_2)_{0-4}CF_3$;

$R^8$ is selected from hydrogen, $C_{1-8}$ alkyl, $C_{3-8}$ cycloalkyl, $(CH_2)_{2-4}OR^{15}$ or $(CH_2)_{0-4}CF_3$;

$R^{11}$ and $R^{12}$ are each independently selected from hydrogen, $C_{1-8}$ alkyl or $C_{3-8}$ cycloalkyl;

$R^{13}$ and $R^{14}$ are each independently selected from hydrogen, $C_{1-8}$ alkyl, $C_{3-8}$ cycloalkyl, $(CH_2)_{1-4}OR^{15}$, $(CH_2)_{0-4}CF_3$, unsubstituted, mono- or poly-substituted phenyl wherein the substituents on the phenyl are independently selected from halogen, $CF_3$, cyano, nitro, $CO_2R^{16}$, $OR^{15}$, $(CH_2)_{0-4}CON(R^{16})_2$, $(CH_2)_{0-4}CO_2R^{16}$ or $C_{1-4}$ alkyl; or unsubstituted, mono- or poly-substituted: pyridyl, pyrazinyl, thienyl, furanyl or naphthyl wherein the substituents on the pyridyl, pyrazinyl, thienyl, furanyl or naphthyl are independently selected from $CF_3$, phenyl, $OR^{15}$, halogen, $C_{1-4}$ alkyl or $C_{3-8}$ cycloalkyl;

$R^{15}$ is selected from hydrogen, $C_{1-8}$ alkyl, $C_{3-8}$ cycloalkyl or $(CH_2)_{0-4}CF_3$;

$R^{16}$ and $R^{18}$ are each independently selected from hydrogen, $C_{1-8}$ alkyl, $C_{4-8}$ cycloalkyl or $(CH_2)_{1-4}CF_3$;

$R^{19}$ is selected from hydrogen, $C_{1-8}$ alkyl, $C_{3-8}$ cycloalkyl, $(CH_2)_{0-4}OR^{15}$ or $(CH_2)_{0-4}CF_3$;

$R^{20}$ is furanyl or $C_{1-8}$ alkyl furanyl;

$R^{22}$ is piperazinyl or $C_{1-8}$ alkylpiperazinyl;

W is O or $NR^{11}$;

each X is independently selected from halogen, cyano, nitro, $C_{1-8}$ alkyl, $C_{3-8}$ cycloalkyl, $(CH_2)_{0-4}OR^{15}$ or $(CH_2)_{0-4}CF_3$;

Y is $CR^{15}$ or N;

Z is hydrogen, oxygen or sulphur;

m, n, p and q are each independently an integer from zero to four;

o is an integer from two to five;

r is an integer from zero to one;

t is an integer from zero to five;

and the pharmaceutically acceptable salts thereof

In one aspect of the invention is the compound as just described with the proviso that: when $R^1$ is unsubstituted or mono-substituted phenyl; and $R^2$ is selected from hydrogen, $C_{1-8}$ alkyl, or $(CH_2)_{0-4}COR^{16}$; and $R^7$ is hydrogen; and M, E, J, G, L, $R^3$ and $R^6$ are each hydrogen; and n and m are each one; then Q is selected from

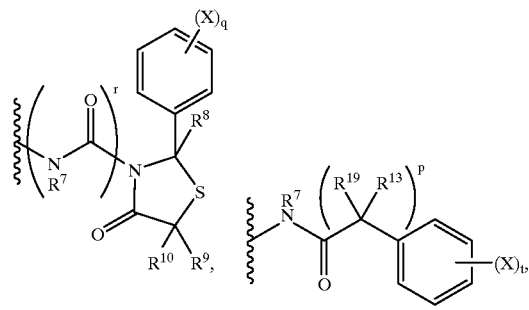

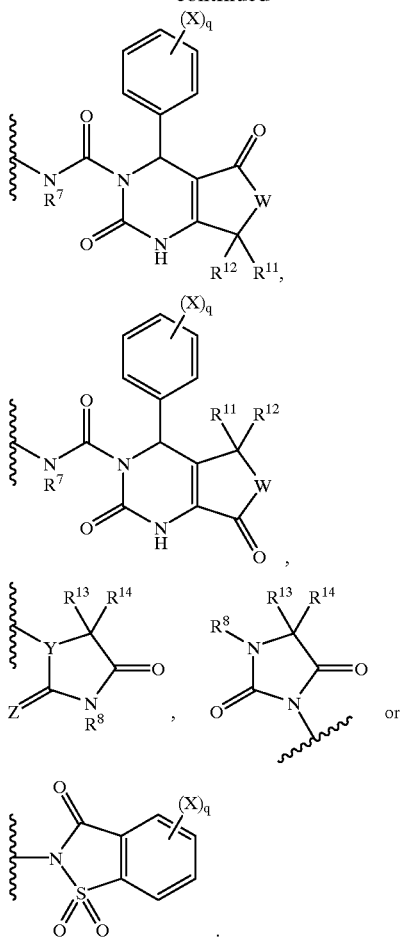

In a first embodiment of the invention are the compounds having the structure set forth above, wherein $R^1$ is selected from unsubstituted, mono- or poly-substituted phenyl wherein the substituents on the phenyl are independently selected from halogen, $CF_3$, cyano, nitro, $N(R^{16})_2$, $NR^{16}COR^{18}$, $NR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, furanyl, quinazolinyl or naphthyl are independently selected from $CF_3$, cyano, nitro, amino, $NR^{16}COR^{18}$, $NR^{16}SO_2R^{18}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl or $C_{3-8}$ cycloalkyl; and $R^4$ is selected from $(CH_2)_{0-4}COR^{15}$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{15}$ or $(CH_2)_{0-4}SO_2N(R^{16})_2$; and all other variables are as previously defined; and the pharmaceutically acceptable salts thereof. An aspect of the invention is the compound as just described in this embodiment with the proviso set forth in the preceding paragraph.

In a second embodiment of the invention is the compound of the formula

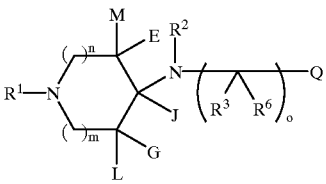

wherein

E, G, L, M and J are each independently selected from hydrogen, $C_{1-8}$ alkyl, $C_{3-8}$ cycloalkyl, or $(CH_2)_{0-4}CF_3$;

$R^1$ is selected from unsubstituted, mono-, di- or tri-substituted phenyl wherein the substituents on the phenyl are independently selected from halogen, $CF_3$, cyano, nitro, $N(R^{16})_2$, $NR^{16}COR^{18}$, $NR^{16}COR^{20}$, $NR^{16}CON(R^{18})_2$, $NR^{16}CONR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$ or $C_{1-4}$ alkyl; or unsubstituted, mono-, di- or tri-substituted pyridyl, pyrazinyl, pyrimidinyl, thienyl, thiazolyl, furanyl, isoquinolinyl, quinazolinyl or naphthyl wherein the substituents on the pyridyl, pyrazinyl, pyrimidinyl, thienyl, thiazolyl, furanyl, isoquinolinyl, quinazolinyl or naphthyl are independently selected from $CF_3$, cyano, nitro, amino, $NR^{16}COR^{18}$, $NR^{16}COR^{20}$, $NR^{16}SO_2R^{18}$, $NR^{16}CONR^{16}CON(R^{18})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$, phenyl, $OR^{15}$, halogen, $C_{1-4}$ alkyl or $C_{3-8}$ cycloalkyl;

$R^2$ and $R^7$ are each independently selected from hydrogen, $C_{1-8}$ alkyl, $C_{4-8}$ cycloalkyl or $(CH_2)_{1-4}CF_3$;

$R^{13}$ and $R^{14}$ are each independently selected from hydrogen, $C_{1-8}$ alkyl, $C_{3-8}$ cycloalkyl, $(CH_2)_{1-4}OR^{15}$, $(CH_2)_{0-4}CF_3$, unsubstituted, mono-, di- or tri-substituted phenyl wherein the substituents on the phenyl are independently selected from halogen, $CF_3$, cyano, nitro, amino, $OR^{15}$, $(CH_2)_{0-4}CON(R^{16})_2$, $(CH_2)_{0-4}CO_2R^{16}$ or $C_{1-4}$ alkyl; or unsubstituted, mono-, di- or tri-substituted: pyridyl, thienyl, furanyl or naphthyl wherein the substituents on the pyridyl, thienyl, furanyl or naphthyl are independently selected from $CF_3$, phenyl, $OR^{15}$, halogen, $C_{1-4}$ alkyl or $C_{3-8}$ cycloalkyl;

n is an integer from zero to two;

m is an integer from zero to one; and o is an integer from two to four;

and all other variables are as originally defined above; and the pharmaceutically acceptable salts thereof.

In a third embodiment of the invention is the compound of the formula

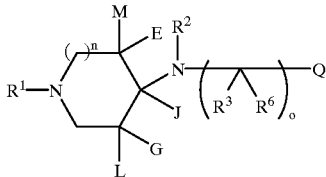

wherein E, G, L, M and J are each independently selected from hydrogen, $C_{1-8}$ alkyl, $C_{3-8}$ cycloalkyl, or $(CH_2)_{0-4}CF_3$;

$R^1$ is selected from unsubstituted, mono-, di- or tri-substituted phenyl wherein the substituents on the phenyl are independently selected from halogen, $CF_3$, cyano, nitro, $N(R^{16})_2$, $NR^{16}COR^{18}$, $NR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$ or $C_{1-4}$ alkyl; or unsubstituted, mono-, di- or tri-substituted pyridyl, pyrazinyl, thienyl, thiazolyl, furanyl, quinazolinyl or naphthyl wherein the substituents on the pyridyl, pyrazinyl, thienyl, thiazolyl, furanyl, quinazolinyl or naphthyl are independently selected from $CF_3$, cyano, nitro, amino, $NR^{16}COR^{18}$, $NR^{16}SO_2R^{18}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl or $C_{3-8}$ cycloalkyl;

$R^2$ and $R^7$ are each independently selected from hydrogen, $C_{1-8}$ alkyl, $C_{4-8}$ cycloalkyl or $(CH_2)_{1-4}CF_3$;

$R^{13}$ and $R^{14}$ are each independently selected from hydrogen, $C_{1-8}$ alkyl, $C_{3-8}$ cycloalkyl, $(CH_2)_{1-4}OR^{15}$, $(CH_2)_{0-4}CF_3$, unsubstituted, mono-, di- or tri-substituted phenyl wherein the substituents on the phenyl are independently selected from halogen, $CF_3$, cyano, nitro, amino, $OR^{15}$, $(CH_2)_{0-4}CON(R^{16})_2$, $(CH_2)_{0-4}CO_2R^{16}$ or $C_{1-4}$ alkyl; or unsubstituted, mono-, di- or tri-substituted: pyridyl, thienyl, furanyl or naphthyl wherein the substituents on the pyridyl, thienyl, furanyl or naphthyl are independently selected from $CF_3$, phenyl, $OR^{15}$, halogen, $C_{1-4}$ alkyl or ($C_{3-8}$ cycloalkyl;

n is an integer from zero to two;

o is an integer from two to four;

and all other variables are as defined in the first embodiment; and the pharmaceutically acceptable salts thereof.

In a first class of the invention is the compound of the formula selected from

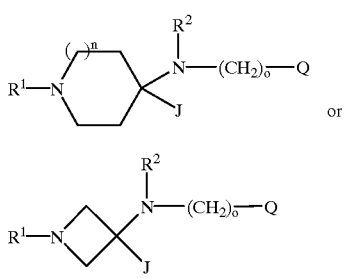

or

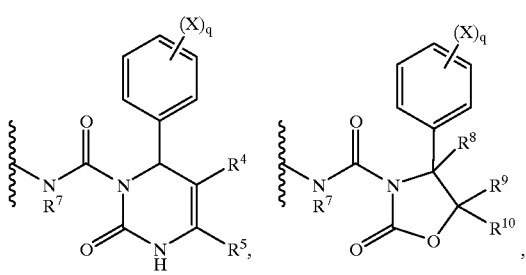

wherein Q is selected from

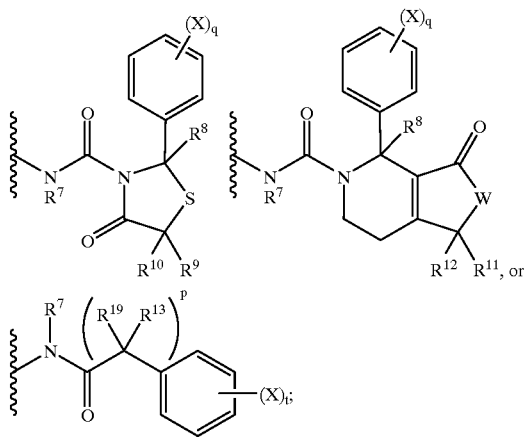

$R^1$ is selected from unsubstituted, mono-, di- or tri-substituted phenyl wherein the substituents on the phenyl are independently selected from halogen, $CF_3$, cyano, nitro, $N(R^{16})_2$, $NR^{16}COR^{18}$, $NR^{16}COR^{20}$, $NR^{16}CON(R^{18})_2$, $NR^{16}SO_2R^{18}$, $OR^{15}$, $(CH_2)_{0-2}CO_2R^{16}$, $(CH_2)_{0-2}CON(R^{16})_2$, $(CH_2)_{0-2}SO_2R^{15}$, $(CH_2)_{0-2}SO_2N(R^{16})_2$, $(CH_2)_{0-2}SO_2R^{22}$ or $C_{1-4}$ alkyl; or unsubstituted, mono- or di-substituted pyridyl or pyrimidinyl wherein the substituents on the pyridyl or the pyrimidinyl are independently selected from $CF_3$, cyano, nitro, amino, $NR^{16}COR^{18}$, $NR^{16}COR^{20}$, $NR^{16}CON(R^{18})_2$, $NR^{16}SO_2R^{18}$, $(CH_2)_{0-2}CO_2R^{16}$, $(CH_2)_{0-2}CON(R^{16})_2$, $(CH_2)_{0-2}SO_2R^{15}$, $(CH_2)_{0-2}SO_2N(R^{16})_2$, $OR^{15}$, halogen, $(CH_2)_{0-2}SO_2R^{22}$ or $C_{1-4}$ alkyl; or unsubstituted thiazolyl; or unsubstituted isoquinolinyl;

$R^2$ and $R^7$ are each independently selected from hydrogen, $C_{1-6}$ alkyl, $C_{4-6}$ cycloalkyl or $(CH_2)_{1-4}CF_3$;

$R^4$ is selected from hydrogen, $COR^{15}$, $(CH_2)_{0-2}CO_2R^{16}$, $SO_2R^{15}$ or $(CH_2)_{0-2}CON(R^{16})_2$;

$R^5$ is selected from hydrogen, $C_{1-6}$ alkyl, $C_{3-6}$ cycloalkyl, $(CH_2)_{1-3}OR^{15}$ or $(CH_2)_{0-3}CF_3$; and $R^8$, $R^9$ and $R^{10}$ are each independently selected from hydrogen, $C_{1-6}$ alkyl, $C_{3-6}$ cycloalkyl, $(CH_2)_{2-4}OR^{15}$ or $(CH_2)_{0-2}CF_3$;

$R^{13}$ is selected from hydrogen, $C_{1-6}$ alkyl, $C_{3-6}$ cycloalkyl, $(CH_2)_{2-4}OR^{15}$, $(CH_2)_{0-2}CF_3$ or unsubstituted, mono- or di-substituted phenyl wherein the substituents on the phenyl are independently selected from halogen, $CF_3$, cyano, nitro, amino, $OR^{15}$, $CO_2R^{16}$ or $C_{1-4}$ alkyl;

$R^{15}$ is selected from hydrogen, $C_{1-6}$ alkyl, $C_{3-6}$ cycloalkyl or $(CH_2)_{0-2}CF_3$;

$R^{16}$ and $R^{18}$ are each independently selected from hydrogen, $C_{1-6}$ alkyl, $C_{4-6}$ cycloalkyl or $(CH_2)_{1-2}CF_3$;

$R^{19}$ is selected from hydrogen, $C_{1-6}$ alkyl, $C_{3-6}$ cycloalkyl, $(CH_2)_{0-4}OR^{15}$ or $(CH_2)_{0-2}CF_3$;

is an integer from one to two;

q is an integer from zero to three;

t is an integer from zero to four;

and all other variables are as defined previously in the second embodiment;

and the pharmaceutically acceptable salts thereof.

In a second class of the invention is the compound of the formula

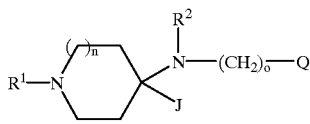

wherein Q is selected from

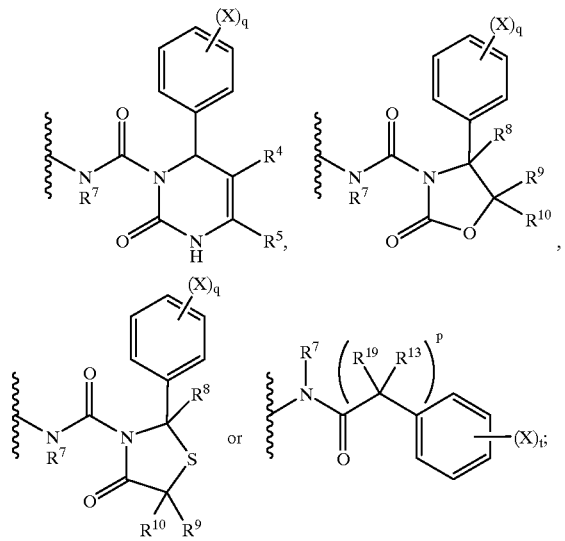

R[1] is selected from unsubstituted, mono-, di- or tri-substituted phenyl wherein the substituents on the phenyl are independently selected from halogen, $CF_3$, cyano, nitro, $N(R^{16})_2$, $NR^{16}COR^{18}$, $NR^{16}SO_2R^{18}$, $OR^{15}$, $(CH_2)_{0-2}CO_2R^{16}$, $(CH_2)_{0-2}CON(R^{16})_2$, $(CH_2)_{0-2}SO_2R^{15}$, $(CH_2)_{0-2}SO_2N(R^{16})_2$ or $C_{1-4}$ alkyl; or unsubstituted, mono- or di-substituted pyridyl wherein the substituents on the pyridyl are independently selected from $CF_3$, cyano, nitro, amino, $NR^{16}COR^{18}$, $NR^{16}SO_2R^{18}$, $(CH_2)_{0-2}CO_2R^{16}$, $(CH_2)_{0-2}CON(R^{16})_2$, $(CH_2)_{0-2}SO_2R^{15}$, $(CH_2)_{0-2}SO_2N(R^{16})_2$, $OR^{15}$, halogen or $C_{1-4}$ alkyl;

$R^2$ and $R^7$ are each independently selected from hydrogen, $C_{1-6}$ alkyl, $C_{4-6}$ cycloalkyl or $(CH_2)_{1-4}CF_3$;

$R^4$ is selected from $COR^{15}$, $(CH_2)_{0-2}CO_2R^{16}$, $SO_2R^{15}$ or $(CH_2)_{0-2}CON(R^{16})_2$;

$R^5$ is selected from hydrogen, $C_{1-6}$ alkyl, $C_{3-6}$ cycloalkyl, $(CH_2)_{1-3}OR^{15}$ or $(CH_2)_{0-3}CF_3$; and $R^8$, $R^9$ and $R^{10}$ are each independently selected from hydrogen, $C_{1-6}$ alkyl, $C_{3-6}$ cycloalkyl, $(CH_2)_{2-4}OR^{15}$ or $(CH_2)_{0-2}CF_3$;

$R^{13}$ is selected from hydrogen, $C_{1-6}$ alkyl, $C_{3-6}$ cycloalkyl, $(CH_2)_{2-4}OR^{15}$, $(CH_2)_{0-2}CF_3$ or unsubstituted, mono- or di-substituted phenyl wherein the substituents on the phenyl are independently selected from halogen, $CF_3$, cyano, nitro, amino, $OR^{15}$, $CO_2R^{16}$ or $C_{1-4}$ alkyl;

$R^{15}$ is selected from hydrogen, $C_{1-6}$ alkyl, $C_{3-6}$ cycloalkyl or $(CH_2)_{0-2}CF_3$;

$R^{16}$ and $R^{18}$ are each independently selected from hydrogen, $C_{1-6}$ alkyl, $C_{4-6}$ cycloalkyl or $(CH_2)_{1-2}CF_3$;

$R^{19}$ is selected from hydrogen, $C_{1-6}$ alkyl, $C_{3-6}$ cycloalkyl, $(CH_2)_{0-4}OR^{15}$ or $(CH_2)_{0-2}CF_3$;

p is an integer from one to two;

q is an integer from zero to three;

t is an integer from zero to four;

and all other variables are as defined previously in the third embodiment;

and the pharmaceutically acceptable salts thereof.

In a first subclass of the invention is the compound of the formula

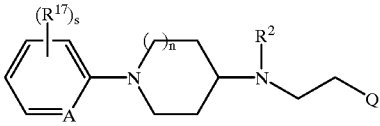

wherein Q is selected from

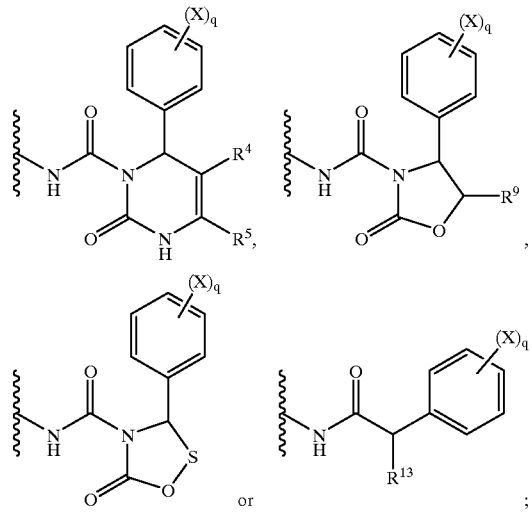

A is C—$R^{17}$ or N;

$R^2$ is selected from hydrogen or $CH_2CF_3$;

$R^9$ is selected from hydrogen or $C_{1-4}$ alkyl;

each $R^{17}$ is independently selected from hydrogen, halogen, $CF_3$, cyano, nitro, amino, $NR^{16}COR^{18}$, $NR^{16}CON(R^{18})_2$, $NR^{16}CONR^{16}CON(R^{18})_2$, $NR^{16}SO_2R^{18}$, $NR^{16}COR^{20}$, $OR^{15}$, $CO_2R^{16}$, $CON(R^{16})_2$, $SO_2N(R^{16})_2$, $SO_2R^{15}$ or $C_{1-4}$ alkyl;

each X is halogen;

n is an integer from zero to one; and q and s are each independently an integer from zero to two; and all other variables are as defined above in the first class; and the pharmaceutically acceptable salts thereof.

In a second subclass of the invention is the compound of the formula

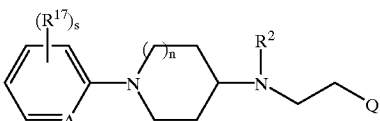

wherein Q is selected from

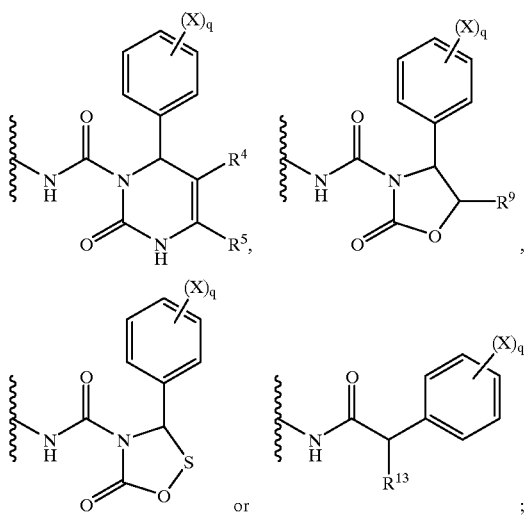

A is C—$R^{17}$ or N;

$R^2$ is selected from hydrogen or $CH_2CF_3$;

$R^9$ is selected from hydrogen or $C_{1-4}$ alkyl;

each $R^{17}$ is independently selected from hydrogen, halogen, $CF_3$, cyano, nitro, amino, $NR^{16}COR^{18}$, $NR^{16}SO_2R^{18}$, $OR^{15}$, $CO_2R^{16}$, $CON(R^{16})_2$, $SO_2N(R^{16})_2$, $SO_2R^{15}$ or $C_{1-4}$ alkyl;

each X is halogen;

n is an integer from zero to one; and q and s are each independently an integer from zero to two;

and all other variables as defined above in the second class;

and the pharmaceutically acceptable salts thereof.

In a first illustration of the invention is the compound of the formula

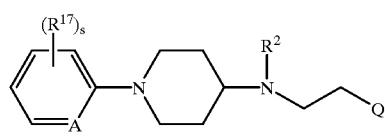

wherein Q is selected from

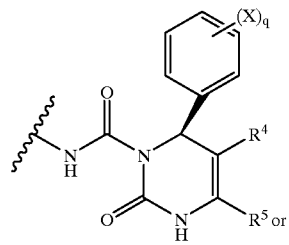

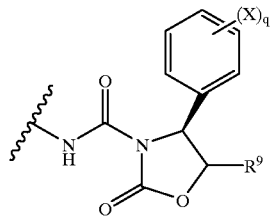

and all other variables are as defined above in the first subclass; and the pharmaceutically acceptable salts thereof.

In a second illustration of the invention is the compound of the formula

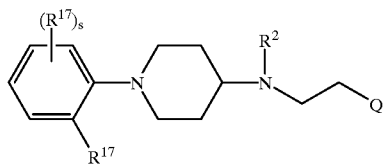

wherein Q is selected from

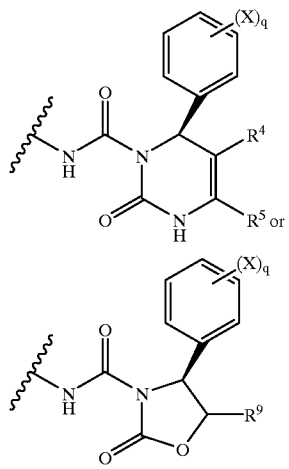

each $R^{17}$ is independently selected from hydrogen, halogen, $CF_3$, cyano, nitro, amino, $NHCONH_2$, $NHCONHCONH_2$, NHCO-furanyl, NHCONH $C_{1-4}$ alkyl, $C_{1-4}$ alkoxy, $OCF_3$, $OCH_2CF_3$, $CO_2$—$C_{1-4}$ alkyl, $CONH_2$, $SO_2NH_2$, $SO_2C_{1-4}$ alkyl, $NHSO_2C_{1-4}$ alkyl, $SO_2C_{1-4}$ alkylpiperazinyl or $C_{1-4}$ alkyl;, and all other variables are as defined above in the first subclass;

and the pharmaceutically acceptable salts thereof.

In a third illustration of the invention is the compound, of the formula

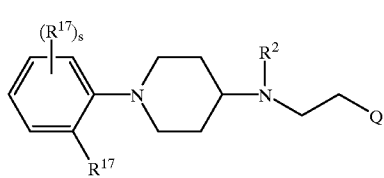

wherein Q is selected from

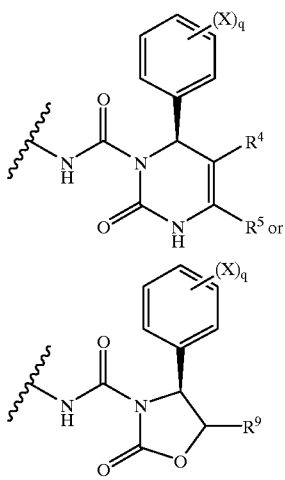

each $R^{17}$ is independently selected from hydrogen, halogen, $CF_3$, cyano, nitro, amino, $C_{1-4}$ alkoxy, $OCH_2CF_3$, $CO_2$—$C_{1-4}$ alkyl, $CONH_2$ or $C_{1-4}$ alkyl;
and all other variables are as defined above in the second subclass; and the pharmaceutically acceptable salts thereof.

Exemplifying the invention is the compound selected from

N-(2-(1-(2-cyanophenyl)piperidin-4-ylamino)ethyl)-2-(3,4-difluorophenyl)acetamide;
4-(3,4-difluorophenyl)-6-methoxymethyl-3-(2-(1-(2-nitrophenyl)-piperidin-4-ylamino)ethylcarbamoyl)-2-oxo-1,2,3,4-tetrahydropyrimidine-5-carboxylic acid methyl ester;
3-(2-(1-(2-cyanophenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;
4-(3,4-difluorophenyl)-6-methoxymethyl-2-oxo-3-(2-(1-o-tolylpiperidin-4-ylamino)ethylcarbamoyl)-1,2,3,4-tetrahydropyrimidine-5-carboxylic acid methyl ester;
4-(3,4-difluorophenyl)-2-oxo-oxazolidine-3-carboxylic acid (2-(1-(2-cyanophenyl)piperidin-4-ylamino)ethyl)amide;
4-(3,4-difluorophenyl)-6-methoxymethyl-3-(2-(1-(2-methoxyphenyl)piperidin-4-ylamino)ethylcarbamoyl)-2-oxo-1,2,3,4-tetrahydropyrimidine-5-carboxylic acid methyl ester;
3-(2-(1-(2-cyano-4-trifluoromethylphenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;
3-(2-(1-(2-cyano-4-methylphenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;
3-(2-(1-(4-cyanophenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;
3-(2-(1-(2-cyano-4-fluorophenyl)-piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;
4-(3,4-difluorophenyl)-3-(2-(1-(2-methoxycarbonylphenyl)piperidin-4-ylamino)ethylcarbamoyl)-6-methoxymethyl-2-oxo-1,2,3,4-tetrahydropyrimidine-5-carboxylic acid methyl ester;
4-(3,4-difluorophenyl)-2-oxo-oxazolidine-3-carboxylic acid (2-((1-(2-cyanophenyl)piperidin-4-yl)-(2,2,2-trifluoroethyl)amino)ethyl)amide;
4-(3,4-difluorophenyl)-6-methoxymethyl-2-oxo-3-(2-(1-(2-(2,2,2-trifluoroethoxy)phenyl)piperidin-4-ylamino)ethylcarbamoyl)-1,2,3,4-tetrahydropyrimidine-5-carboxylic acid methyl ester;
4-(3,4-difluorophenyl)-2-oxo-oxazolidine-3-carboxylic acid (2-(1-(2-(2,2,2-trifluoroethoxy)phenyl)piperidin-4-ylamino)ethyl)amide;
4-(3,4-difluorophenyl)-2-oxo-oxazolidine-3-carboxylic acid (2-(1-(2-cyanophenyl)pyrrolidin-3-ylamino)ethyl)amide;
2-(3,4-difluorophenyl)-N-(2-(1-(2-nitrophenyl)piperidin-4-ylamino)ethyl)acetamide;
N-(2-(1-(2-aminophenyl)piperidin-4-ylamino)ethyl)-2-(3,4-difluorophenyl)acetamide;
2-(3,4-difluorophenyl)-4-oxothiazolidine-3-carboxylic acid (2-(1-(2-cyanophenyl)piperidin-4-ylamino)ethyl)amide;
4-(3,4-difluorophenyl)5-methyl-2-oxo-oxazolidine-3-carboxylic acid (2-(1-(2-cyanophenyl) piperidin-4-ylamino)ethyl)amide;
3-(2-(1-(2-carbamoylphenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;
4-(3,4-difluorophenyl)-2-oxo-oxazolidine-3-carboxylic acid (2-(1-(2-carbamoylphenyl) piperidin-4-ylamino)ethyl) amide;
4-(3,4-difluorophenyl)-2-oxo-oxazolidine-3-carboxylic acid (2-(1-(4-fluoro-2-methoxycarbonylphenyl)piperidin-4-ylamino)ethyl)amide; or
4-(3,4-difluorophenyl)-2-oxo-oxazoidine-3-carboxylic acid (2-(1-(2-methoxycarbonylphenyl)piperidin-4-ylamino)ethyl)amide;

and the pharmaceutically acceptable salts thereof

Also exemplifying the invention is the compound selected from 4S-4-(3,4-difluorophenyl)-2-oxo-oxazolidine-3-carboxylic acid (2-(2-(3-trifluoromethylpyridyl)piperidin-4-ylamino)ethyl)amide;
4S-4-(3,4-difluorophenyl)-6-methoxymethyl-2-oxo-3-(2-(2-(3-trifluoromethylpyridyl)piperidin-4-ylamino)ethylcarbamoyl)-1,2,3,4-tetrahydropyrimidine-5-carboxylic acid methyl ester;
4S-4-(3,4-difluorophenyl)-6-methoxymethyl-2-oxo-3-(2-(2-(3-methylpyridyl)piperidin-4-ylamino)ethylcarbamoyl)-1,2,3,4-tetrahydropyrimidine-5-carboxylic acid methyl ester;
4S-4-(3,4-difluorophenyl)-6-methoxymethyl-2-oxo-3-(2-(2-(5-methylpyridyl)piperidin-4-ylamino)ethylcarbamoyl)-1,2,3,4-tetrahydropyrimidine-5-carboxylic acid methyl ester;
4S-4-(3,4-difluorophenyl)-6-methoxymethyl-2-oxo-3-(2-(2-(5-trifluoromethylpyridyl)piperidin-4-ylamino)ethylcarbamoyl)-1,2,3,4-tetrahydropyrimidine-5-carboxylic acid methyl ester;
4S-4-(3,4-difluorophenyl)-2-oxo-oxazolidine-3-carboxylic acid (2-(2-(5-trifluoromethylpyridyl)piperidin-4-ylamino)ethyl)amide;
4S-4-(3,4-difluorophenyl)-6-methoxymethyl-2-oxo-3-(2-(2-(4-trifluoromethylpyridyl)piperidin-4-ylamino)ethylcarbamoyl)-1,2,3,4-tetrahydropyrimidine-5-carboxylic acid methyl ester;
4S-4-(3,4-difluorophenyl)-2-oxo-oxazolidine-3-carboxylic acid (2-(2-(4-trifluoromethylpyridyl)piperidin-4-ylamino)ethyl)amide;

4S-4-(3,4-difluorophenyl)-6-methoxymethyl-2-oxo-3-(2-(2-(6-methylpyridinyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(6-bromopyridyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(3,6-bistrifluoromethylpyridyl)piperidyl-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(6-N-acetylaminopyridyl)piperidin-4-ylamino) ethylcarbamoyl)-1,2,3,4-tetrahydropyrimidine-5-carboxylic acid methyl ester;

and the pharmaceutically acceptable salts thereof.

Further exemplifying the invention is the compound selected from 4S-4-(3,4-difluorophenyl)-2-oxo-oxazolidine-3-carboxylic acid (2-(1-(2-methoxyphenyl)piperidin-4-ylamino)ethyl) amide;

4S-4-(3,4-difluorophenyl)-6-methoxymethyl-2-oxo-3-(2-(1-(2-trifluoromethylphenyl)piperid-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(4-methoxyphenyl)piperidin-4-ylamino) ethylcarbamoyl)-1,2,3,4-tetrahydropyrimidine-5-carboxylic acid methyl ester;

4S-4-(3,4-difluorophenyl)-2-oxo-oxazolidine-3-carboxylic acid (2-(1-(4-methoxyphenyl)piperidin-4-ylamino)ethyl) amide;

4S-4-(3,4-difluorophenyl)-2-oxo-oxazolidine-3-carboxylic acid (2-(2-(2,4-difluorophenyl)piperidin-4-ylamino) ethyl)amide;

4S-4-(3,4-difluorophenyl)-6-methoxymethyl-2-oxo-3-(2-(1-(2,4-difluorophenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-sulfonamidophenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-methanesulfonylphenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-trifluormethylphenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-cyanophenyl)pyrrolodin-3-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(phenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(3-fluorophenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(4-carboxylmethylphenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-cyano-5-fluorophenyl)piperidin-4-ylamino) ethylcarbamoyl)-1,2,3,4-tetrahydropyrimidine-5-carboxylic acid methyl ester;

4S-4-(3,4-difluorophenyl-6-methoxymethyl-2-oxo-3-(2-(1-(3,5-difluorophenyl)piperidin-4-ylamino) ethylcarbamoyl)-1,2,3,4-tetrahydropyrimidine-5-carboxylic acid methyl ester;

4S-4-(3,4-difluorophenyl)-2-oxo-oxazolidine-3-carboxylic acid (2-(1-(3,5-difluorophenyl)piperidin-4-ylamino) ethyl)amide;

4S-4-(3,4-difluorophenyl)-2-oxo-oxazolidine-3-carboxylic acid (2-(1-(2-carboxymethylphenyl)piperidin-4-ylamino) ethyl)amide;

4S-4-(3,4-difluorophenyl)-6-methoxymethyl-2-oxo-3-(2-(2-(3,6-bistrifluoromethylpyridyl)piperidin-4-ylamino) ethylcarbamoyl)-1,2,3,4-tetrahydropyrimidine-5-carboxylic acid methyl ester;

4S-4-(3,4-difluorophenyl)-2-oxo-oxazolidine-3-carboxylic acid (2-(1-(2-cyano-4-fluorophenyl)piperidin-4-ylamino) ethyl)amide;

4S-4-(3,4-difluorophenyl)-6-methoxymethyl-2-oxo-3-(2-(2-(3,5-dichlorophenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-N-sulfonylmethylaminophenyl)piperien-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-aminophenyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-nitrophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-N-carboxamidoaminophenyl)piperiden-4-ylamino) ethylcarbamoyl)-1,2,3,4-tetrahydropyrmidine-5-carboxylic acid methyl ester;

4S-4-(3,4-Difluorophenyl)-6methoxymethyl-2-oxo-3-(2-(2-(2-N-1-imidocarbonic diamidyl)phenyl)piperidin-4-ylamino)ethylcarbamoyl)-1,2,3,4-tetrahydropyrimidine-5-carboxylic acid methyl ester 4S-4-(3,4-difluorophenyl)-2-oxo-oxazolidine-3-carboxylic acid (2-(1-(2-nitrophenyl)piperidin-4-ylamino)ethyl) amide;

4S-4-(3,4-difluorophenyl)-6-methoxymethyl-2-oxo-3-(2-(2-(2-N-(2-furanyl)carbonylaminophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(4-N-methylpiperazinyl)sulfonylphenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-carboxymethylphenyl)piperidin-4-yl-1-methylamino)ethylcarbamoyl)-1,2,3,4-tetrahydropyrimidine-5-carboxylic acid methyl ester;

(4S)-4-(3,4-Difluorophenyl)-6-methoxymethyl-2-oxo-3-(2-(2-(1-N-(3-N-methylureyl)phenyl)piperidin-4-ylamino) ethylcarbamoyl)-1,2,3,4-tetrahydropyrimidine-5-carboxylic acid methyl ester;

and the pharmaceutically acceptable salts thereof.

An illustration of the invention is a pharmaceutical composition comprising a therapeutically effective amount of any of the compounds described above and a pharmaceutically acceptable carrier. An example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Another example of the invention is the composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

More specifically illustrating the invention is a method of treating benign prostatic hyperplasia in a subject in need thereof which comprises administering to the subject a therapeutically effective amount of any of the compounds (or any of the compositions) described above.

Further exemplifying the invention is the method of treating BPH wherein the compound (or composition) additionally does not cause a fall in blood pressure at dosages effective to alleviate BPH.

Another illustration of the invention is the method of treating benign prostatic hyperplasia wherein the compound is administered in combination with a testosterone 5-alpha reductase inhibitor. Preferably, the testosterone 5-alpha reductase inhibitor is finasteride.

Further illustrating the invention is a method of inhibiting contraction of prostate tissue or relaxing lower urinary tract tissue in a subject in need thereof which comprises administering to the subject a therapeutically effective amount of any of the compounds (or any of the compositions) described above.

More specifically exemplifying the invention is the method of inhibiting contraction of prostate tissue or relaxing lower urinary tract tissue wherein the compound (or composition) additionally does not cause a fall in blood pressures at dosages effective to inhibit contraction of prostate tissue.

More particularly illustrating the invention is the method of inhibiting contraction of prostate tissue or relaxing lower urinary tract tissue wherein the compound (or composition) is administered in combination with a testosterone 5-alpha reductase inhibitor; preferably, the testosterone 5-alpha reductase inhibitor is finasteride.

More particularly exemplifying the invention is a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see, K. A. Vatz, Headache 1997:37: 107–108) and cardiac arrhythmia.

An additional illustration of the invention is the use of any of the compounds described above in the preparation of a medicament for: a) the treatment of benign prostatic hyperplasia; b) relaxing lower urinary tract tissue; or c) inhibiting contraction of prostate tissue; in a subject in need thereof.

An additional example of the invention is the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

DETAILED DESCRIPTION OF THE INVENTION

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying at least ten-fold lower affinity for the human alpha1d and alpha1b adrenergic receptor subtypes, and many other G-protein coupled human receptors. Particular representative compounds of this invention exhibit nanomolar and subnanomolar affinity for the human alpha 1a adrenergic receptor subtype while displaying at least 30 fold lower affinity for the human alpha1d and alpha1b adrenergic receptor subtypes, and many other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed, as in BPH. For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Compounds of this invention are used to reduce the acute symptoms of BPH. Thus, compounds of this invention may be used alone or in conjunction with a more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound a vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "aryl" as used herein, except where otherwise specifically defined, refers to unsubstituted, mono- or poly-substituted aromatic groups such as phenyl or naphthyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "substituted" shall be deemed to include multiple degrees of substitution by a named substituent. The term "poly-substituted" as used herein shall include di-, tri-, tetra- and penta-substitution by a named substituent. Preferably, a poly-substituted moiety is di-, tri- or tetra-substituted by the named substituents, most preferably, di- or tri-substituted.

It is intended that the definition of any substituent or variable (e.g., X, $R^{16}$, $R^{18}$) at a particular location in a molecule be independent of its definitions elsewhere in that molecule. Thus, $-N(R^{16})2$ represents $-NH_2$, $-NHCH_3$, $-NHC_2H_5$, $-N(CH_3)C_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

Where multiple substituent moieties are disclosed or claimed, the substituted compound can be independently substituted by one or more of the disclosed or claimed substituent moieties, singly or plurally.

The term "Z is hydrogen," when refering to the "Q" group

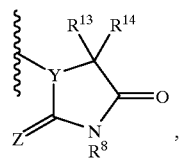

refers to the moiety

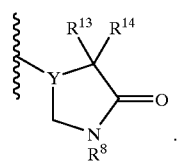

The term heterocycle or heterocyclic ring, as used herein, represents an unsubstituted or substituted stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The terms "(+)-DHP" and "DHP" as used herein, refers to a dihydropyrimidinone group of the formula

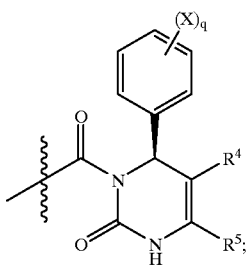

for example:

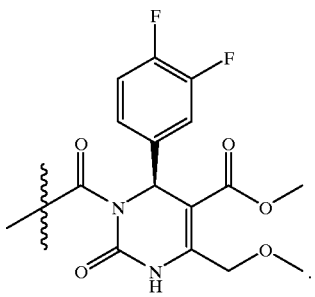

The term "activated (+)-DHP," as used herein, refers to a N-3-(activated)carbamate of the desired dihydropyrimidinone where the activating group is, for example, a p-nitrophenyloxy group. A specific example of an activated (+)DHP is 4-(3,4-difluorophenyl)-5-methoxycarbonyl-6-methoxymethyl-2-oxo-1,2,3,4-tetrahydropyrimidine-3-carboxylic acid (4-nitrophenyl ester), also referred to as the compound 2.

The term "(S)-oxa" as used herein, refers to an oxazolidinone group of the formula

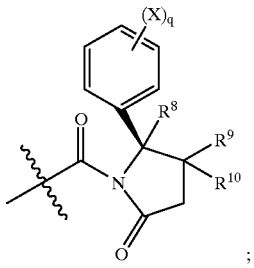

for example,

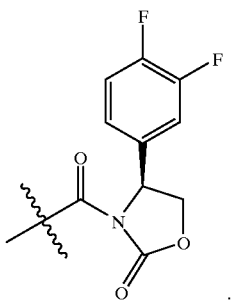

The term "activated (S)-oxa" as used herein, refers to an N-(activated)carbamate of the desired oxazolidinone where the activating group is, for example, a p-nitrophenyloxy group. A specific example of an activated (S)-oxa group is 4-(3,4-difluorophenyl)-2-oxo-oxazolidine-3-carboxylic acid 4-nitrophenyl ester (i.e., compound 3).

The term "thienyl," as used herein, refers to the group

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The specificity of binding of compounds showing affinity for the alpha 1a receptor is shown by comparing affinity to membranes obtained from tranfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g. PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7b-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. Nos. 4,377,584 and 4,760,071 which describe dosages and formulations for 5a-reductase inhibitors.

Abbreviations used in the instant specification, particularly the Schemes and Examples, are as follows:

Aq=aqueous
Ac=acetyl
AcOH=acetic acid
BCE=bromochloroethane
BINAP=2,2'-Bis(diphenylphosphino)-1,1'-binaphthyl
Boc or BOC=t-butyloxyearbonyl
BOPCl=bis(2-oxo-3-oxazolidinyl)phosphinic chloride
Cbz-Cl=benzyloxycarbonyl chloride
dba=dibenzylideneacetone
DEAD=diethylazodicarboxylate
DMF=N,N-dimethylformamide
DMSO=dimethylsulfoxide
EDCI=1-(3-dimethylaminopropyl)-3-ethylcarbodimide hydrochloride
Et=ethyl
$Et_3N$=triethylamine
EtOAc=ethyl acetate
EtOH=ethanol
FABLRMS=fast atom bombardment low resolution mass spectroscopy
HPLC=high performance liquid chromatography
HOAc=acetic acid
HOBt=1-hydroxy benzotriazole hydrate
i-PrOH=2-propanol
i-$Pr_2$NEt=diisopropylethylamine
LAH=lithium aluminum hydride
mCPBA=meta-chloroperbenzoic acid
Me=methyl
MeOH=methanol
NMR=nuclear magnetic resonance
PCTLC=preparative centrifugal thin layer chromatography
PEI=polyethylenimine
Ph=phenyl
pTOS=p-toluenesulfonic acid
RT=retention time
TEBAC=benzyltriethylammonium chloride
TFA=trifluoroacetic acid
THF=tetrahydrofuran
TLC=thin layer chromatography
TMS=trimethylsilyl The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Unless otherwise indicated, all variables are as defined above.

The preparation of key intermediates for the compounds of the present invention was accomplished via either Pd mediated coupling reactions or direct nucleophilic displacement, as outlined in Schemes 1 and 2. The products, typically ketals, were deketalized under acidic conditions. The resulting ketones can be further elaborated, for instance, via enolate alkylation. The resultant alpha substituted ketones were further elaborated by reductive amination with mono or unprotected diamino portions. After deprotection of the required intermediates, the selective acylation of the primary amines was accomplished by treatment with nearly equimolar quantities of the activated termini species (i.e., the "Q" groups).

The activated termini species comprising the "Q" groups are readily prepared by one of ordinary skill in the art. For example, oxazolidinones are prepared and activated in general by published and well developed chemistry, in particular, of Evans. [Evans, D. A.; Nelson, J. V.; Taber, T. R. Top. Stereochem. 13, 1 (1982)] The starting materials, in general, are natural and unnatural amino acids. For instance, some of the preferred compounds are prepared from substituted phenyl glycine derivatives, which after reduction of the carboxylate and a phosgene equivalent mediated cyclization provides the substituted oxazolidinone ring system. Deprotonation with n-butyl lithium and addition to a THF solution of p-nitrophenylchloroformate produces the stable, isolable "activated" oxazolidinone (oxa).

Dihydropyrimidinones are prepared by condensation reaction of the aldehyde, urea and a 1,3-acetoacetate type derivative catalyzed by a Lewis Acid, a copper (I) species and acetic acid. Activation was accomplished by treatment with a strong base, for instance, $LiN(TMS)_2$, followed by addition to a THF solution of p-nitrophenylchloroformate.

Hydantoins and cycloimide were prepared in two chemical steps from ketones as outlined in the literature. More specifically, hydantoins were prepared according to known methodology, e.g., J. J. Edmunds et al., J. Med. Chem. 1995, 38, pp. 3759–3771; J. H. Poupaert et al., J. Chem. Res. 1979, pp. 174–175. Saccharins were prepared according to known methods, e.g., page 40 and Examples 21 and 22 of PCT International Application Publication No. WO96/25934, published Aug. 29, 1996.

The dihydropyrimidinones and oxazolidinones were synthesized independently in racemic form, and then separated utilizing preparative chiral HPLC. Their optical rotations were recorded. Then they were activated and reacted with prerequisite amines. From the receptor binding studies, a preferred isomer was identified, the (+) rotational isomer in each case. The absolute configurations were determined to be (S) for both the dihydropyrimidinones and oxazolidinones by correlating their optical rotations with x-ray crystal structures obtained of fragments involved in the production of the antagonists.

SCHEME 1
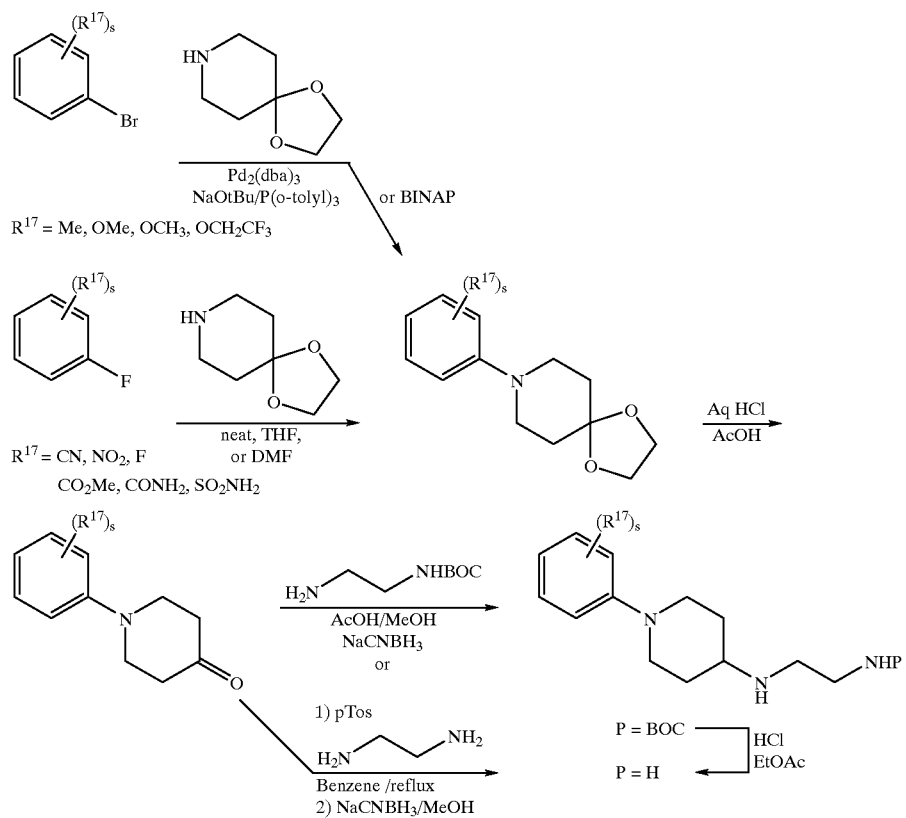

SCHEME 2
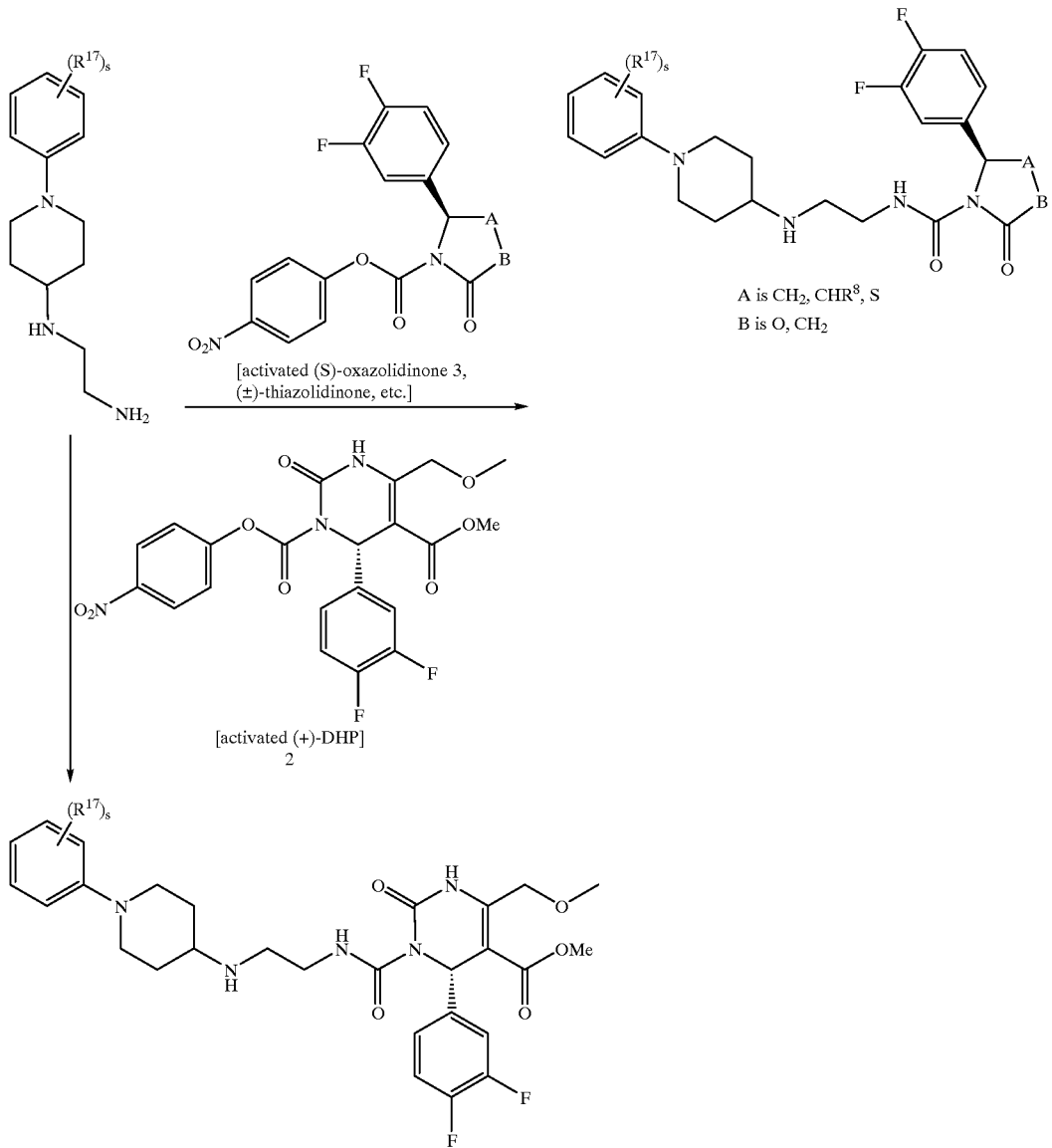
A is $CH_2$, $CHR^8$, S
B is O, $CH_2$
[activated (S)-oxazolidinone 3, (±)-thiazolidinone, etc.]
[activated (+)-DHP] 2
Similarly, heteroaryl variants are synthesized as shown in Schemes 3A and 3B.
SCHEME 3A
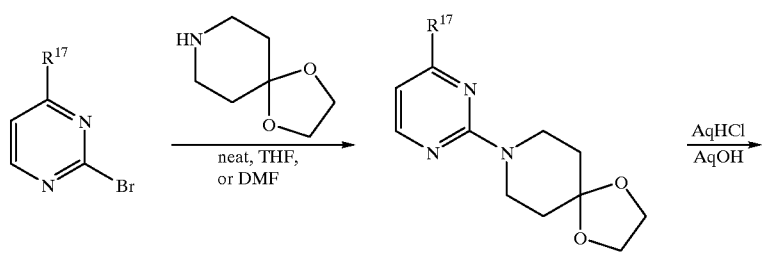
neat, THF, or DMF
AqHCl / AqOH

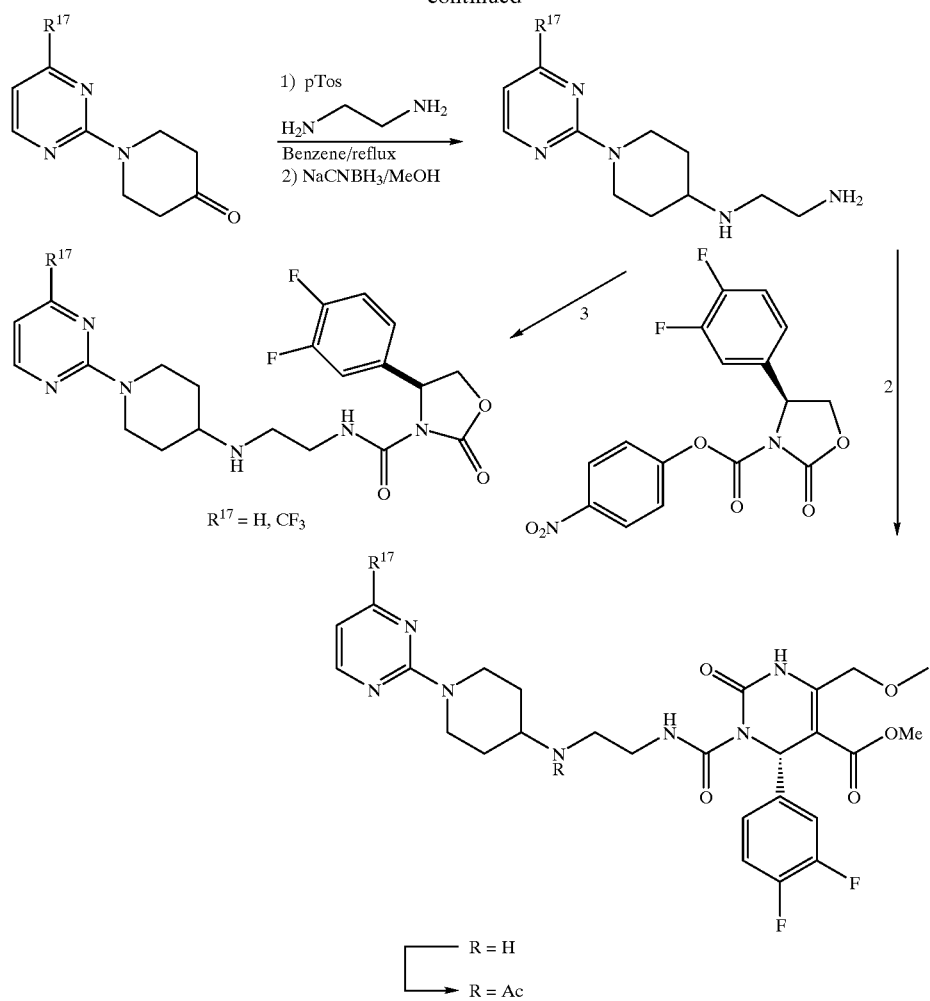
SCHEME 3B
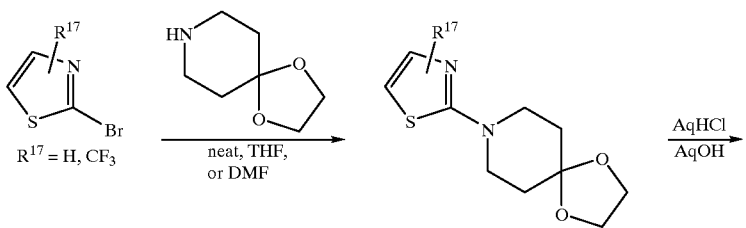

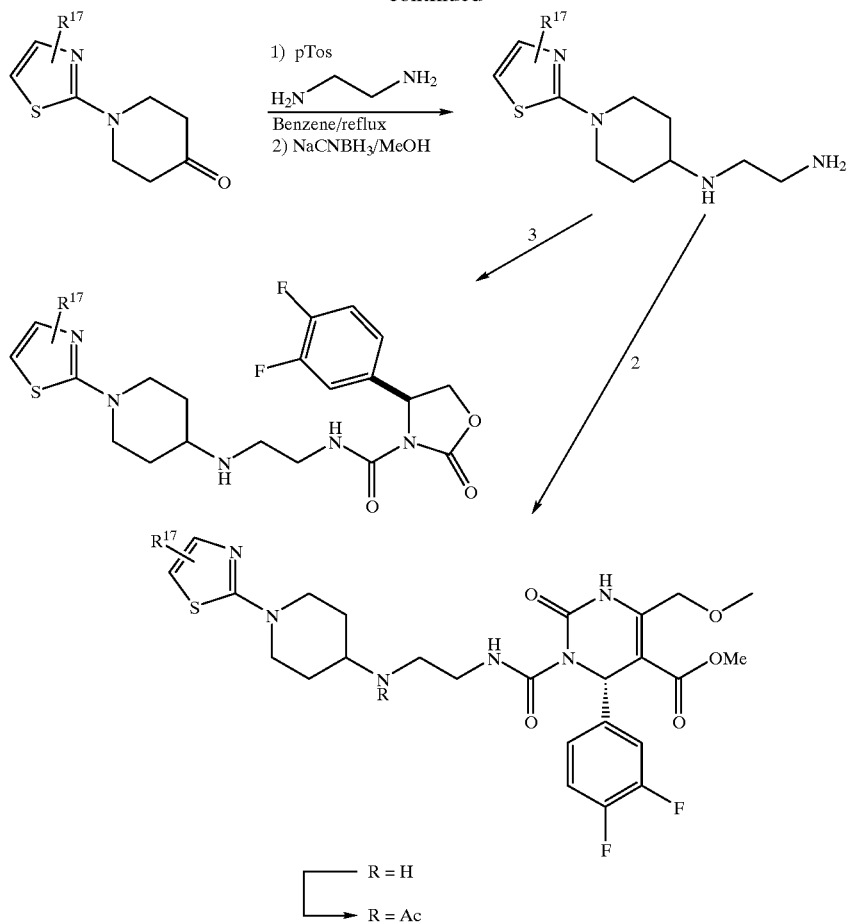

Pyrrolidinyl and azetidinyl analogs are prepared as shown in Schemes 4 and 5. Addition of 3-hydroxypyrrolidine to, for instance, 2-fluorobenzonitrile, followed by Swern oxidation provided the required N-aryl-3-oxopyrrolidine. Reductive amination with mono N-Boc ethylenediamine, followed by, HCl-EtOAc protection and selective acylation provided the representative example as shown in Scheme 4. The azetidinyl analog was prepared in analogous fashion starting from 3-hydroxy azetidine as shown in Scheme 5.

SCHEME 4

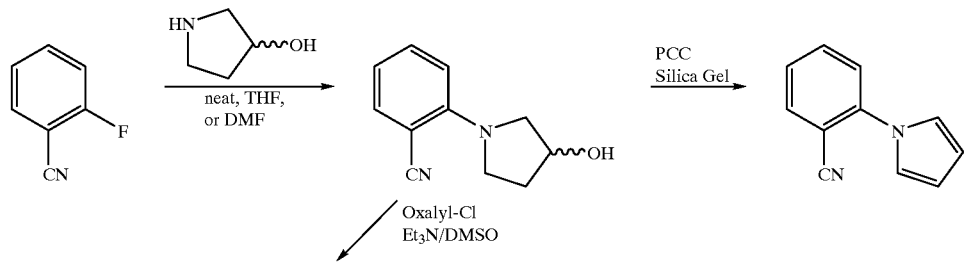

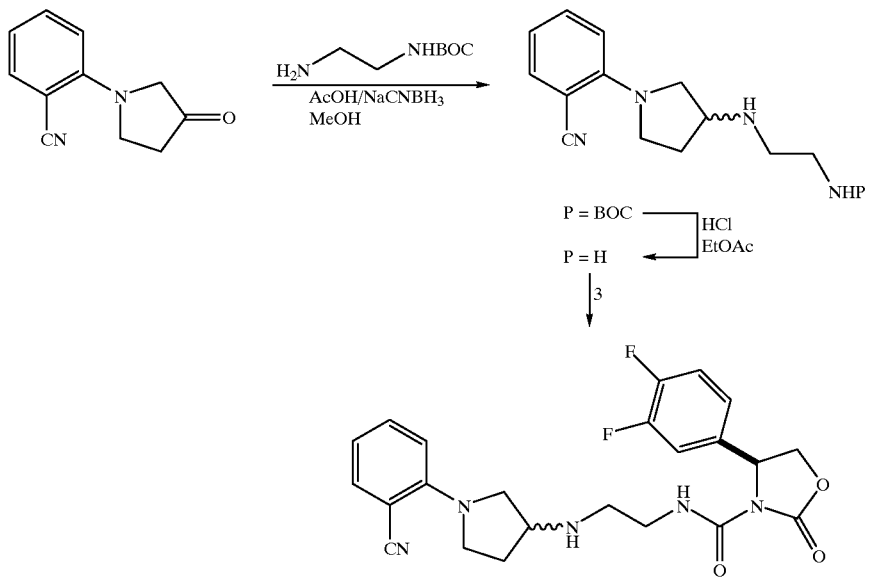
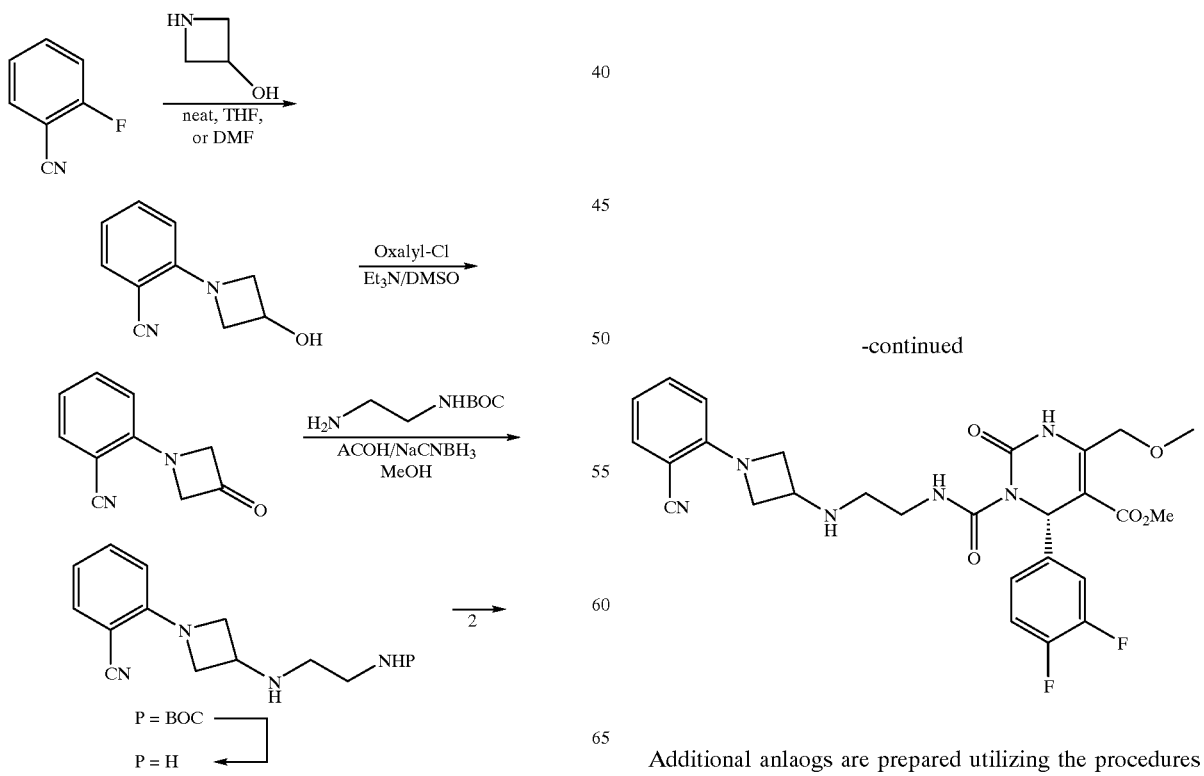
Additional anlaogs are prepared utilizing the procedures of Schemes 6–9.

SCHEME 6
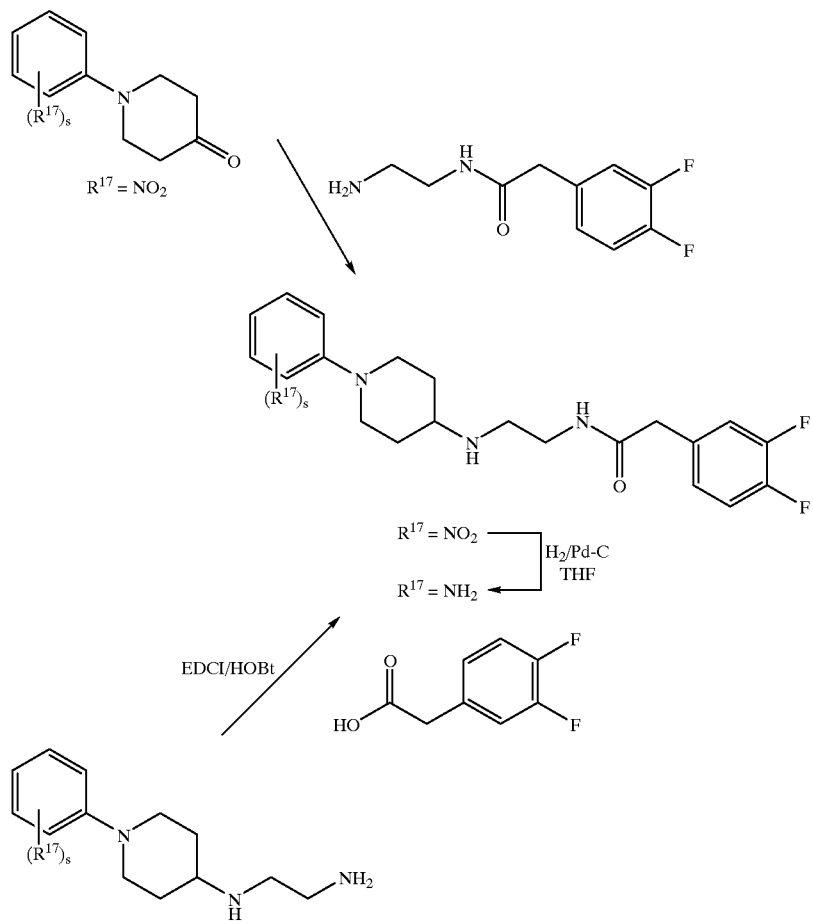
SCHEME 7
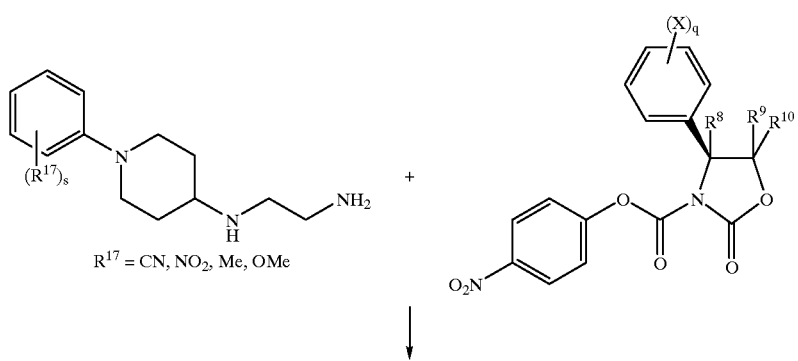

-continued
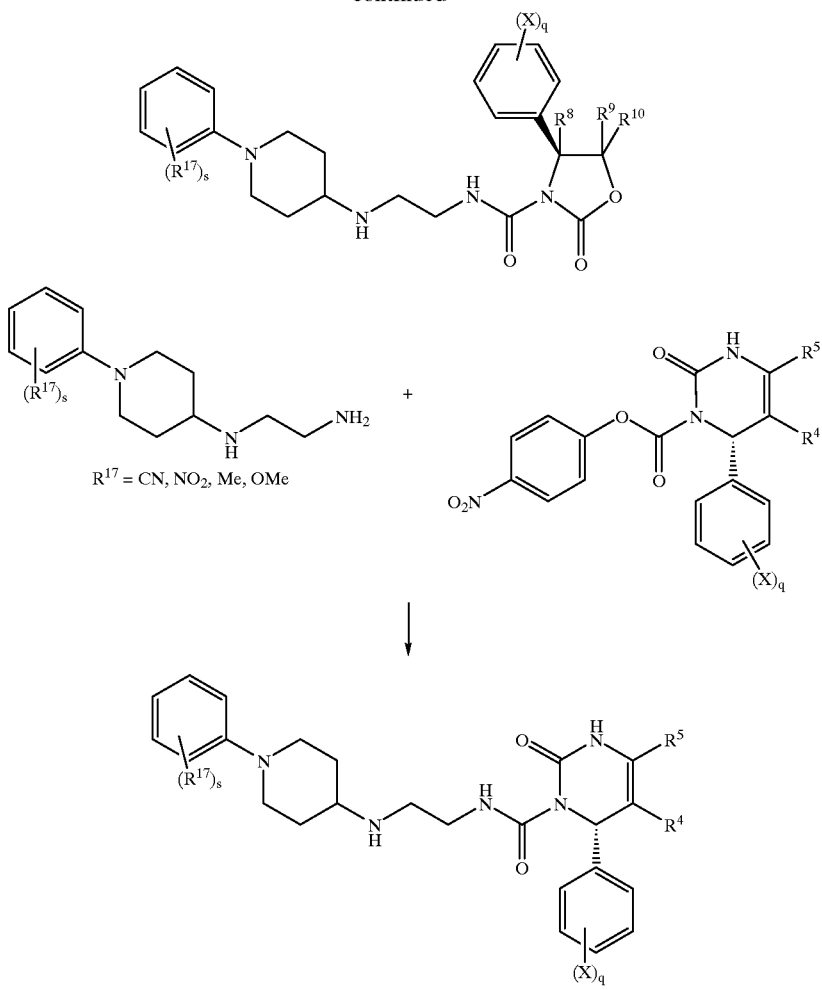
SCHEME 8
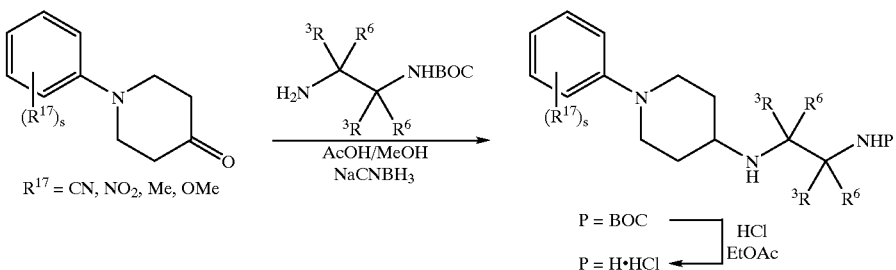

-continued
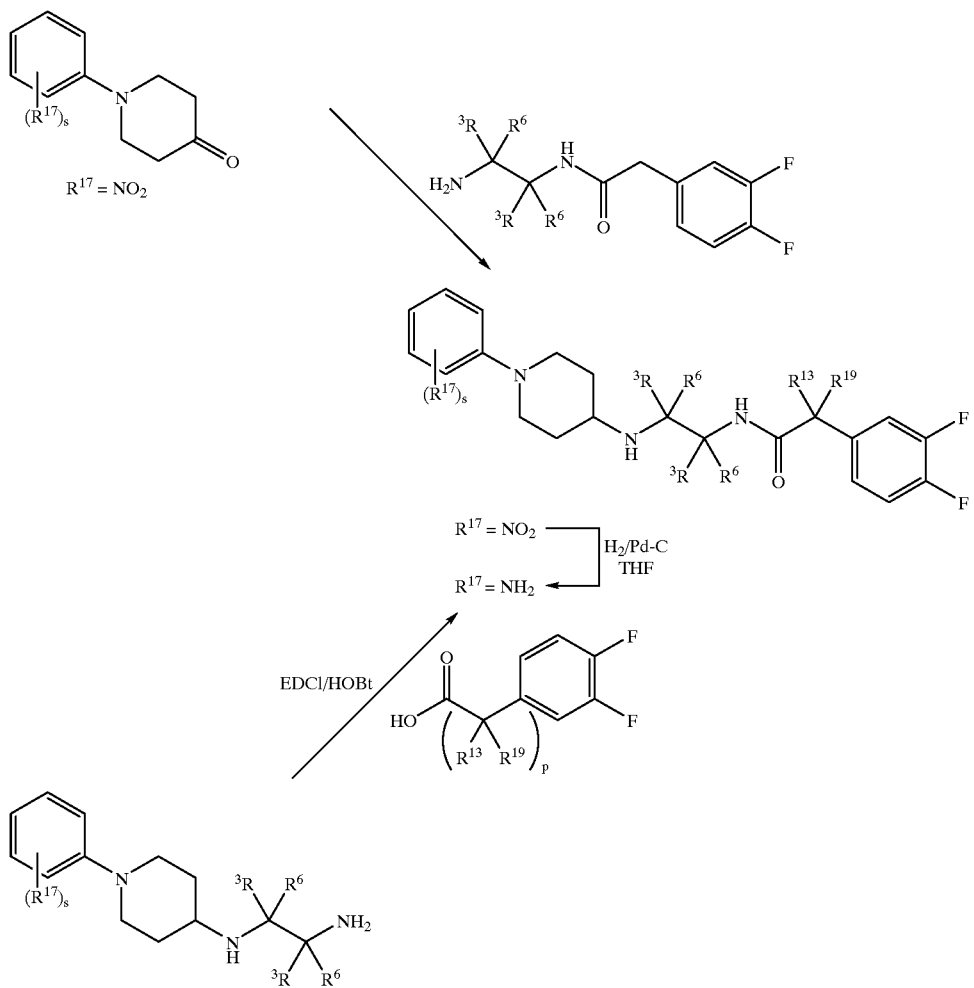

SCHEME 9
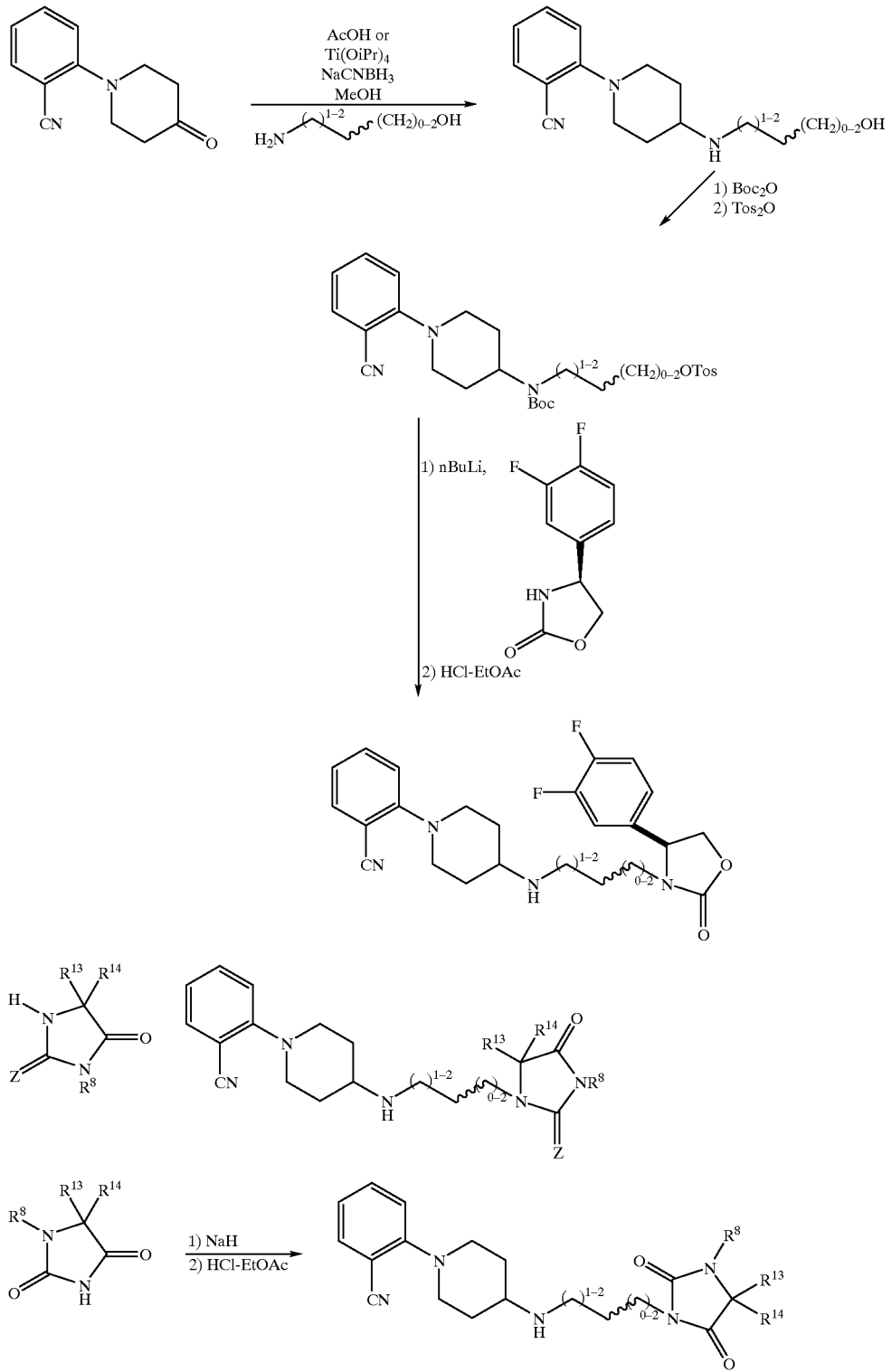

-continued

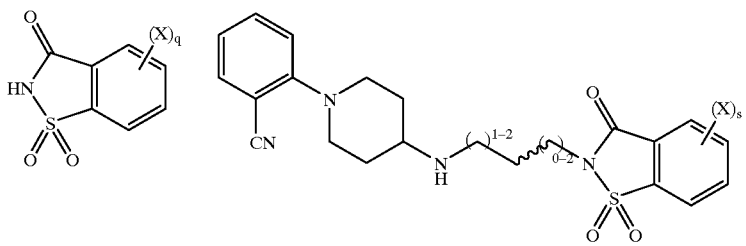

The following examples are provided to further define the invention without, however, limiting the invention to the particulars of these examples.

EXAMPLE 1

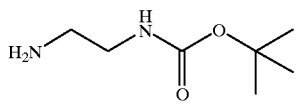

1 tert-Butyl N-(2-aminoethyl)carbamate (1)

A solution of ethylenediamine (39.8 g, 0.663 mole) in THF (1 L) was cooled to 0° C. and treated with a solution of di-tert-butyldicarbonate (22.2 g, 0.101 mole) in THF (500 mL) dropwise over 6 h. The resulting mixture was stirred at room temperature overnight. The solvent was removed in vacuo and the residue dissolved in ethyl acetate and brine. The organic layer was washed with two additional portions of brine and dried over $Na_2SO_4$. The solvent was removed in vacuo to afford the title compound (1) as a pale yellow liquid.

EXAMPLE 2

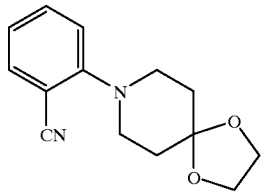

4

N-(2-Cyanophenyl)-4-piperidone ethylene ketal (4)

A solution of 2-fluorobenzonitrile (2.75 g, 22.7 mmol) and 4-piperidone ethylene ketal (4.25 g, 29.7 mmol) in DMF (40 mL) was heated to 120° C. for 4 h. The resulting mixture was cooled to room temperature overnight. The solvent was removed in vacuo and the residue dissolved in ether and sodium bicarbonate solution. The aqueous layer was extracted with two additional portions of ether and the combined organic extracts were washed with brine, dried over $Na_2SO_4$, and concentrated under reduced pressure to afford the title compound (4). The crude product was used directly.

EXAMPLE 3

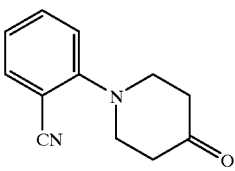

5

N-(2-Cyanophenyl)-4-piperidone (5)

A solution of 4 (533 mg, 2.18 mmol) in ether (10 mL) was treated with 5% aqueous HCl (20 mL). The mixture was stirred at room temperature (11 d). The reaction was diluted with ether and neutralized with sodium bicarbonate solution. The aqueous layer was extracted with two additional portions of ether and the combined organic extracts were washed with brine, dried over $Na_2SO_4$, and concentrated under reduced pressure. PCTLC ($SiO_2$, 4 mm, 20% EtOAc-80% hexane) afforded the title compound (5).

$^1$H NMR ($CDCl_3$, 400 MHz) consistent with assigned structure.

FABLRMS m/e 201 g/mole ($M^+$+H, $C_{12}H_{12}N_2O$=201 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=7.32 min; focus=215 nm; 97.5% pure.

EXAMPLE 4

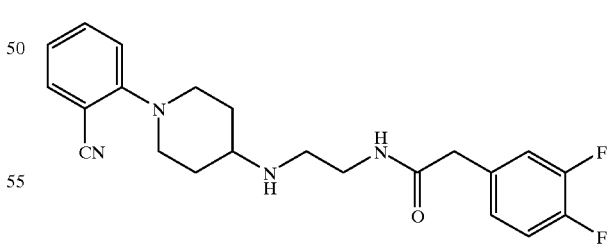

6

N-(2-(1-(2-Cyanophenyl)piperidin-4-ylamino)ethyl)-2-(3,4-difluoro-phenyl)acetamide (6)

A solution of 5 (190 mg, 0.94 mmol), N-(2-aminoethyl)-1-(3,4-difluorophenyl)acetamide (120 mg, 0.56 mmol), and acetic acid (168 mg, 2.79 mmol) in methanol (2 mL) was treated with sodium cyanoborohydride (35 mg, 0.56 mmol) at room temperature. The resulting mixture was stirred at room temperature (30 min). The solvent was removed in vacuo and the residue dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC ($SiO_2$, 4 mm, 10% EtOH-90% $CHCl_3$) afforded the title compound (6) which was converted to the hydrochloride salt after treatment with methanolic HCl.

$^1$H NMR ($CDCl_3$, 400 MHz) consistent with assigned structure.

FABLRMS m/e 399 g/mole ($M^++H$, $C_{22}H_{24}F_2N_4O$=399 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=7.97 min; focus=215 nm; 98.5% pure.

EXAMPLE 5

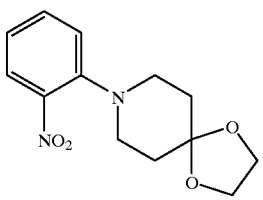

7

N-(2-Nitrophenyl)-4-piperidone ethylene ketal (7)

A solution of 1-fluoro-2-nitrobenzene (5.80 g, 41.1 mmol) and 4-piperidone ethylene ketal (6.68 g, 46.6 mmol) in THF (100 mL) was stirred at room temperature (2 h). The resulting mixture was washed with water and sodium bicarbonate solution. The aqueous layer was extracted with two portions of ethyl acetate and the combined organic extracts were washed with brine, dried over $Na_2SO_4$, and concentrated under reduced pressure. Flash chromatography on silica gel (10% ethyl acetate/hexane) afforded the title compound (7).

$^1$H NMR ($CDCl_3$, 400 MHz) consistent with assigned structure.

FABLRMS m/e 265 g/mole ($M^++H$, $C_{13}H_{16}N_2O_4$ =265 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=9.12 min; focus=215 nm; 100% pure.

EXAMPLE 6

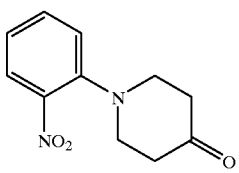

8

N-(2-Nitrophenyl)-4-piperidone (8)

A solution of 7 (7.44 g, 28.1 mmol) in ether (300 mL) was treated with 5% aqueous HCl (150 mL). The mixture was stirred at room temperature (5 d). The reaction was quenched with solid sodium bicarbonate. The aqueous layer was extracted with three additional portions of ether and the combined organic extracts were washed with brine, dried over $Na_2SO_4$, and concentrated under reduced pressure. Flash chromatography on silica gel (20% ethyl acetate/hexane) afforded the title compound (8).

$^1$H NMR ($CDCl_3$, 400 MHz) consistent with assigned structure.

FABLRMS m/e 221 g/mole ($M^++H$, $C_{11}H_{12}N_2O_3$=221 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=7.81 min; focus=215 nm; 100% pure.

EXAMPLE 7

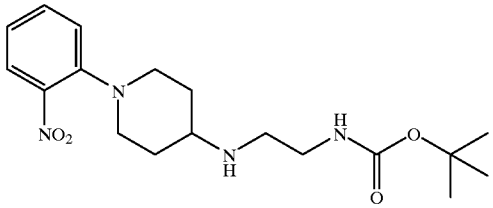

9

(2-(1-(2-Nitro-phenyl)-piperidin-4-ylamino)-ethyl)-carbamic acid tert-butyl ester (9)

A solution of 8 (945 mg, 4.29 mmol), 1 (695 mg, 4.33 mmol), and acetic acid (1.31 g, 21.8 mmol) in methanol (10 mL) was treated with sodium cyanoborohydride (270 mg, 4.29 mmol) at room temperature. The resulting mixture was stirred at room temperature overnight. The solvent was removed in vacuo and the residue dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC ($SiO_2$, 6 mm, 10% EtOH-90% $CHCl_3$) afforded the title compound (9).

$^1$H NMR ($CDCl_3$, 400 MHz) consistent with assigned structure.

FABLRMS m/e 365 g/mole ($M^++H$, $C_{18}H_{28}N_4O_4$=365 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=7.90 min; focus=215 nm; 99% pure.

EXAMPLE 8

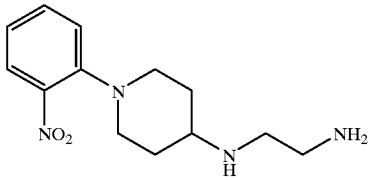

10

$N_1$-(1-(2-Nitrophenyl)piperidin-4-yl)ethane-1,2-diamine (10)

A solution of 9 (576 mg, 1.66 mmol) in ethyl acetate (50 mL) was cooled to 0° C. and treated with anhydrous HCl (5 min). The mixture was. stirred at room temperature (2 h). The solvent was removed in vacuo and the residue disolved in dichloromethane and sodium carbonate solution. The aqueous layer was extracted with two additional portions of dichloromethane. The combined organic extracts were washed with brine, dried over $Na_2SO_4$, and concentrated under reduced pressure to afford the title compound (10). The crude product was used directly.

EXAMPLE 9

11

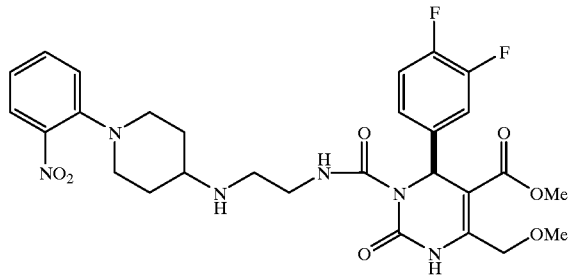

(4S)-4-(3,4-Difluorophenyl)-6-methoxymethyl-3-(2 (1-(2-nitrophenyl)piperidin-4-ylamino) ethylcarbamoyl)-2-oxo-1,2,3,4-tetrahydropyriymidine-5-carboxylic acid methyl ester (11)

A solution of 2 (53 mg, 0.11 mmol) in dichloromethane (1 mL) was treated with a solution of 10 (35 mg, 0.13 mmol) in dichloromethane (1 mL) at room temperature. The mixture was stirred at room temperature (30 min). The mixture was diluted with sodium carbonate solution and the aqueous layer was extracted with two additional portions of dichloromethane. The combined organic extracts were washed with brine and dried over $Na_2SO_4$. The solvent was removed in vacuo. PCTLC ($SiO_2$, 2 mm, 1% $NH_4OEt$-10% EtOH-90% $CHCl_3$) afforded the title compound (11) which was converted to the hydrochloride salt after treatment with methanolic HCl.

$^1H$ NMR ($CDCl_3$, 400 MHz) consistent with assigned structure.

FABLRMS m/e 603 g/mole ($M^+$+H, $C_{28}H_{32}F_2N_6O_7$=603 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=9.53 min; focus=215 nm; 100% pure.

EXAMPLE 10

12

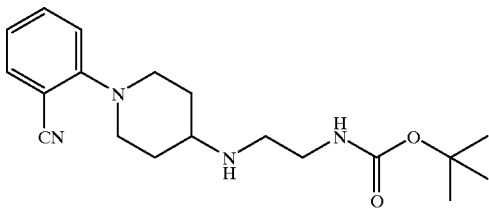

(2-(1-(2-Cyanophenyl)piperidin-4-ylamino)ethyl) carbamic acid tert-butyl ester (12)

A solution of 5 (200 mg, 1.00 mmol), 1 (161 mg, 1.00 mmol), and acetic acid (300 mg, 5.00 mmol) in methanol (2 mL) was treated with sodium cyanoborohydride (66 mg, 1.05 mmol) at room temperature. The resulting mixture was stirred at room temperature overnight. The solvent was removed in vacuo and the residue dissolved in dichloromethane and sodium bicarbonate solution. The aqueous layer was extracted with three additional portions of dichloromethane and the combined organic extracts were washed with brine, dried over $Na_2SO_4$, and concentrated under reduced pressure. PCTLC ($SiO_2$, 4 mm, 10% EtOH-90% $CHCl_3$) afforded the title compound (12).

$^1H$ NMR ($CDCl_3$, 400 MHz) consistent with assigned structure.

FABLRMS m/e 345 g/mole ($M^+$+H, $C_{19}H_{28}N_4O_2$=345 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=7.66 min; focus=215 nm; 92% pure.

EXAMPLE 11

13

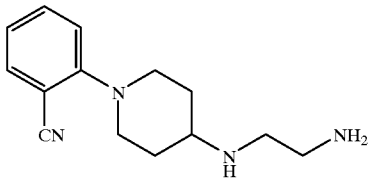

2-(4-(2-Aminoethylamino)piperidin-1-yl) benzonitrile (13)

A solution of 12 (256 mg, 0.74 mmol) in ethyl acetate (50 mL) was cooled to 0° C. and treated with anhydrous HCl (1 min). The mixture was stirred at room temperature (1 h). The solvent was removed in vacuo and the residue disolved in dichloromethane and sodium carbonate solution. The aqueous layer was extracted with two additional portions of dichioromethane. The combined organic extracts were washed with brine, dried over $Na_2SO_4$, and concentrated under reduced pressure to afford the title compound (13). The crude product was used directly.

FABLRMS m/e 245 g/mole ($M^+$+H, $C_{14}H_{20}N_4$=245 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=5.15 min; focus=215 nm; 93.5% pure.

EXAMPLE 12

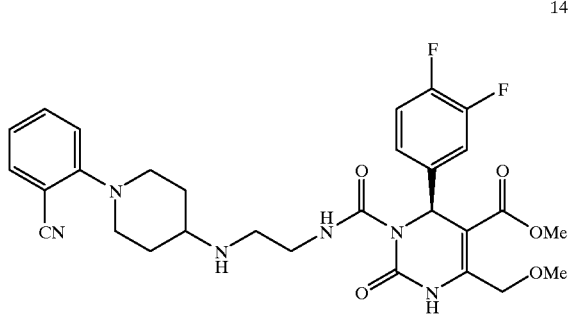

14

(4S)-3-(2-(1-(2-Cyanophenyl)piperidin-4-ylamino)
ethylcarbamoyl)-4-(3,4-difluorophenyl)-6-
methoxymethyl-2-oxo-1,2,3,4-tetrahydropyrimidine-
5-carboxylic acid methyl ester (14)

A solution of 2 (77 mg, 0.16 mmol) in dichloromethane (1 mL) was treated with a solution of 13 (50 mg, 0.20 mmol) in dichloromethane (1 mL) at room temperature. The mixture was stirred at room temperature (1 h). The mixture was diluted with sodium carbonate solution and the aqueous layer was extracted with two additional portions of dichloromethane. The combined organic extracts were washed with brine and dried over $Na_2SO_4$. The solvent was removed in vacuo. PCTLC ($SiO_2$, 2 mm, 1% $NH_4OEt$-10% EtOH-90% $CHCl_3$) afforded the title compound (14) which was converted to the hydrochloride salt after treatment with methanolic HCl.

$^1H$ NMR ($CDCl_3$, 400 MHz) consistent with assigned structure.

FABLRMS m/e 583 g/mole ($M^++H$, $C_{29}H_{32}F_2N_6O_5$=583 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=9.34 min; focus=215 nm; 100% pure.

EXAMPLE 13

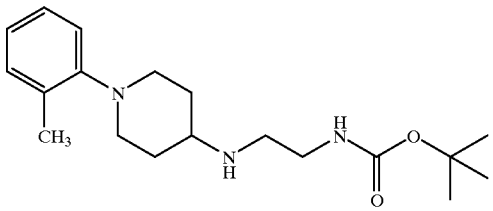

15

(2-(1-o-Tolyl-piperidin-4-ylamino)-ethyl)-carbamic acid tert-butyl ester (15)

Following the procedure of Example 7, but using N-o-tolyl-4-piperidone in place of N-(2-nitrophenyl)4-piperidone, the crude compound was obtained. PCTLC ($SiO_2$, 2 mm, 10% EtOH-90% $CHCl_3$) afforded the title compound (15).

FABLRMS m/e 334 g/mole ($M^++H$, $C_{19}H_{31}N_3O_2$=334 g/mole.)

EXAMPLE 14

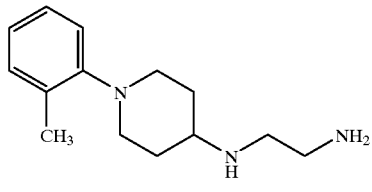

16

$N_1$(1-o-Tolylpiperidin-4-yl)ethane-1,2-diamine (16)

A solution of 15 (115 mg, 0.344 mmol) in ethyl acetate (2 mL) was treated with sat'd HCl/EtOAc solution (3 mL) at room temperature. The mixture was stirred at room temperature (1 h). The solvent was removed in vacuo and the residue dissolved in dichloromethane and sodium carbonate solution. The aqueous layer was extracted with two additional portions of dichloromethane and the combined organic extracts were washed with brine, dried over $Na_2SO_4$, and concentrated under reduced pressure to afford the title compound (16). The crude product was used directly.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=4.82 min; focus=215 nm; 98.5% pure.

EXAMPLE 15

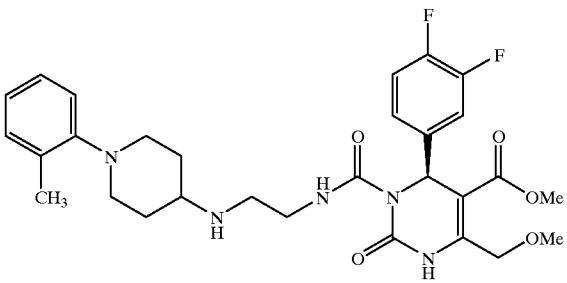

17

(4S)-4-(3,4-Difluorophenyl)-6-methoxymethyl-2-
oxo-3-(2-(1-o-tolylpiperidin-4-ylamino)
ethylcarbamoyl)-1,2,3,4-tetrahydro-pyrimidine-5-
carboxylic acid methyl ester (17)

A solution of 16 (51 mg, 0.218 mmol) in dichloromethane (1 mL) was treated with solid 2 (88 mg, 0.184 mmol) at room temperature. The mixture was stirred at room temperature (30 min). The mixture was diluted with sodium carbonate solution and the aqueous layer was extracted with two additional portions of dichloromethane. The combined organic extracts were washed with brine and dried over $Na_2SO_4$. The solvent was removed in vacuo. PCTLC ($SiO_2$, 2 mm, 1% $NH_4OEt$-10% EtOH-90% $CHCl_3$) afforded the title compound (17) which was converted to the hydrochloride salt after treatment with methanolic HCl.

$^1H$ NMR ($CDCl_3$, 400 MHz) consistent with assigned structure.

FABLRMS m/e 572 g/mole ($M^++H$, $C_{29}H_{35}F_2N_5O_5$=572 g/mole.)

HPLC (Vydac; C18; diameter=4.6 mm; length=150 mm; gradient=$H_2O$ [0.1% $H_3PO_4$]—$CH_3CN$, 95%–5%,

EXAMPLE 16

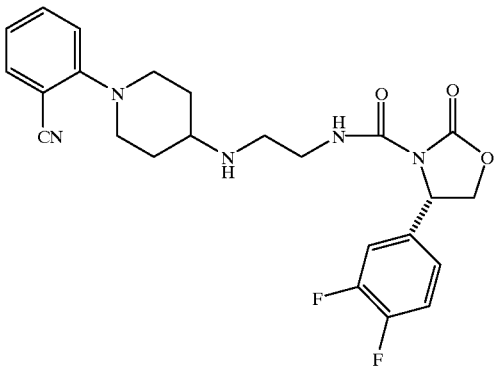

(4S)-4-(3,4-Difluorophenyl)-2-oxo-oxazolidine-3-carboxylic acid (2-(1-(2-cyanophenyl)piperidin-4-ylamino)ethyl)amide (18)

A solution of 13 (61 mg, 0.249 mmol) in dichloromethane (2 mL) was treated with solid 3 (66 mg, 0.181 mmol) at room temperature. The mixture was stirred at room temperature overnight. The mixture was diluted with sodium carbonate solution and the aqueous layer was extracted with two additional portions of dichloromethane. The combined organic extracts were washed with brine and dried over $Na_2SO_4$. The solvent was removed in vacuo. PCTLC ($SiO_2$, 2 mm, 10% EtOH-90% $CHCl_3$) afforded the title compound (18) which was converted to the hydrochloride salt after treatment with methanolic HCl.

$^1$H NMR ($CDCl_3$, 400 MHz) consistent with assigned structure.

FABLRMS m/e 470 g/mole ($M^++H$, $C_{24}H_{25}F_2N_5O_3$=470 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=8.31 min; focus=215 nm; 97% pure.

Anal. Calcd for $C_{24}H_{25}F_2N_5O_3$·0.90 HCl·0.40 $H_2O$: C=56.08; H=5.33; N=13.63. Found: C=56.13; H=5.34; N=13.24.

EXAMPLE 17

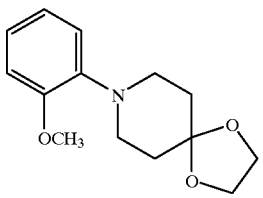

N-(2-Methoxyphenyl)-4-piperidone ethylene ketal (19)

A solution of 2-bromoanisole (6.00 g, 32.08 mmol) and 4-piperidone ethylene ketal (5.54 g, 38.69 mmol) in toluene (250 mL) was treated with sodium tert-butoxide (4.40 g, 45.76 mmol), tri-o-tolylphosphine (411 mg, 1.35 mmol), and tris(dibenzylideneacetone)dipalladium(0) (295 mg, 0.32 mmol) at room temperature. The mixture was heated in an oil bath (100° C., 2 h). The mixture was diluted with ether and the organics washed with brine, dried over $Na_2SO_4$, and concentrated under reduced pressure. Flash chromatography on silica gel (20% ethyl acetate/hexane) afforded the title compound (19).

EXAMPLE 18

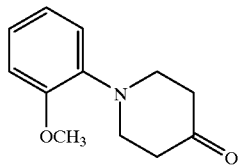

N-(2-Methoxyphenyl)-4-piperidone (20)

A solution of 19 (570 mg, 2.28 mmol) in acetic acid (20 mL), water (20 ml), and concetrated HCl (5 mL) was heated in an oil bath (50° C.) overnight. The solvent was removed in vacuo and the residue dissolved in ether and sodium carbonate solution. The aqueous layer was extracted with two additional portions of ether and the combined organic extracts were washed with brine, dried over $Na_2SO_4$, and concentrated under reduced pressure. PCTLC ($SiO_2$, 2 mm, $CHCl_3$) afforded the title compound (20)

$^1$H NMR ($CDCl_3$, 400 MHz) consistent with assigned structure.

FABLRMS m/e 206 g/mole ($M^++H$, $C_{12}H_{15}NO_2$=206 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=3.07 min; focus=215 nm; 99% pure.

EXAMPLE 19

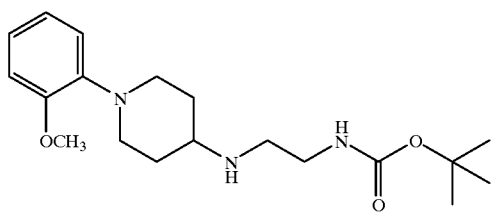

(2-(1-(2-Methoxyphenyl)piperidin-4-ylamino)-ethyl)carbamic acid tert-butyl ester (21)

A solution of 20 (186 mg, 0.906 mmol), 1 (153 mg, 0.955 mmol), and acetic acid (288 mg, 4.80 mmol) in methanol (1 mL) was treated with sodium cyanoborohydride (63 mg, 1.00 mmol) at room temperature. The resulting mixture was stirred at room temperature (2 h). The solvent was removed in vacuo and the residue dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC (SiO$_2$, 2 mm, 10% EtOH; 90% CHCl$_3$) afforded the title compound (21).

$^1$H NMR (CDCl$_3$, 400 MHz) consistent with assigned structure.

FABLRMS m/e 350 g/mole (M$^+$+H, C$_{19}$H$_{31}$N$_3$O$_3$=350 g/mole.)

EXAMPLE 20

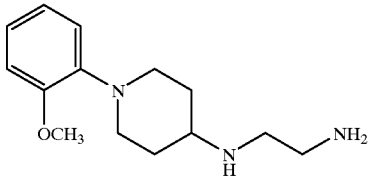

N$_1$-(1-(2-Methoxyphenyl)piperidin-4-yl)ethane-1,2-diamine (22)

Following the procedure of Example 14, but using (21) in place of (15), the title compound (22) was obtained. The crude product was used directly.

FABLRMS m/e 250 g/mole (M$^+$+H, C$_{14}$H$_{23}$N$_3$O=250 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=3.60 min; focus=215 nm; 100% pure.

EXAMPLE 21

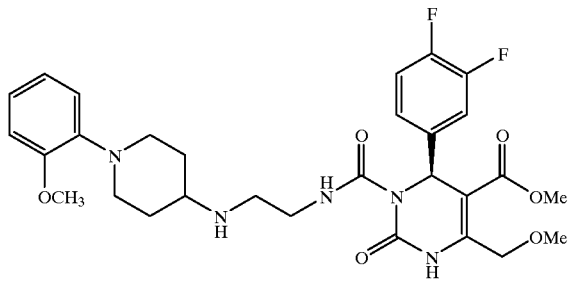

(4S)-4-(3,4-Difluorophenyl)-6-methoxymethyl-3-(2-(1-(2-methoxyphenyl)-piperidin-4-ylamino)ethylcarbamoyl)-2-oxo-1,2,3,4,-tetrahydro-pyrimidine-5-carboxylic acid methyl ester (23)

Following the procedure of Example 15, but using (22) in place of (16), the crude product (23) was obtained. PCTLC (SiO$_2$, 2 mm, 10% EtOH-90% CHCl$_3$) afforded the title compound (23) which was converted to the hydrochloride salt after treatment with methanolic HCl.

$^1$H NMR (CDCl$_3$, 400 MHz) consistent with assigned structure.

FABLRMS m/e 588 g/mole (M$^+$+H, C$_{29}$H$_{35}$F$_2$N$_5$O$_6$=588 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=7.70 min; focus=215 nm; 96.3% pure.

Anal. Calcd for C$_{29}$H$_{35}$F$_2$N$_5$O$_6$·2.00 HCl·0.50 H$_2$O: C=52.02; H=5.72; N=10.46. Found: C=52.04; H=5.78; N=10.30.

EXAMPLE 22

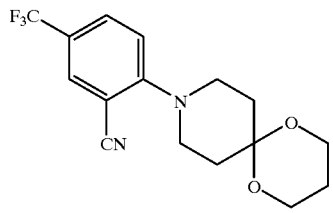

N-(2-Cyano-4-trifluoromethylphenyl)-4-piperidone propylene ketal (24)

A solution of 2-fluoro-5-trifluoromethylbenzonitrile (2.01 g, 10.61 mmol) and 4-piperidone propylene ketal (1.71 g, 10.9 mmol) in THF (10 mL) was stirred at room temperature (1 h). The resulting mixture was diluted with ether and sodium carbonate solution. The aqueous layer was extracted with two portions of ether and the combined organic extracts were washed with brine, dried over Na$_2$SO$_4$, and concentrated under reduced pressure to afford the title compound (24).

FABLRMS m/e 327 g/mole (M$^+$+H, C$_{16}$H$_{17}$F$_3$N$_2$O$_2$=327 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=11.04 min; focus=255 nm; 97.2% pure.

EXAMPLE 23

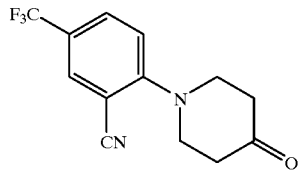

N-(2-Cyano-4-trifluoromethylphenyl)-4-piperidone (25)

A solution of 24 (1.70 g, 5.20 mmol) in ether (20 mL) was treated with 6N aqueous HCl (50 mL). The mixture was stirred at room temperature (20 min). The reaction mixture was neutralized with sodium carbonate solution and solid sodium hydroxide. The aqueous layer was extracted with two additional portions of ether and the combined organic extracts were washed with brine, dried over Na$_2$SO$_4$, and concentrated under reduced pressure. PCTLC (SiO$_2$, 6 mm, 10% EtOH-90% CHCl$_3$) afforded the title compound (25).

$^1$H NMR (CDCl$_3$, 400 MHz) consistent with assigned structure.

FABLRMS m/e 269 g/mole (M$^+$+H, C$_{13}$H$_{11}$F$_3$N$_2$O=269 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=9.35 min; focus=215 nm; 98.9% pure.

EXAMPLE 24

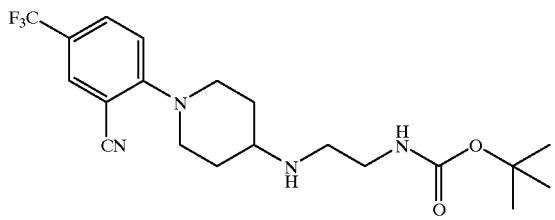

26

(2-(1-(2-Cyano-4-trifluoromethylphenyl)piperidin-4-ylamino)-ethyl)carbamic acid tert-butyl ester (26)

A solution of 25 (535 mg, 1.99 mmol), 1 (335 mg, 2.09 mmol), and acetic acid (629 mg, 10.48 mmol) in methanol(2 mL)/dichloroethane(1 mL) was treated with sodium cyanoborohydride (130 mg, 2.06 mmol) at room temperature. The resulting mixture was stirred at room temperature overnight. The solvent was removed in vacuo and the residue dissolved in dichloromethane and sodium carbonate solution. The aqueous layer was extracted with two additional portions of dichloromethane and the combined organic extracts were washed with brine, dried over $Na_2SO_4$, and concentrated under reduced pressure. PCTLC ($SiO_2$, 4 mm, 10% EtOH-90% $CHCl_3$) afforded the title compound (26).

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=9.16 min; focus=215 nm; 100% pure.

EXAMPLE 25

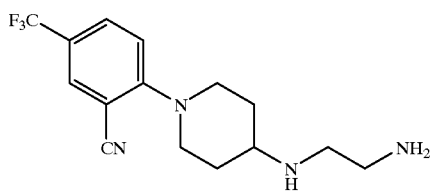

27

2-(4-(2-Aminoethylamino)piperidin-1-yl)-5-trifluoromethyl-benzonitrile (27)

Following the procedure of Example 14, but using (26) in place of (15), the title compound (27) was obtained.

FABLRMS m/e 313 g/mole (M$^+$+H, $C_{15}H_{19}F_3N$=313 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=6.81 min; focus=215 nm; 95.2% pure.

EXAMPLE 26

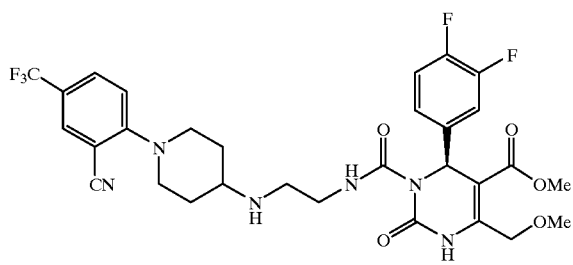

28

(4S)-3-(2-(1-(2-Cyano-4-trifluoromethylphenyl)piperidin-4-ylamino)-ethylcarbamoyl)-4-(3,4-difluorophenyl)-6-methoxymethyl-2-oxo-1,2,3,4-tetrahydropyrimidine-5-carboxylic acid methyl ester (28)

Following the procedure of Example 15, but using (27) in place of (16), the crude product was obtained. PCTLC ($SiO_2$, 2 mm, 1% $NH_4OEt$-10% EtOH-90% $CHCl_3$) afforded the title compound (28) which was converted to the hydrochloride salt after treatment with methanolic HCl.

$^1$H NMR ($CDCl_3$, 400 MHz) consistent with assigned structure.

FABLRMS m/e 651 g/mole (M$^+$+H, $C_{30}H_{31}F_5N_6O_5$=651 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=10.49 min; focus=215 nm; 97.7% pure.

Anal. Calcd for $C_{30}H_{31}F_5N_6O_5 \cdot 1.15$ HCl: C=52.03; H=4.68; N=12.14. Found: C=52.17; H=4.45; N=11.76.

EXAMPLE 27

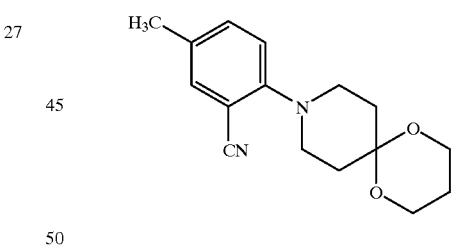

29

N-(2-Cyano-4-methylphenyl)-4-piperidone propylene ketal (29)

A solution of 2-fluoro-5-methylbenzonitrile (2.76 g, 20.4 mmol) and 4-piperidone propylene ketal (3.39 g, 21.5 mmol) in DMF (50 mL) was heated in an oil bath (90° C., 20 h). The mixture was diluted with ether and sodium carbonate solution. The aqueous layer was extracted with two additional portions of ether and the combined organic extracts were washed with brine, dried over $Na_2SO_4$, and concentrated under reduced pressure. PCTLC ($SiO_2$, 6 mm, 50-0% hexane/$CHCl_3$) afforded the title compound (29).

$^1$H NMR ($CDCl_3$, 400 MHz) consistent with assigned structure.

FABLRMS m/e 273 g/mole (M$^+$+H, $C_{16}H_{20}N_2O_2$=273 g/mole.)

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=9.97 min; focus=215 nm; 97.8% pure.

EXAMPLE 28

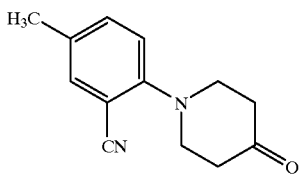

N-(2-Cyano-4-methylphenyl)-4-piperidone (30)

A solution of 29 (549 mg, 2.00 mmol) in ether (20 mL) was treated with 3N aqueous HCl (25 mL). The mixture was stirred at room temperature (24 h). The solvent was removed in vacuo and the residue dissolved in 6N HCl (25 mL) and acetic acid (10 mL). The mixture was stirred at room temperature (3 h). The reaction mixture was neutralized with sodium carbonate solution and the aqueous layer was extracted with three portions of ether. The combined organic extracts were washed with brine, dried over Na₂SO₄, and concentrated under reduced pressure to afford the title compound (30).

FABLRMS m/e 215 g/mole (M⁺+H, C₁₃H₁₄N₂O=215 g/mole.)

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=8.55 min; focus=215 nm; 88.5% pure.

EXAMPLE 29

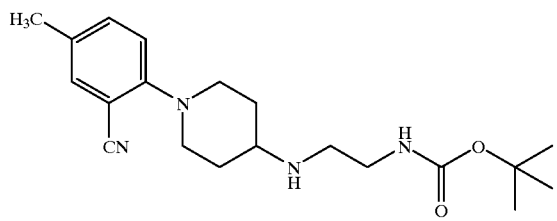

(2-(1-(2-Cyano-4-methylphenyl)piperidin-4-ylamino)ethyl)carbamic acid tert-butyl ester (31)

Following the procedure of Example 7, but using (30) in place of (8), the crude product was obtained. PCTLC (SiO₂, 4 mm, 10% EtOH-90% CHCl₃) afforded the title compound (31).

FABLRMS m/e 359 g/mole (M⁺+H, C₂₀H₃₀N₄O₂=359 g/mole.)

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=8.36 min; focus=215 nm; 100% pure.

EXAMPLE 30

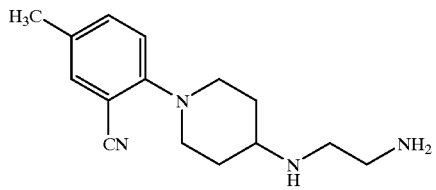

2-(4-(2-Aminoethylamino)piperidin-1-yl)-5-methylbenzonitrile (32)

Following the procedure of Example 14, but using (31) in place of (15), the title compound (32) was obtained.

FABLRMS m/e 259 g/mole (M⁺+H, C₁₅H₂₂N₄=259 g/mole.)

HPLC (Vydac; C18; diameter=4.6 mm; length=150 mm; gradient=H₂O [0. 1% H₃PO₄]—CH₃CN, 95%–5%, 5%–95%, over 16 minutes, 2 ml/min flow rate) RT=5.98 min; focus=215 nm; 100% pure.

EXAMPLE 31

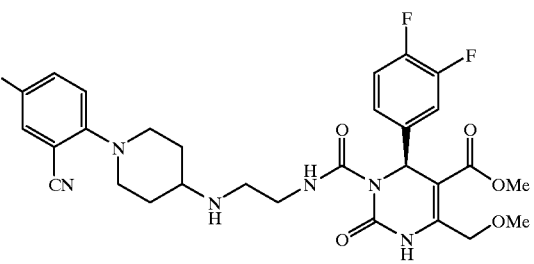

(4S)-3-(2-(1-(2-Cyano-4-methylphenyl)piperidin-4-amino)ethylcarbamoyl)-4-(3,4-difluorophenyl)-6-methoxymethyl-2-oxo-1,2,3,4-tetrahydropyrimidine-5-carboxylic acid methyl ester (33)

Following the procedure of Example 15, but using (32) in place of (16), the crude product was obtained. PCTLC (SiO₂, 2 mm, 10% EtOH; 90% CHCl₃) afforded the title compound (33) as the hydrochloride salt after treatment with EtOAc/HCl.

¹H NMR (CDCl₃, 400 MHz) consistent with assigned structure.

FABLRMS m/e 597 g/mole (M⁺+H, C₃₀H₃₄F₂N₆O₅=597 g/mole.)

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=9.79 min; focus=215 nm; 99.7% pure.

EXAMPLE 32

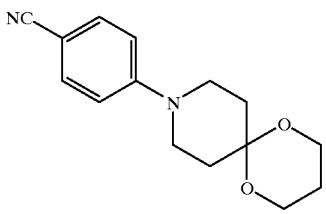

34

N-(4-Cyanophenyl)-4-piperidone propylene ketal (34)

A mixture of 4-fluorobenzonitrile (1.22 g, 10.0 mmol) and 4-piperidone propylene ketal (2.02 g, 12.85 mmol) was stirred at room temperature overnight. The resulting mixture was diluted with dichloromethane and sodium carbonate solution and the aqueous layer was extracted with two additional portions of dichloromethane. The combined organic extracts were washed with brine and dried over $Na_2SO_4$. The solvent was removed in vacuo. PCTLC ($SiO_2$, 6 mm, 10% EtOH-90% $CHCl_3$) afforded the title compound (34).

$^1$H NMR ($CDCl_3$, 400 MHz) consistent with assigned structure.

FABLRMS m/e 259 g/mole ($M^+$+H, $C_{15}H_{18}N_2O_2$=259 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=8.62 min; focus=215 nm; 100% pure.

EXAMPLE 33

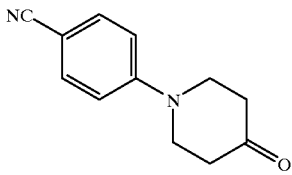

35

N-(4-Cyanophenyl)-4-piperidone (35)

A solution of 34 (915 mg, 3.54 mmol) in ether (6 mL) was treated with 6N aqueous HCl (25 mL). The mixture was stirred at room temperature (2 d). The solvent was removed in vacuo and the residue dissolved in 3N HCl (25 mL) and acetic acid (20 mL). The mixture was stirred at room temperature (2 h). The solvent was removed in vacuo and the residue dissolved in dichloromethane and sodium carbonate solution. The aqueous layer was extracted with two additional portions of dichloromethane and the combined organic extracts were washed with brine, dried over $Na_2SO_4$, and concentrated under reduced pressure. PCTLC ($SiO_2$, 4 mm, 10% EtOH-90% $CHCl_3$) afforded the title compound (35).

HPLC (Vydac; C18; diameter=4.6 mm; length=150 mm; gradient=$H_2O$ [0. 1% $H_3PO_4$]—$CH_3CN$, 95%–5%, 5%–95%, over 16 minutes, 2 ml/min flow rate) RT=6.86 min; focus=215 nm; 99% pure.

EXAMPLE 34

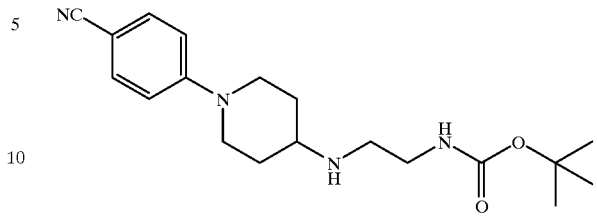

36

(2-(1-(4-Cyanophenyl)piperidin-4-ylamino)ethyl) carbamic acid tert-butyl ester (36)

A solution of 35 (415 mg, 2.07 mmol), 1 (343 mg, 2.14 mmol), and acetic acid (629 mg, 10.48 mmol) in methanol (10 mL) was treated with sodium cyanoborohydride (140 mg, 2.23 mmol) at room temperature. The resulting mixture was stirred at room temperature (3 h). The solvent was removed in vacuo. PCTLC ($SiO_2$, 4 mm, 10% EtOH-90% $CHCl_3$) afforded the title compound (36).

$^1$H NMR ($CDCl_3$, 400 MHz) consistent with assigned structure.

FABLRMS m/e 345 g/mole ($M^+$+H, $C_{19}H_{28}N_4O_2$=345 g/mole.)

EXAMPLE 35

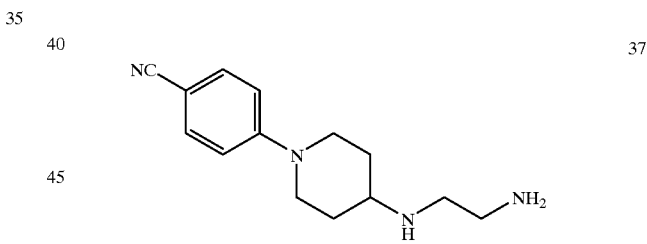

37

4-(4-(2-Aminoethylamino)piperidin-1-yl) benzonitrile (37)

Following the procedure of Example 14, but using (36) in place of (15), the title compound (37) was obtained.

FABLRMS m/e 245 g/mole ($M^+$+H, $C_{14}H_{20}N_4$=245 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=4.91 min; focus=215 nm; 94.3% pure.

EXAMPLE 36

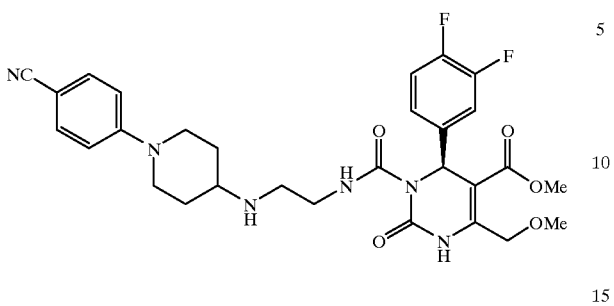

(4S)-3-(2-(1-(4-Cyanophenyl)piperidin-4-ylamino)
ethylcarbamoyl)-4-(3,4-difluorophenyl)-6-
methoxymethyl-2-oxo-1,2,3,4-tetrahydropyrimidine-
5-carboxylic acid methyl ester (38)

Following the procedure of Example 12, but using (37) in place of (13), the crude product was obtained. PCTLC (SiO$_2$, 2 mm, 10% EtOH-90% CHCl$_3$) afforded the title compound (38) as the hydrochloride salt after treatment with EtOAc/HCl.

$^1$H NMR (CDCl$_3$, 400 MHz) consistent with assigned structure.

FABLRMS m/e 583 g/mole (M$^+$+H, C$_{29}$H$_{32}$F$_2$N$_6$O$_5$=583 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=9.11 min; focus=215 um; 96.9% pure.

Anal. Calcd for C$_{29}$H$_{32}$F$_2$N$_6$O$_5$.0.95 HCl.0.60 water: C=55.45; H=5.48; N=13.38. Found: C=55.49; H=5.47; N=13.03.

EXAMPLE 37

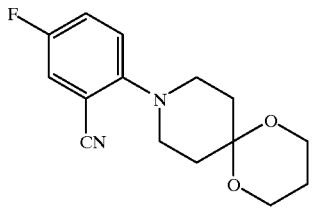

N-(2-Cyano-4-fluorophenyl)-4-piperidone propylene ketal (39)

A mixture of 2,5-difluorobenzonitrile (2.272 g, 16.33 mmol) and 4-piperidone propylene ketal (2.570 g, 16.34 mmol) was stirred at room temperature (11 d). The resulting mixture was diluted with dichloromethane and sodium carbonate solution and the aqueous layer was extracted with two additional portions of dichloromethane. The combined organic extracts were washed with brine and dried over Na$_2$SO$_4$. The solvent was removed in vacuo. PCTLC (SiO$_2$, 6 mm, 20% EtOAc-80% hexane) afforded the title compound (39).

$^1$H NMR (CDCl$_3$, 400 MHz) consistent with assigned structure.

FABLRMS m/e 277 g/mole (M$^+$+H, C$_{15}$H$_{17}$FN$_2$O$_2$=277 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=7.31 min; focus=215 nm; 99.3% pure.

EXAMPLE 38

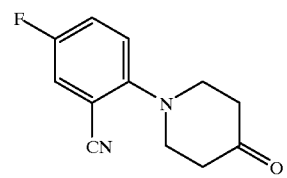

N-(2-Cyano-4-fluorophenyl)-4-piperidone (40)

A solution of 39 (1.483 g, 5.36 mmol) in 6N aqueous HCl (25 mL) was treated with acetic acid (50 mL) at room temperature. The mixture was stirred at room temperature (3 d). The solvent was removed in vacuo and the residue dissolved in dichloromethane and sodium carbonate solution. The aqueous layer was extracted with three additional portions of dichloromethane and the combined organic extracts were washed with brine, dried over Na$_2$SO$_4$, and concentrated under reduced pressure. PCTLC (SiO$_2$, 6 mm, 20% EtOAc-80% hexane) afforded the title compound (40).

$^1$H NMR (CDCl$_3$, 400 MHz) consistent with assigned structure.

FABLRMS m/e 219 g/mole (M$^+$+H, C$_{12}$H$_{11}$FN$_2$O=219 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=7.95 min; focus=215 nm; 98.2% pure.

EXAMPLE 39

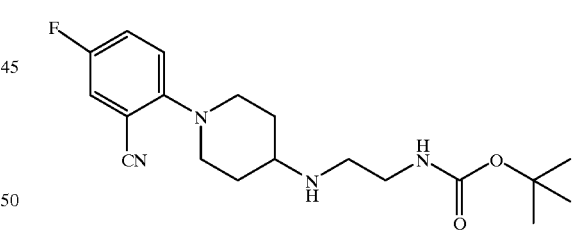

(2-(1-(2-Cyano-4-fluorophenyl)piperidin-4-ylamino)
ethyl)carbamic acid tert-butyl ester (41)

Following the procedure of Example 19, but using (40) in place of (20), the crude product was obtained. PCTLC (SiO$_2$, 4 mm, 1% NH$_4$OEt-10% EtOH-90% CHCl$_3$) afforded the title compound (41).

FABLRMS m/e 363 g/mole (M$^+$+H, C$_{19}$H$_{27}$FN$_4$O$_2$=363 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=8.37 min; focus=215 nm; 99% pure.

EXAMPLE 40

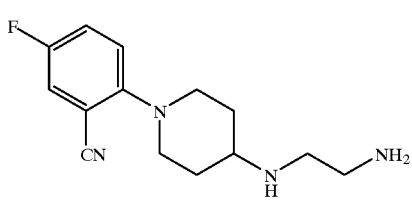

2-(4-(2-Aminoethylamino)piperidin-1-yl)-5-fluorobenzonitrile (42)

Following the procedure of Example 14, but using (41) in place of (14), the title compound (42) was obtained.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=5.84 min; focus=215 nm; 100% pure.

EXAMPLE 41

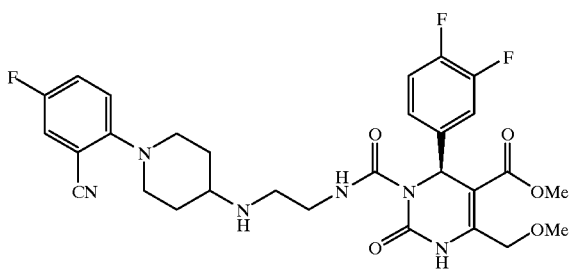

(4S)-3-(2-(1-(2-Cyano-4-fluorophenyl)-piperidin-4-ylamino)ethyl-carbamoyl)-4-(3,4-difluorophenyl)-6-methoxymethyl-2-oxo-1,2,3,4-tetrahydropyrimidine-5-carboxylic acid methyl ester (43)

Following the procedure of Example 12, but using (42) in place of (13), the crude product was obtained. PCTLC ($SiO_2$, 2 mnm, 1% $NH_4OEt$-10% EtOH-90% $CHCl_3$) afforded the title compound (43) which was converted to the hydrochloride salt after treatment with EtOAc/HCl.

$^1H$ NMR ($CDCl_3$, 400 MHz) consistent with assigned structure.

FABLRMS m/e 601 g/mole ($M^+$+H, $C_{29}H_{31}F_3N_6O_5$=601 g/mole.)

HPLC (Vydac; C18; diameter=4.6 mm; length=150 mm; gradient $H_2O$ [0.1% $H_3P_4$]—$CH_3CN$, 95%–5%, 5%–95%, over 16 minutes, 2 ml/min flow rate) RT=9.75 min; focus= 215 nm; 100% pure.

Anal. Calcd for $C_{29}H_{31}F_3N_6O_5$·1.10 HCl: C=54.36; H=5.05; N=13.12. Found: C=54.28; H=5.20; N=13.34.

EXAMPLE 42

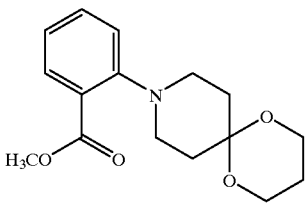

N-(2-Carbomethoxyphenyl)-4-piperidone propylene ketal (44)

A mixture of methyl 2-fluorobenzoate (16.0 g, 103.8 mmol) and 4-piperidone propylene ketal (9.8 g, 62.3 mmol) was stirred at room temperature (8 d). Flash chromatography on silica gel (10% MeOH-90% $CHCl_3$) afforded the title compound (44).

$^1H$ NMR ($CDCl_3$, 400 MHz) consistent with assigned structure.

FABLRMS m/e 292 g/mole ($M^+$+H, $C_{16}H_{21}NO_4$=292 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=4.96 min; focus=215 nm; 93.2% pure.

EXAMPLE 43

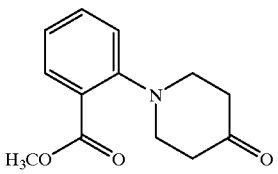

N-(2-Carbomethoxyphenyl)-4-piperidone (45)

A mixture of 44 (5.3 g, 18 mmol) in methanolic HCl (200 mL) was heated in an oil bath (50° C., 1 h). The resulting mixture was cooled, diluted with water (50 mL), and stirred at room temperature (30 min). The solvent volume was reduced in vacuo and neutralized with sodium carbonate. The aqueous layer was extracted with three portions of dichloromethane. The combined organic extracts were washed with brine and dried over $Na_2SO_4$. The solvent was removed in vacuo. PCTLC ($SiO_2$, 6 mm, 10% EtOH-90% $CHCl_3$) afforded the title compound (45).

$^1H$ NMR ($CDCl_3$, 400 MHz) consistent with assigned structure.

EXAMPLE 44

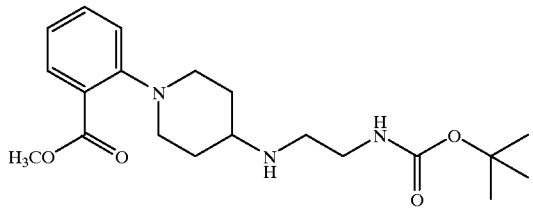

2-(4-(2-tert-Butoxycarbonylaminoethylamino)
piperidin-1-yl)benzoic acid methyl ester (46)

A solution of 45 (195 mg, 0.836 mmol), 1 (175 mg, 1.09 mmol), and acetic acid (251 mg, 4.19 mmol) in methanol (3 mL)/dichloroethane (1 mL) was treated with sodium cyanoborohydride (55 mg, 0.875 mmol) at room temperature. The resulting mixture was stirred at room temperature (3 h). The solvent was removed in vacuo and the residue dissolved in dichloromethane and sodium carbonate solution. The aqueous layer was extracted with two additional portions of dichloromethane and the combined organic extracts were washed with brine, dried over $Na_2SO_4$, and concentrated under reduced pressure. PCTLC ($SiO_2$, 4 mm, 1% $NH_4OEt$-10% EtOH-90% $CHCl_3$) afforded the title compound (46).

$^1$H NMR ($CDCl_3$, 400 MHz) consistent with assigned structure.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=6.61 min; focus=215 nm; 94.2% pure.

EXAMPLE 45

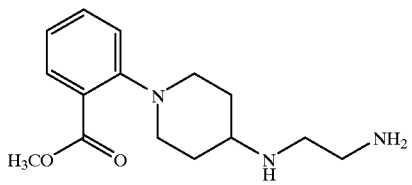

2-(4-(2-Aminoethylamino)piperidin-1-yl)benzoic
acid methyl ester (47)

Following the procedure of Example 14, but using (46) in place of (15), the title compound (47) was obtained.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=4.64 min; focus=215 nm; 92.4% pure.

EXAMPLE 46

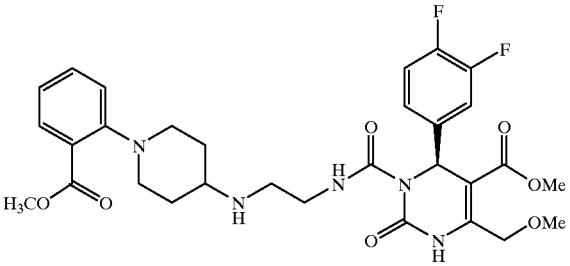

(4S)-4-(3,4-Difluorophenyl)-3-(2-(1-(2-
methoxycarbonylphenyl)piperidin-4-ylamino)
ethylcarbamoyl)-6-methoxymethyl-2-oxo-1,2,3,4-
tetrahydropyrimidine-5-carboxylic acid methyl ester
(48)

A solution of 2 (75 mg, 0.157 mmol) in dichloromethane (1 mL) was treated with a solution of 47 (43 mg, 0.155 mmol) in dichloromethane (1 mL) at room temperature. The mixture was stirred at room temperature overnight. The mixture was diluted with sodium carbonate solution and the aqueous layer was extracted with two additional portions of dichloromethane. The combined organic extracts were washed with brine and dried over $Na_2SO_4$. The solvent was removed in vacuo. PCTLC ($SiO_2$, 2 mm, 1% $NH_4OEt$-10% EtOH-90% $CHCl_3$) afforded the title compound (48) which was converted to the hydrochloride salt after treatment with EtOAc/HCl.

$^1$H NMR ($CDCl_3$, 400 MHz) consistent with assigned structure.

FABLRMS m/e 616 g/mole ($M^+$+H, $C_{30}H_{35}F_2N_5O_7$=616 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=8.66 min; focus=215 nm; 97.1% pure.

EXAMPLE 47

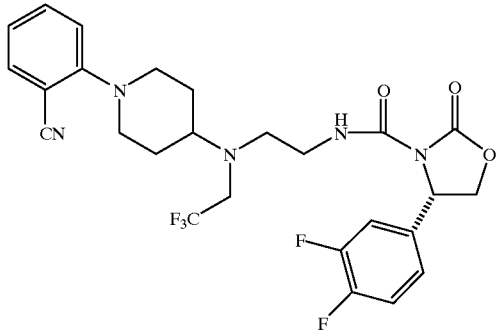

(4S)-4-(3,4-Difluorophenyl)-2-oxo-oxazolidine-3-
carboxylic acid (2-((1-(2-cyanophenyl)piperidin-4-
yl)-(2,2,2-trifluoroethyl)amino)ethyl)amide (49)

A solution of 18 (36 mg, 0.076 mmol) and cesium carbonate (50 mg, 0.153 mmol) in acetonitrile (100 mL) was treated with 2,2,2-trifluoroethyliodide (21.3 mg, 0.101 mmol) at room temperature. The resulting mixture was stirred at room temperature overnight. The mixture was diluted with dichloromethane and water and the aqueous layer was extracted with two additional portions of dichloromethane. The combined organic extracts were concentrated under reduced pressure and purified by PCTLC (SiO$_2$, 4 mm, 1% NH$_4$OEt-1% NH$_4$OEt-10% EtOH-90% CHCl$_3$) to afford the title compound (49) which was converted to the hydrochloride salt after treatment with EtOAc/HCl.

$^1$H NMR (CDCl$_3$, 400 MHz) consistent with assigned structure.

FABLRMS m/e 553 g/mole (M$^+$+H, C$_{26}$H$_{26}$F$_5$N$_5$O$_3$=553 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=7.95 min; focus=215 nm; 92.3% pure.

EXAMPLE 48

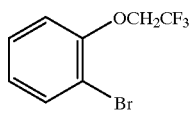

1-Bromo-2-(2,2,2-trifluoroethoxy)benzene (50)

A solution of 2-bromophenol (5.89 g, 34.0 mmol) and 2,2,2-trifluoroethyliodide (16.8 g, 80.0 mmol) in DMF (60 mL) was treated with potassium carbonate (24.1 g, 174 mmol) at room temperature. The resulting mixture was heated in an oil bath (60° C., 2 d). The solvent was removed in vacuo and the residue dissolved in ether and water. The aqueous layer was extracted with two additional portions of ether and the combined organic extracts were washed with three portions of 1M NaOH solution and dried over Na$_2$SO$_4$. The solvent was removed in vacuo to afford the title compound (50).

$^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=11.42 min; focus=215 nm; 93.2% pure.

EXAMPLE 49

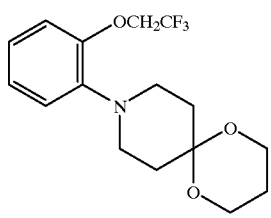

N-(2-(2,2,2-Trifluoroethoxy)phenyl)-4-piperidone propylene ketal (51)

A solution of 50 (1.786 g, 7.00 mmol) and 4-piperidone propylene ketal (2.645 g, 16.82 mmol) in toluene (30 mL) was treated with sodium tert-butoxide (1.88 g, 19.56 mmol), (S)-BINAP (44 mg, 0.07 mmol), and tris (dibenzylideneacetone)dipalladium(0) (32 mg, 0.035 mmol) at room temperature. The mixture was heated in an oil bath (80° C., 3 h). The mixture was diluted with ether and brine. The aqueous layer was extracted with two additional portions of ether and the combined organic extracts were washed with brine, dried over Na$_2$SO$_4$, and concentrated under reduced pressure. PCTLC (SiO$_2$, 6 mm, 20% EtOAc-80% hexane) afforded the title compound (51).

$^1$H NMR (CDCl$_3$, 400 MHz) consistent with assigned structure.

FABLRMS Sie 332 g/mole (M$^+$+H, C$_{16}$H$_{20}$F$_3$NO$_3$=332 g/mole.)

EXAMPLE 50

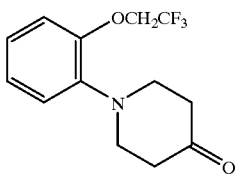

N-(o-(2,2,2-Trifluoroethoxy)phenyl)-4-piperidone (52)

A solution of 51 (410 mg, 1.23 mmol) in acetic acid (20 mL), water (20 ml), and concetrated HCl (5 mL) was heated in an oil bath (60° C.) overnight. The solvent was removed in vacuo and the residue dissolved in dichloromethane and sodium bicarbonate solution. The aqueous layer was extracted with two additional portions of dichloromethane and the combined organic extracts were washed with brine, dried over Na$_2$SO$_4$, and concentrated under reduced pressure. PCTLC (SiO$_2$, 4 mm, 10% EtOH-90% CHCl$_3$) afforded the title compound (52)

$^1$H NMR (CDCl$_3$, 400 MHz) consistent with assigned structure.

EXAMPLE 51

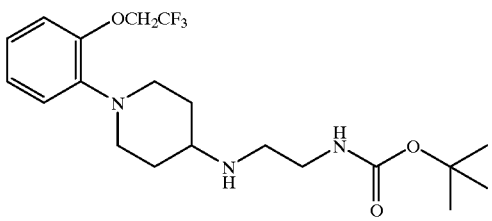

(2-(1-(2-(2,2,2-Trifluoroethoxy)phenyl)piperidin-4-ylamino)ethyl)-carbamic acid tert-butyl ester (53)

Following the procedure of Example 19, but using (52) in place of (20), the crude product was obtained. PCTLC (SiO$_2$, 4 mm, 1% NH$_4$OEt-10% EtOH-90% CHCl$_3$) afforded the title compound (53).

$^1$H NMR (CDCl$_3$, 400 MHz) consistent with assigned structure.

FABLRMS m/e 418 g/mole (M$^+$+H, C$_{20}$H$_{30}$F$_3$N$_3$O$_3$=418 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=8.04 min; focus=215 nm; 97.4% pure.

EXAMPLE 52

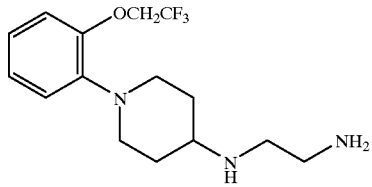

N₁-(1-(2-(2,2,2-Trifluoroethoxy)phenyl)piperidin-4-yl)ethane-1,2-diamine (54)

Following the procedure of Example 14, but using (53) in place of (15), the title compound (54) was obtained.

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=5.84 min; focus=215 nm; 100% pure.

EXAMPLE 53

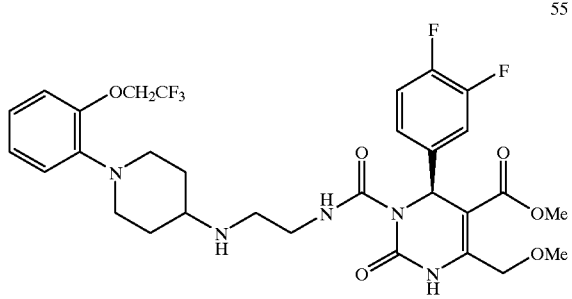

(4S)-4-(3,4-Difluorophenyl)-6-methoxymethyl-2-oxo-3-(2-(1-(2-(2,2,2-trifluoroethoxy)phenyl)piperidin-4-ylamino)ethylcarbamoyl)-1,2,3,4-tetrahydropyrimidine-5-carboxylic acid methyl ester (55)

A solution of 54 (74 mg, 0.233 mmol) in dichloromethane (1 nmL) was treated with 2 (122 mg, 0.255 mmol) at room temperature. The mixture was stirred at room temperature (5 min). The mixture was diluted with sodium carbonate solution and the aqueous layer was extracted with two additional portions of dichloromethane. The combined organic extracts were washed with brine and dried over Na₂SO₄. The solvent was removed in vacuo. PCTLC (SiO₂, 2 mm, 1% NH₄OEt-10% EtOH-90% CHCl₃) afforded the title compound (55) as the hydrochloride salt after treatment with EtOAc/HCl.

¹H NMR (CDCl₃, 400 MHz) consistent with assigned structure.

FABLRMS m/e 656 g/mole (M⁺+H, C₃₀H₃₄F₅N₅O₆=656 g/mole.)

HPLC (Vydac; C18; diameter=4.6 mm; length=150 mm,; gradient=H₂O [0.1% H₃PO₄]—CH₃CN, 95%–5%, 5%–95%, over 16 minutes, 2 ml/min flow rate) RT=9.86 min; focus=215 nm; 100% pure.

EXAMPLE 54

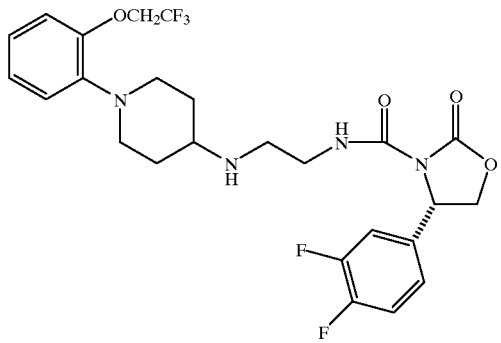

(4S)-4-(3,4-Difluorophenyl)-2-oxo-oxazohdine-3-carboxylic acid (2-(1-(2-(2,2,2-trifluoroethoxy)phenyl)piperidin-4-ylamino)ethyl)amide (56)

A solution of 54 (94 mg, 0.296 mmol) in dichloromethane (1 mL) was treated with 3 (109 mg, 0.299 mmol) at room temperature. The mixture was stirred at room temperature (20 min). The mixture was diluted with sodium carbonate solution and the aqueous layer was extracted with two additional portions of dichmoromethane. The combined organic extracts were washed with brine and dried over Na₂SO₄. The solvent was removed in vacuo PCTLC (SiO₂, 2 mm, 1% NH₄OEt-10% EtOH-90% CHCl₃) afforded the title compound (56) which was converted to the hydrochloride salt after treatment with EtOAc/HCl.

¹H NMR (CDCl₃, 400 MHz) consistent with assigned structure.

FABLRMS m/e 543 g/mole (M⁺+H, C₂₅H₂₇F₅N₄O₄=543 g/mole.)

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=8.81 min; focus=215 nm; 99.2% pure.

Anal. Calcd for C₂₅H₂₇F₅N₄O₄.0.75 HCl.1.80 water: C=49.85; H=5.25; N=9.30. Found: C=49.85; H=5.25; N=8.91.

EXAMPLE 55

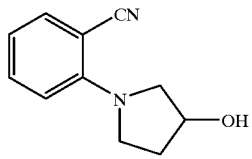

N-(2-Cyanophenyl)-pyrolidin-2-ol (57)

A mixture of 2-fluorobenzonitrile (4.03 g, 33.2 mmol) and pyrolidin-2-ol (2.92 g, 33.5 mmol) was treated with diisopropylethylamine (4.37 g, 33.8 mmol) at room temperature. The mixture was stirred at room temperature (5 d). The resulting mixture was diluted with dichloromethane and sodium carbonate solution and the aqueous layer was extracted with two additional portions of dichloromethane. The combined organic extracts were washed with brine and dried over Na₂SO₄. The solvent was removed in vacuo. PCTLC (SiO₂, 6 mm, 20% EtOAc-80% hexane) afforded the title compound (57).

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=7.18 min; focus=215 nm; 98.9% pure.

EXAMPLE 56

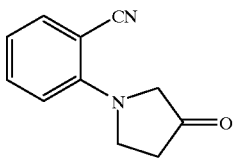

N-(2-Cyanophenyl)-2-pyrrolidinone (68)

A solution of oxalyl chloride (1.58 g, 12.46 mmol) in dichloromethane (50 mL) was treated with DMSO (1.95 g, 24.94 mmol) at −78° C. The mixture was stirred at +78° C. (10 min) followed by addition of a solution of 57 (2.34 g, 12.43 mmol) in dichloromethane (20 mL) over 10 min. The mixture was stirred at −78° C. (30 min) followed by addition of a triethylamine (4.28 g, 42.33 mmol) over 5 min. The mixture was warmed to room temperature and diluted with water (20 mL). The organic extract was washed with brine and dried over Na₂SO₄. The solvent was removed in vacuo. PCTLC (SiO₂, 6 mm, 10% EtOH-90% CHCl₃) afforded the title compound (58).

¹H NMR (CDCl₃, 400 MHz) consistent with assigned structure.

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=7.70 min; focus=215 nm; 99.1% pure.

EXAMPLE 57

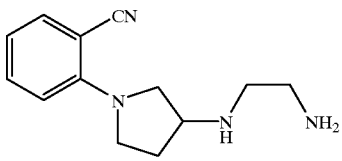

2-(3-(2-Aminoethylamino)pyrrolidin-1-yl) benzonitrile (59)

A solution of 58 (1.33 g, 7.13 mmol), ethylenediamine (4.44 g, 73.9 mmol), and p-tolylsulfonic acid (75 mg, 0.394 mmol) in benzene (80 mL) was refluxed (1 h) with removal of water. The solvent was removed in vacuo and the residue dissolved in methanol (40 mL) and treated with sodium cyanoborohydride (480 mg, 7.64 mmol). The mixture was stirred at room temperature overnight. The solvent was removed in vacuo and the residue dissolved in dichloromethane and sodium carbonate solution. The aqueous layer was extracted with two additional portions of dichloromethane and the combined organic extracts were washed with brine, dried over Na₂SO₄, and concentrated under reduced pressure. PCTLC (SiO₂, 6 mm, 1% NH₄OEt-10% EtOH-90% CHCl₃) afforded the title compound (59)

FABLRMS m/e 231 g/mole (M⁺+H, $C_{13}H_{18}N_4$=231 g/mole.)

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=5.27 min; focus=215 nm; 98.7% pure.

EXAMPLE 58

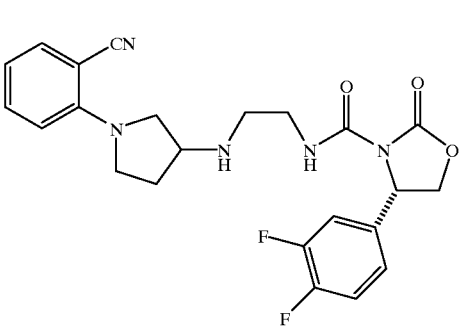

(4S)-4-(3,4-Difluorophenyl)-2-oxo-oxazolidine-3-carboxylic acid (2-(1-(2-cyanophenyl)pyrrolidin-3-ylamino)ethyl)amide (60)

A solution of 59 (115 mg, 0.499 mmol) in dichloromethane (2 mL) was treated with 3 (164 mg, 0.450 mmol) at room temperature. The mixture was stirred at room temperature (1 h). The mixture was diluted with sodium carbonate solution and the aqueous layer was extracted with two additional portions of dichloromethane. The combined organic extracts were washed with brine and dried over Na₂SO₄. The solvent was removed in vacuo. PCTLC (SiO₂, 2 mm, 1% NH₄OEt-10% EtOH-90% CHCl₃) afforded the title compound (60) which was converted to the hydrochloride salt after treatment with EtOAc/HCl.

¹H NMR (CDCl₃, 400 MHz) consistent with assigned structure.

FABLRMS m/e 456 g/mole (M⁺+H, $C_{23}H_{23}F_2N_5O_3$=456 g/mole.)

HPLC (Vydac; C18; diameter=4.6 mm; length=150 mm; gradient=H₂O [0.1% H₃PO₄]—CH₃CN, 95%–5%, 5%–95%, over 16 minutes, 2 ml/min flow rate) RT=8.69 min; focus=215 nm; 100% pure.

Anal. Calcd for $C_{23}H_{23}F_2N_5O_3$.0.70 HCl.0.90 water: C=55.56; H=5.17; N=14.09. Found: C=55.52; H=5.16; N=13.72.

EXAMPLE 59

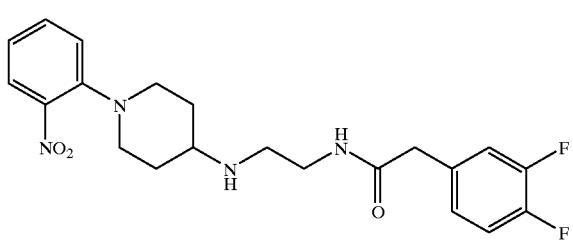

2-(3,4-Difluorophenyl)-N-(2-(1-(2-nitrophenyl) piperidin-4-ylamino)ethyl)acetamide (61)

A solution of N-(2-nitrophenyl)piperid-4-one (128.7 mg, 0.5844 mmol), N-(2-aminoethyl)-1-(3,4-difluorophenyl)

acetamide (125.2 mg, 0.5844 mmol), and acetic acid (175 mg, 2.922 mmol) in methanol (2 mL) was treated with sodium cyanoborohydride (37 mg, 0.5844 mmol) at room temperature. The resulting mixture was stirred at room temperature (50 min). The solvent was removed in vacuo and the residue dissolved in dichloromethane and sodium bicarbonate solution. The aqueous layer was extracted with two additional portions of dichloromethane and the combined organic extracts were washed with brine, dried over $Na_2SO_4$, and concentrated under reduced pressure. PCTLC ($SiO_2$, 2 mm, 0–5% MeOH—$CHCl_3$) afforded the title compound (61).

$^1$H NMR ($CDCl_3$, 400 MHz) consistent with assigned structure.

FABLRMS m/e 419.22 g/mole ($M^++H$, $C_{21}H_{24}N_4O_3F_2=$ 419.45 g/mole.)

Anal. Calcd for $C_{21}H_{24}N_4O_3F_2.2$ HCl & 0.45 $H_2O$: C=50.49; H=5.43; N=11.22. Found: C=50.52; H=5.37; N=11.04.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=8.19 min; focus=215 nm; 98.7% pure.

EXAMPLE 60

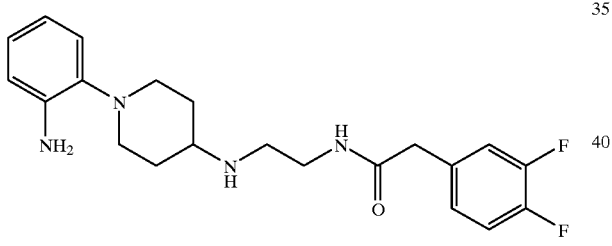

62

N-(2-(1-(2-Aminophenyl)piperidin-4-ylamnino) ethyl)-2-(3,4-difluorophenyl)acetamide (62)

A solution of nitroaryl (75 mg, 0.1801 mmol) and 10% Pd-C (50 mg) in THF (10 nmL) was stirred at room temperature under a hydrogen atmosphere (2 h). The resulting mixture was filtered through Celite, washed with EtOH and concentrated under reduced pressure affording the title compound (62).

$^1$H NMR ($CDCl_3$, 400 MHz) consistent with assigned structure.

FABLRMS m/e 389.19 g/mole ($M^++H$, $C_{21}H_{26}N_4OF_2=$ 389.46 g/mole.)

Anal. Calcd for $C_{21}H_{26}N_4O_3F_2.3$ HCl: C=50.66; H=5.87; N=11.25. Found: C=50.91; H=6.15; N=11.29.

EXAMPLE 61

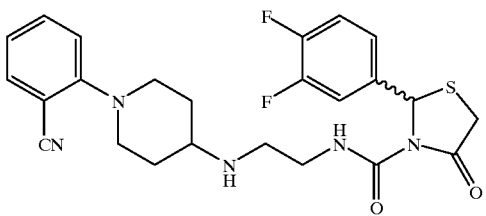

63

2-(3,4-Difluorophenyl)-4-oxothiazolidine-3-carboxylic acid (2-(1-(2-cyanophenyl)piperidin-4-ylamino)ethyl)amide (63)

A solution of amine (60 mg, 0.2456 mmol) in DMF (1 mL) was treated with a solution of the activated thiazolidinone (0.2456 mmol) in dichloromethane (1 mL) at room temperature (1 h). The resulting yellow reaction mixture was concentrated in vacuo and submitted to PCTLC ($SiO_2$, 1 cm, 0–10% MeOH-$CHCl_3$) providing the desired product 63).

$^1$H NMR ($CDCl_3$, 400 MHz) consistent with assigned structure.

Anal. Calcd for $C_{24}H_{25}N_5O_2SF_2.0.4$ DMF: C=58.79; H=5.44; N=14.69. Found: C=58.93; H=5.07; N=15.09.

EXAMPLE 62

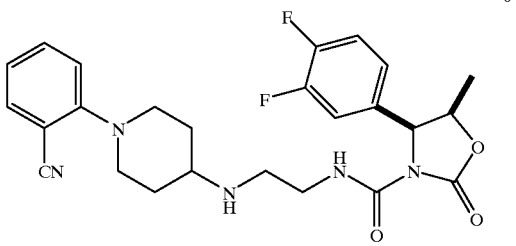

64

(4S,5R)-4-(3,4-difluorophenyl)-5-methyl-2-oxo-oxazolidine-3-carboxylic acid (2-(1-(2-cyanophenyl) piperidin-4-ylamino)ethyl)amide (64)

A solution of amine (19.4 mg, 0.0793 mmol) in $CHCl_3$ (1 mL) was treated with a solution of the activated oxazolidinone (0.0793 mmol) in DCM (1 mL) at room temperature. The mixture was stirred at room temperature (1 h). The resulting yellow reaction mixture was concentrated in vacuo and submitted to PCTLC ($SiO_2$, 1 cm, 0–10% MeOH-$CHCl_3$) providing the desired product (64).

$^1$H NMR ($CDCl_3$, 400 MHz) consistent with assigned structure.

Anal. Caled for $C_{25}H_{27}N_5O_3F_2.0.4$ $CHCl_3$: C=57.42; H=5.20; N=13.18. Found: C=57.27; H=5.49; N=13.51.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=9.10 (cis) and 9.31 (trans) min; focus=215 nm; 95.5:4.5 pure.

EXAMPLE 63

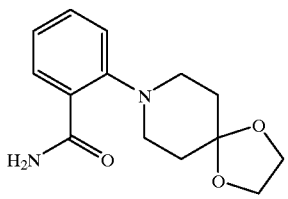

N-(2Benzamido)-4-piperidone ethylene ketal (65)

A mixture of 2-fluorobenzamide (7.0 g, 50.0 mmol) and 4-piperidone ethylene ketal (7.16 g, 50.0 mmol) was heated at 100° C. (7 d). The solvent was removed in vacuo and triturated with ether affording the title compound (65).

$^1$H NMR (DMSO-$d_6$, 300 MHz) consistent with assigned structure.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=4.49 min; focus=215 nm; 100% pure.

EXAMPLE 64

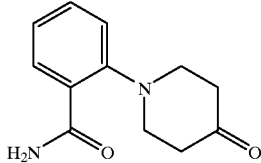

N-(2-Benzamido)-4-piperidone (66)

A solution of the ketal (13.2 mg, 46.753 mmol) in acetic acid (50 mL) and 6N aqueous HCl (50 mL) was heated at 60° C. (12 h), 80% conversion. The solvent was removed in vacuo, neutralized with 25% aqueous NaOH, extracted with $CHCl_3$ (3×250 mL), the combined organic extracts were washed with brine, dried over $Na_2SO_4$, and concentrated under reduced pressure to give (66) which was used without further purification.

$^1$H NMR (CDCl$_3$, 400 MHz) consistent with assigned structure.

EXAMPLE 65

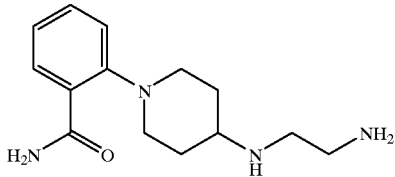

2-(4-(2-Aminoethylamino)piperidin-1-yl)benzamide (67)

A solution of the piperidone (2.5 g, 11.4543 mmol), ethylene diamine (6.89 g, 114.543 mmol) and p-toluene sulphonic acid (0.105 g, 0.57272 mmol) in benzene (100 mL) was refluxed under a Dean-Stark trap until cessation of water azeotrope. The solvent was removed in vacuo, diluted with MeOH (50 mL) and treated with NaBH$_3$CN (0.714 g, 11.4543 mmol) at room temperature (1 h). The solvent was removed in vacuo, diluted with DCM (50 mL) and saturated aqueous sodium bicarbonate (25 mL), partitioned, extracted with DCM (2×50 mL), washed with saturated aqueous sodium bicarbonate (2×25 mL) and brine (50 mL), dried (Na$_2$SO$_4$), filtered and concentrated in vacuo and submitted to PCTLC (SiO$_2$, 6 mm, 80/20/2 CHCl$_3$—MeOH—NH$_4$OH) affording the titled amine (67).

$^1$H NMR (CDCl$_3$, 400 MHz) 9.60 (br s, 1 H), 8.16 (dd, 1 H), 7.45 (dd, 1 H), 7.22 (m, 2 H), 5.87 (br s, 1 H), 3.20 (br d, 2 H), 2.70–2.90 (m, 6 H), 2.65 (m, 1 H), 2.07 (br d, 2 H). 1.56 (br ddd, 2 H).

EXAMPLE 66

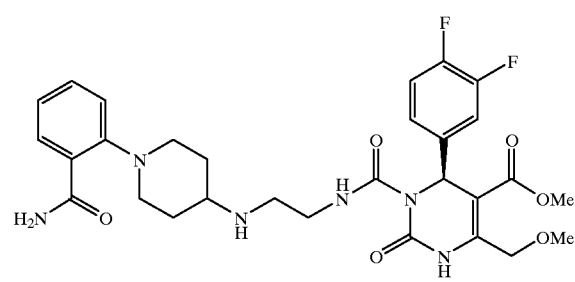

(4S)-3-(2-(1-(2-Carbamoylphenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester (68)

The amine (55 mg, 0.21 mmol) was dissolved in THF and treated with 2 (100 mg, 0.21). The resulting yellow reaction mixture was concentrated in vacuo and submitted to PCTLC (SiO$_2$, 2 mm, CHCl$_3$-90/10/1 CHCl$_3$—MeOH—NH$_4$OH) providing the desired product (68) and a minor less polar material.

$^1$H NMR (CDCl$_3$, 400 MHz) consistent with assigned structure.

Anal. Calcd for $C_{29}H_{34}N_6O_6F_2$.0.1 hexane & 1.25 H$_2$O: C=56.27, H=6.05, N=13.30. Found: C=56.54, H=5.65, N=12.91.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) RT=7.83 min; focus=215 nm; 98.8% pure.

EXAMPLE 67

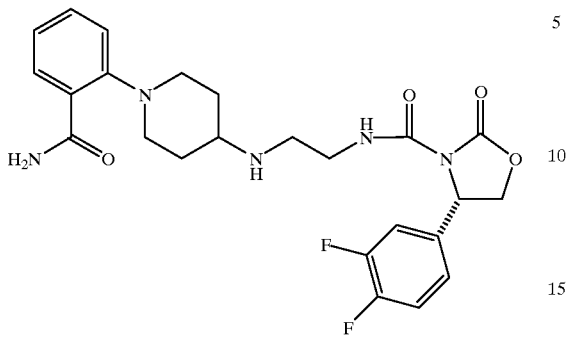

(4S)-4-(3,4-Difluorophenyl)-2-oxo-oxazolidine-3-carboxylic acid (2-(1-(2-carbamoylphenyl)piperidin-4-ylamino)ethyl)amide (69)

A solution of the amine (72 mg, 0.2745 mmol) in THF (1 mL) was treated with the activated (S)-oxazolidinone (100 mg, 0.2745 mmol) at room temperature. The resulting yellow reaction mixture was concentrated in vacuo and submitted to PCTLC (SiO$_2$, 2 mm, CHCl$_3$-90/10/1 CHCl$_3$—MeOH—NH$_4$OH) providing the desired product (69).

$^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=6.72 min; focus=215 nm; 99.2% pure.

Anal. Calcd for C$_{24}$H$_{27}$F$_2$N$_5$O$_4$.2.0 HCl.1.65 water: C=48.84, H=5.52, N=11.87 Found: C=48.87, H=5.64, N=11.99.

EXAMPLE 68

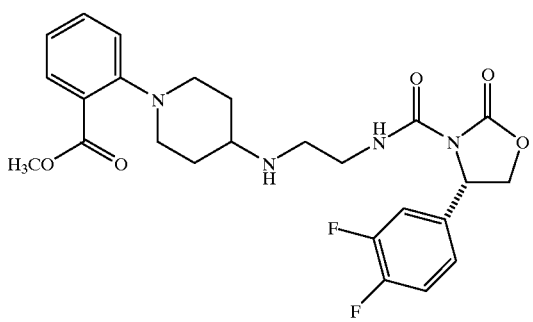

(4S)-4-(3,4-Difluorophenyl)-2-oxo-oxazolidine-3-carboxylic acid (2-(1-(4-fluoro-2-methoxycarbonylphenyl)piperidin-4-ylamino)ethyl) amide (70)

Following the methodology described herein, compound 70 was prepared.

$^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=7.4 min; focus=215 nm; 99.2% pure.

Anal. Calcd for C$_{25}$H$_{27}$F$_3$N$_4$O$_5$.2.0 HCl.0.35 water: C=50.06, H=4.99, N=9.34 Found: C=50.06, H=4.96, N=9.27.

EXAMPLE 69

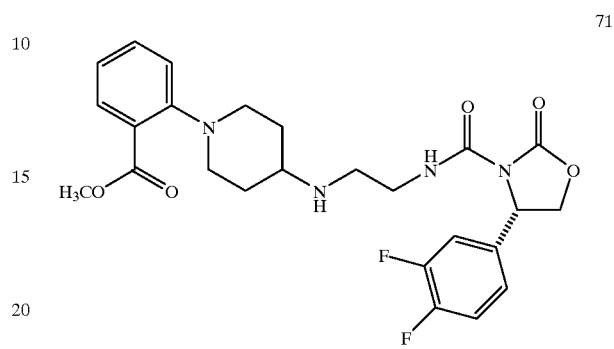

(4S)-4-(3,4-Difluorophenyl)-2-oxo-oxazolidine-3-carboxylic acid (2-(1-(2-methoxycarbonylphenyl)piperidin-4-ylamino)ethyl)amide (71)

Following the procedure of Example 16, but using (47) in place of (13), the title compound (71) was obtained.

$^1$H NMR (CDCl$_3$, 400 MHz) consistent with assigned structure.

FABLRMS m/e 503 g/mole (M$^+$+H, C$_{25}$H$_{28}$F$_2$N$_4$O$_5$=503 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) RT=7.8 min; focus=215 nm; 99.2% pure.

Anal. Calcd for C$_{25}$H$_{28}$F$_2$N$_4$O$_5$.1.95 HCl: C=52.34, H=5.26, N=9.77 Found: C=52.33, H=5.16, N=9.63.

EXAMPLE 70

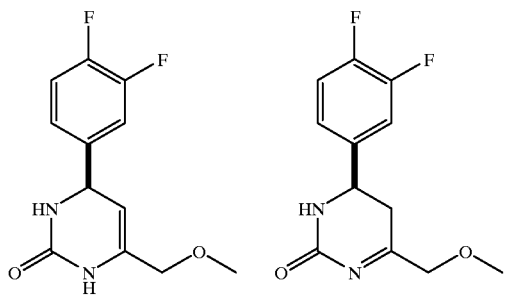

Mixture of (4S)-4-(3,4-difluorophenyl)-6-methoxymethyl-2-oxo-1,2,3,4-tetrahydropyrimidine and (S-4)-(3,4-difluorophenyl)-6-methoxymethyl-2-oxo-2,3,4,5-tetrahydropyrimidine To a solution of (+)-4-(3,4-difluorophenyl)-6-methoxymethyl-2-oxo-1,2,3,4-tetrahydropyrimidine-5-carboxylic acid methyl ester (4.63 g, 14.7 mmol) in a methanol (100 ml) was added sodium hydroxide (2.94 g, 73.6 mmol). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $Na_2SO_4$, concentrated, and purified by PCTLC (7% MeOH in $CHCl_3$ with 2% $NH_4OH$) to afford a 2.65 g mixture of the title compounds (71% yield). The $^1H$ NMR was consistent with the assigned structure.

MS (FAB) 255 (M+1)

EXAMPLE 71

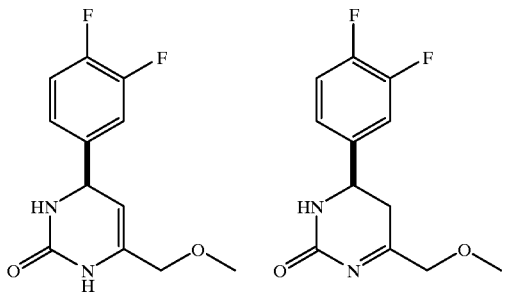

Mixture of (4S)-4-(3,4-difluorophenyl)-6-methoxymethyl-2-oxo-1,2,3,4-tetrahydropyrimidine and (4S)-4-(3,4-difluorophenyl)-6-methoxymethyl-2-oxo-2,3,4,5-tetrahydropyrimidine To a solution of (+)-4-(3,4-difluorophenyl)-6-methoxymethyl-2-oxo-1,2,3,4-tetrahydropyrimidine-5-carboxylic acid methyl ester (5.36 g, 17.0 mmol) in a methanol (150 ml) was added 1N NaOH (10 ml). The resulting mixture was refluxed at 90° C. for 16 hours. After cooling to room temperature the solvent was removed in vacuo. The solid was dissolved in $CH_2Cl_2$ and $H_2O$ then neutralized with 10% aqueous HCl solution. The organic layer was dried over $Na_2SO_4$, concentrated, and purified by PCTLC (7% MeOH in $CHCl_3$ with 2% $NH_4OH$) to afford a 2.35 g mixture of the title compounds (54% yield). The $^1H$ NMR was consistent with the assigned structure.

MS (FAB) 255 (M+1)

EXAMPLE 72

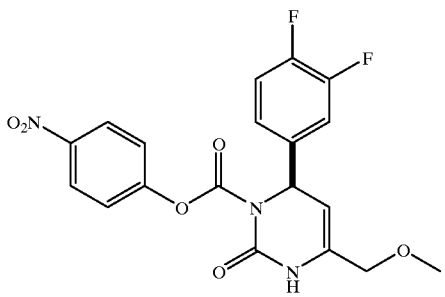

(4S)-4-(3,4-Difluorophenyl)-6-methoxymethyl-3-(4-nitrophenoxycarbonyl)-2-oxo-1,2,3,4-tetrahydropyrimidine-5-carboxylic acid methyl ester The title compound was prepared by treating the mixture obtained from Example 70 or Example 71 (1.93 g, 7.59 mmol) with lithium diisopropylamide (2.0M THF solution, 1.1 equivalents) in THF at −78° C. for 20 minutes followed by the rapid addition of 4-nitrophenyl chloroformate (1.5 equivalents) in THF. 0.488 g of the title compound was obtained in a 15% yield. The $^1H$ NMR was consistent with the assigned structure.

EXAMPLE 73

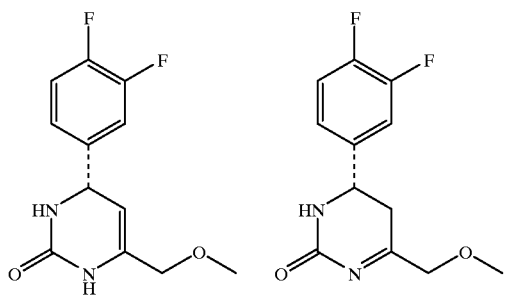

Mixture of (4R)-4-(3,4-difluorophenyl)-6-methoxymethyl-2-oxo-1,2,3,4-tetrahydropyrimidine and (4R)-4-(3,4-difluorophenyl)-6-methoxymethyl-2-oxo-2,3,4,5-tetrahydropyrimidine The title compounds were prepared from (4R)-4-(3,4-difluorophenyl)-6-methoxymethyl-2-oxo-1,2,3,4-tetrahydropyrimidine-5-carboxylic acid methyl ester (5.0 g, 17.7 mmol) using the procedure described in Example 70. A mixture of 2.0 g of the title compounds was obtained in 50% yield. The $^1H$ NMR was consistent with the assigned structure.

MS (FAB) 255 (M+1)

Compounds of the invention can be prepared by reacting the product obtained in Example 72 with a 1-aryl-4-(2-aminoethylamino)piperidine (e.g., compound 42 of Example 40) in accordance with Scheme 2. Compounds of the invention can also be prepared by preparing the nitrophenoxy derivative of the compound of Example 73 in accordance with the procedure set forth in Example 72 and then reacting the derivative with a 1-aryl-4-(2-aminoethylamino)piperidine in accordance with Scheme 2.

The following compounds were prepared in accordance with procedures set forth in the preceding Examples and Schemes.

EXAMPLE 74

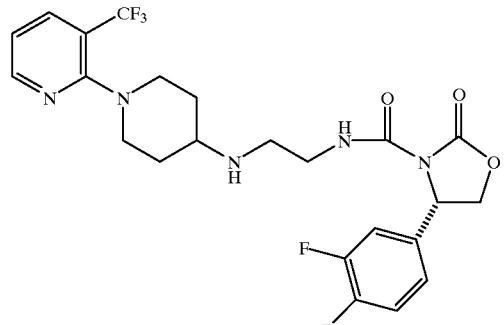

(4S)-4-(3,4-Difluorophenyl)-2-oxo-oxazolidine-3-carboxylic acid (2-(2-(3-trifluoromethylpyridyl)piperidin-4-ylamino)ethyl)amide $^1H$ NMR ($CDCl_3$, 400 MHz) consistent with assigned structure.

FABLRMS m/e 514 g/mole (M⁺+H, $C_{23}H_{24}F_5N_5O_3$=513 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) focus=215 nm; >95% pure.

Anal. Calcd for $C_{23}H_{24}F_5N_5O_3$.1.55 TFA.0.40 $H_2O$: C=44.89, H=3.82, N=10.03. Found: C=44.90, H=3.79, N=10.01.

EXAMPLE 75

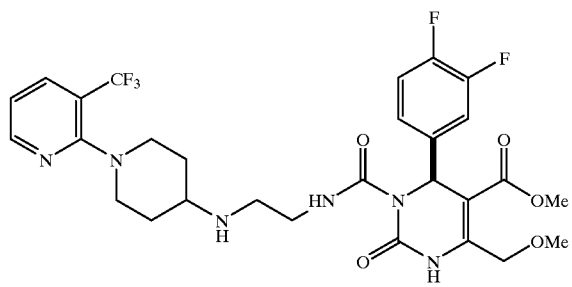

(4S)-4-(3,4-Difluorophenyl)-6-methoxymethyl-2-oxo-3-(2-(2-(3-trifluoromethylpyridyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 627 g/mole (M⁺+H, $C_{28}H_{31}F_5N_6O_5$=626 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) focus=215 nm; >95% pure.

Anal. Calcd for $C_{28}H_{31}F_5N_6O_5$.1.55 TFA.0.30 $H_2O$: C=46.19, H=4.13, N=10.39. Found: C=46.18, H=4.05, N=10.50.

EXAMPLE 76

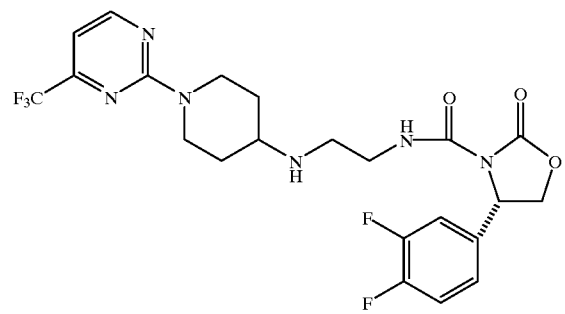

(4S)-4-(3,4-Difluorophenyl)-2-oxo-oxazolidine-3-carboxylic acid (2-(2-(4-trifluoromethylpyrimidyl)piperidin-4-ylamino)ethyl)amide $^1$H NMR (CDCl$_3$, 400 MHz) consistent with assigned structure.

FABLRMS m/e 515 g/mole (M⁺+H, $C_{22}H_{23}F_5N_6O_3$=514 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) focus=215 nm; >98% pure.

Anal. Calcd for $C_{22}H_{23}F_5N_6O_3$: C=51.36, H=4.51, N=16.34. Found: C=51.37, H=4.45, N=16.29.

EXAMPLE 77

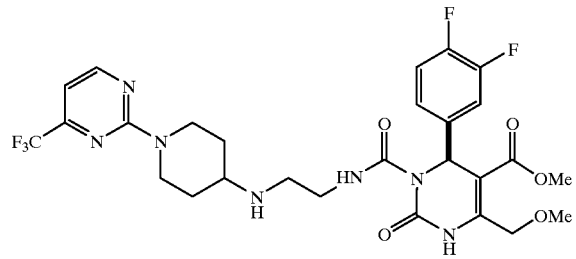

(4S)-4-(3,4-Difluorophenyl)-6-methoxymethyl-2-oxo-3-(2-(2-(4-trifluoromethylpyrimidinyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 628 g/mole (M⁺+H, $C_{27}H_{29}F_5N_6O_5$=627 g/mole.)

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) focus=215 nm; >95% pure.

Anal. Calcd for $C_{27}H_{29}F_5N_6O$.0.05 CHCl$_3$: C=51.36, H=4.63, N=15.50. Found: C=51.13, H=4.63, N=15.81.

EXAMPLE 78

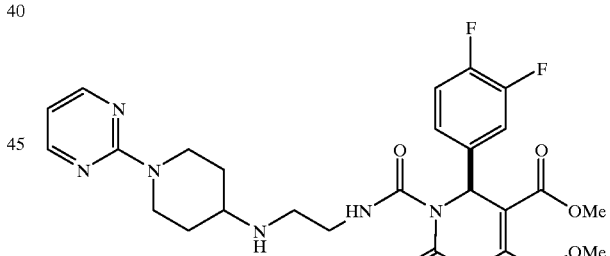

(4S)-4-(3,4-Difluorophenyl)-6-methoxymethyl-2-oxo-3-(2-(2-pyrimidinylpiperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=$H_2O$ [0.1% $H_3PO_4$]—$CH_3CN$, 95%–5%, 5%–95%, over 16 minutes, 2 ml/min flow rate) focus=215 nm; 100% pure.

Anal. Calcd for $C_{26}H_{31}F_2N_7O_5$.1.0 $H_2O$: C=54.06, H=5.76, N=16.98. Found: C=54.07, H=5.53, N=16.82.

EXAMPLE 79

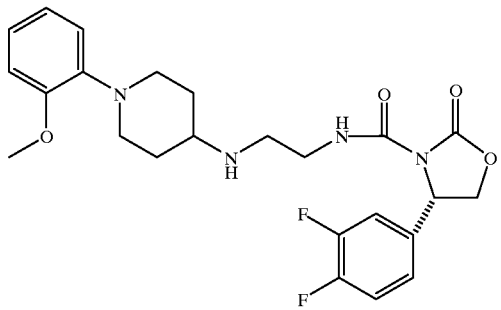

(4S)-4-(3,4-Difluorophenyl)-2-oxo-oxazolidine-3-carboxylic acid (2-(1-(2-methoxyphenyl)piperidin-4-ylamino)ethyl)amide $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

Anal. Calcd for C$_{24}$H$_{28}$F$_2$N$_4$O$_4$.2.0 HCl, 1.65 H$_2$O, and 0.3 EtOAc: C=50.14, H=5.96, N=9.28. Found: C=50.12, H=5.81, N=9.27.

EXAMPLE 80

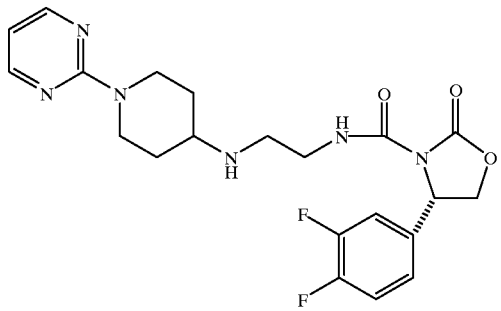

(4S)-4-(3,4-Difluorophenyl)-2-oxo-oxazolidine-3-carboxylic acid (2-(2-pyrimidinylpiperidin-4-ylamino)ethyl)amide $^1$H NMR (CDCl$_3$, 400 MHz) consistent with assigned structure.

HPLC (Vydac; C18; diameter=4.6 mm; length=150 mm; gradient=H$_2$O [0.1% H3PO$_4$]—CH$_3$CN, 95%–5%, 5%–95%, over 16 minutes, 2 ml/min flow rate) focus=215 nm; 98.4% pure.

Anal. Calcd for C$_{21}$H$_{24}$F$_2$N$_6$O$_3$.3.0 HCl and 0.45 EtOAc: C=45.98, H=5.18, N=14.11. Found: C=45.68, H=5.34, N=14.13.

EXAMPLE 81

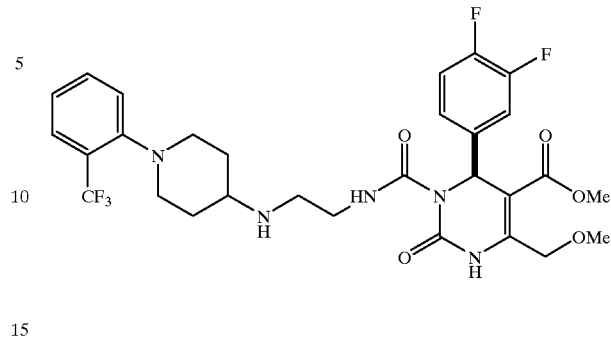

(4S)-4-(3,4-Difluorophenyl)-6-methoxymethyl-2-oxo-3-(2-(1-(2-trifluoromethylphenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 95.2% pure.

Anal. Calcd for C$_{29}$H$_{32}$F$_5$N$_5$O$_5$.1.0 HCl and 1.6 H$_2$O: C=50.41, H=5.28, N=10.14. Found: C=50.38, H=5.18, N=10.36.

EXAMPLE 82

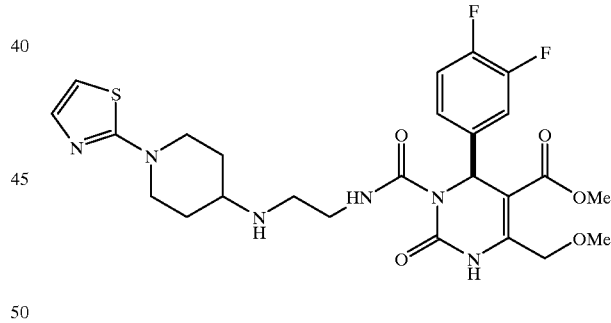

(4S)-4-(3,4-Difluorophenyl)-6-methoxymethyl-2-oxo-3-(2-(2-thiazolylpiperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_{41}$]—CH$_3$CN, 95%–5%, 5%–95%, over 16 minutes, 2 ml/min flow rate) focus=215 nm; 95.4% pure.

Anal. Calcd for C$_{25}$H$_{30}$F$_2$N$_6$O$_5$S.0.15 CH$_2$Cl$_2$ and 0.25 Et$_2$O: C=52.70, H=5.55, N=14.10. Found: C=52.71, H=5.53, N=13.97.

EXAMPLE 83

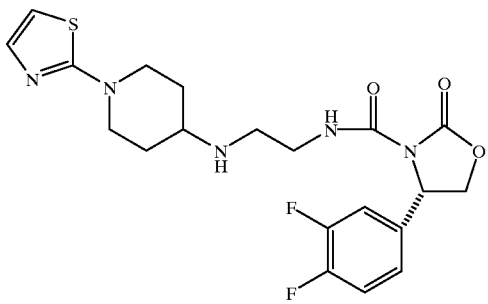

(4S)-4-(3,4-Difluorophenyl)-2-oxo-oxazolidine-3-carboxylic acid (2-(2-(thiazolyl)piperidin-4-ylamino)ethyl)amide $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 98.3% pure.

Anal. Calcd for C$_{20}$H$_{23}$F$_2$N$_5$O$_3$S.0.25 H$_2$O: C=52.68, H=5.19, N=15.36. Found: C=52.67, H=5.28, N=15.22.

EXAMPLE 84

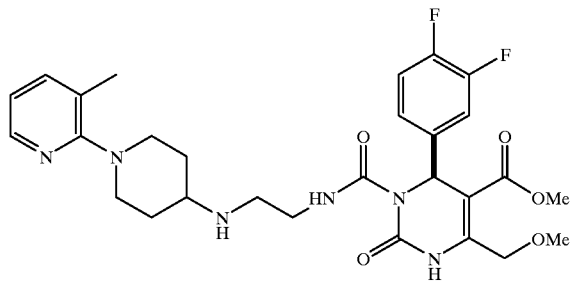

(4S)-4-(3,4-Difluorophenyl)-6-methoxymethyl-2-oxo-3-(2-(2-(3-methylpyridyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

Anal. Calcd for C$_{28}$H$_{34}$F$_2$N$_6$O$_5$.0.15 CH$_3$Cl: C=57.25, H=5.83, N=14.23. Found: C=57.06, H=5.68, N=14.22.

EXAMPLE 85

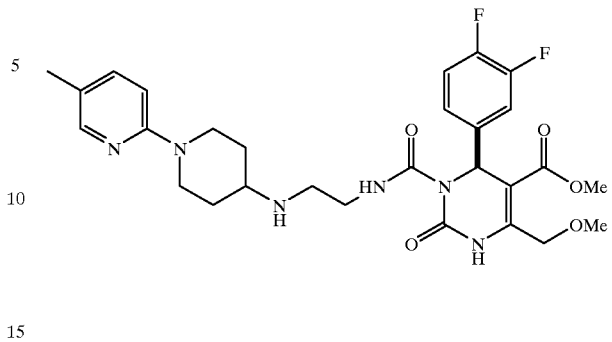

(4S)-4-(3,4-Difluorophenyl)-6-methoxymethyl-2-oxo-3-(2-(2-(5-methylpyridyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 97.3% pure.

Anal. Calcd for C$_{28}$H$_{34}$F$_2$N$_6$O$_5$.0.30 CH$_3$Cl: C=55.86, H=5.68, N=13.81. Found: C=55.71, H=5.56, N=14.15.

EXAMPLE 86

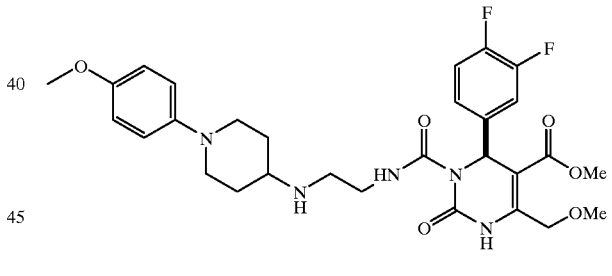

(4S)-4-(3,4-Difluorophenyl)-6-methoxymethyl-2-oxo-3-(2-(1-(4-methoxyphenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; >95% pure.

Anal. Calcd for C$_{29}$H$_{35}$F$_2$N$_5$O$_6$.2.0 HCl, 1.1 H$_2$O, and 0.55 Et$_2$O: C=51.96, H=6.25, N=9.71. Found: C=51.96, H=5.97, N=9.72.

EXAMPLE 87

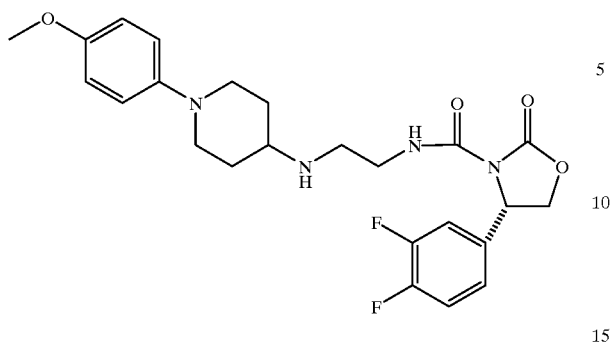

(4S)-4-(3,4-Difluorophenyl)-2-oxo-oxazolidine-3-carboxylic acid (2-(1-(4-methoxyphenyl)piperidin-4-ylamino)ethyl)amide $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; >95% pure.

Anal. Calcd for C$_{24}$H$_{28}$F$_2$N$_4$O$_4$.2.0 HCl, 1.7 H$_2$O, and 0.4 Et$_2$O: C=50.52, H=6.21, N=9.21. Found: C=50.54, H=5.82, N=9.12.

EXAMPLE 88

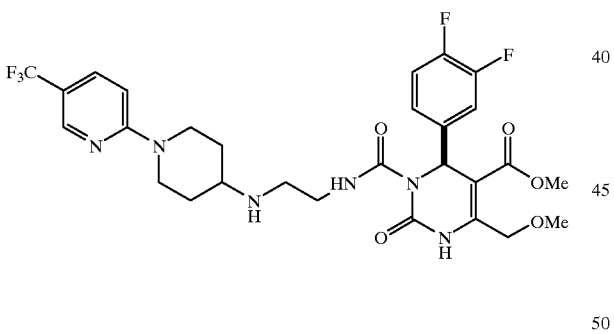

(4S)-4-(3,4-Difluorophenyl)-6-methoxymethyl-2-oxo-3-(2-(2-(5-trifluoromethylpyridyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 95.2% pure.

Anal. Calcd for C$_{24}$H$_{28}$F$_2$N$_4$O$_4$.1.45 TFA: C=46.86, H=4.13, N=10.61. Found: C=46.90, H=3.76, N=10.91.

EXAMPLE 89

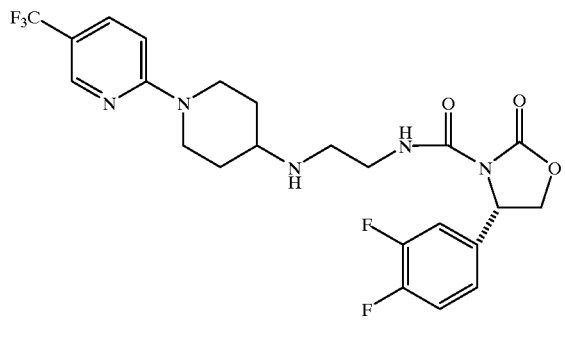

(4S)-4-(3,4-Difluorophenyl)-2-oxo-oxazolidine-3-carboxylic acid (2-(2-(5-trifluoromethylpyridyl)piperidin-4-ylamino)ethyl)amide $^1$H NM (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 96.8% pure.

Anal. Calcd for C$_{24}$H$_{28}$F$_2$N$_4$O$_4$.1.25 TFA and 0.95 H$_2$O: C=45.50, H=4.07, N=10.41. Found: C=45.34, H=3.72, N=10.80.

EXAMPLE 90

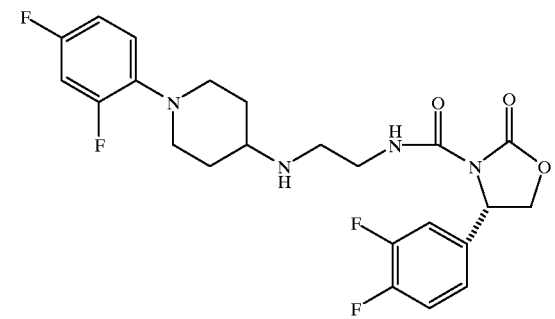

(4S)-4-(3,4-Difluorophenyl)-2-oxo-oxazolidine-3-carboxylic acid (2-(2-(2,4-difluorophenyl)piperidin-4-ylamino)ethyl)amide $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

Anal. Calcd for C$_{23}$H$_{24}$F$_4$N$_4$O$_3$.1.40 HCl: C=51.97, H=4.82, N=10.54. Found: C=52.02, H=4.90, N=10.71.

EXAMPLE 91

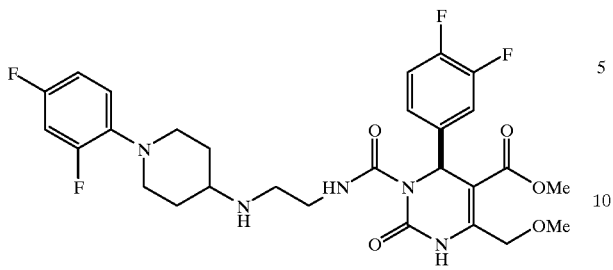

(4S)-4-(3,4-Difluorophenyl)-6-methoxymethyl-2-oxo-3-(2-(1-(2,4-difluorophenyl)piperidin-4ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

Anal. Calcd for C$_{28}$H$_{31}$F$_4$N$_5$O$_5$.1.30 HCl: C=52.46, H=5.08, N=10.93. Found: C=52.42, H=5.18, N=10.76.

EXAMPLE 92

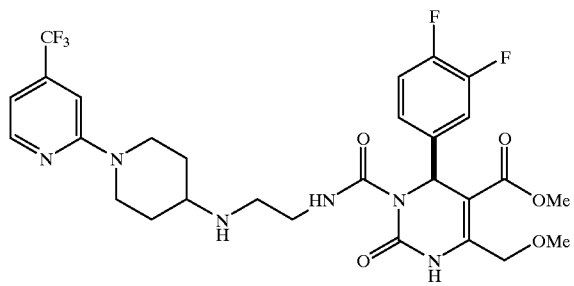

(4S)-4-(3,4-Difluorophenyl)-6-methoxymethyl-2-oxo-3-(2-(2-(4-trifluoromethylpyridyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 95.7% pure.

Anal. Calcd for C$_{28}$H$_{31}$F$_5$N$_6$O$_5$.0.15 CH$_2$Cl$_2$: C=52.88, H=4.93, N=13.15. Found: C=53.04, H=4.98, N=12.77.

EXAMPLE 93

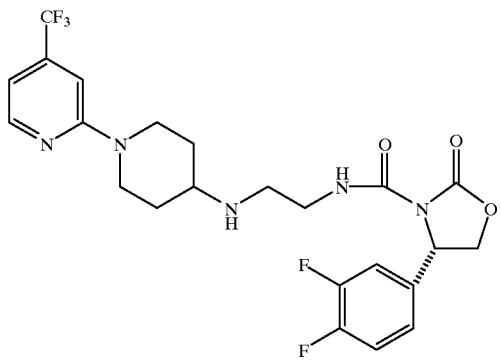

(4S)-4-(3,4-Difluorophenyl)-2-oxo-oxazolidine-3-carboxylic acid (2-(2-(4-trifluoromethylpyridyl)piperidin-4-ylamino)ethyl)amide $^1$H NMR (CDCl$_3$, 400 MHz) consistent with assigned structure.

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

FABLRMS m/e 514.08 g/mole (M$^+$+H, C$_{23}$H$_{24}$F$_5$N$_5$O$_3$= 513.46 g/mole.)

EXAMPLE 94

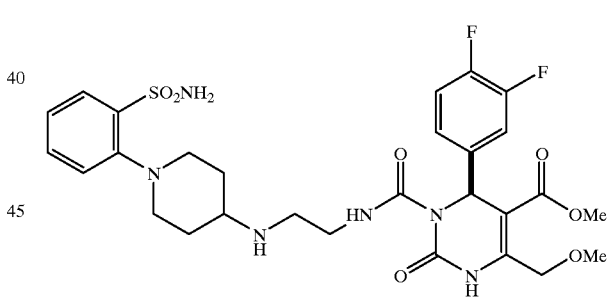

(4S)-4-(3,4-Difluorophenyl)-6-methoxymethyl-2-oxo-3-(2-(1-(2-sulfonamidophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 637 g/mole (M$^+$+H, C$_{28}$H$_{34}$F$_2$N$_6$O$_7$S= 636.676 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 98.8% pure.

EXAMPLE 95

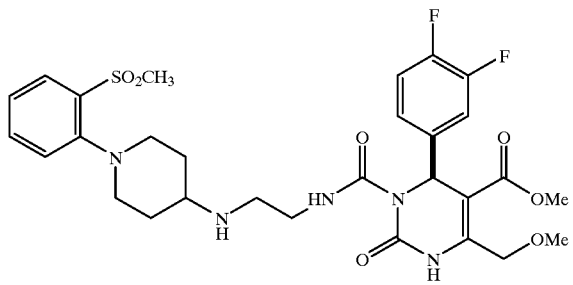

(4S)-4-(3,4-Difluorophenyl)-6-methoxymethyl-2-oxo-3-(2-(1-(2-methanesulfonylphenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 635 g/mole (M$^+$+H, C$_{29}$H$_{34}$F$_2$N$_5$O$_7$S= 634.68 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 96.1% pure.

Anal. Calcd for C$_{29}$H$_{34}$F$_2$N$_5$O$_7$S.0.95 HCl: C=51.69, H=5.30, N=10.39. Found: C=51.67, H=5.31, N=10.05.

EXAMPLE 96

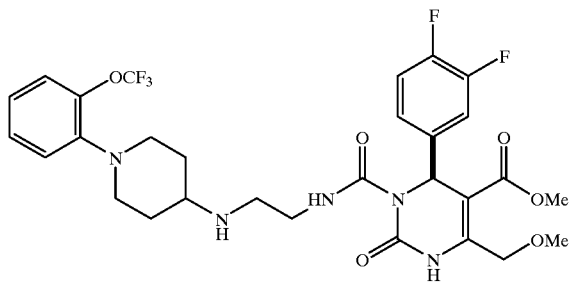

(4S)-4-(3,4-Difluorophenyl)-6-methoxymethyl-2-oxo-3-(2-(1-(2-trifluormethylphenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 642 g/mole (M$^+$+H, C$_{29}$H$_{32}$F$_5$N$_5$O$_6$= 641.596 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

EXAMPLE 97

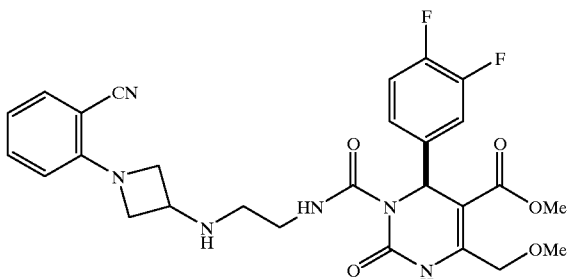

(4S)-4-(3,4-Difluorophenyl)-6-methoxymethyl-2-oxo-3-(2-(1-(2-cyanophenyl)azetidin-3-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 554 g/mole (M$^+$+H, C$_{27}$H$_{27}$F$_2$N$_6$O$_5$= 553.547 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 96% pure.

EXAMPLE 98

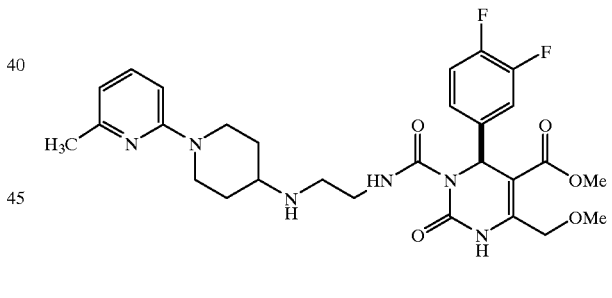

(4S)-4-(3,4-Difluorophenyl)-6-methoxymethyl-2-oxo-3-(2-(2-(6methylpyridinyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 573 g/mole (M$^+$+H, C$_{28}$H$_{34}$F$_2$N$_6$O$_5$= 572.62 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 95% pure.

EXAMPLE 99

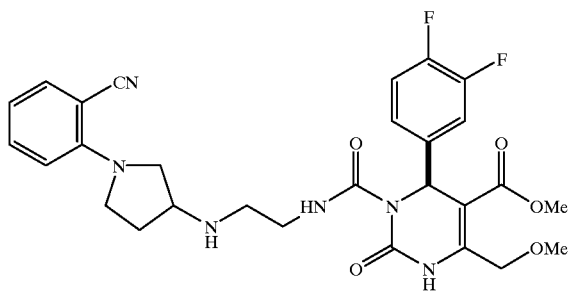

(4S)-4-(3,4-Difluorophenyl)-6-methoxymethyl-2-oxo-3-(2-(1-(2-cyanophenyl)pyrrolodin-3-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 569 g/mole (M$^+$+H, C$_{28}$H$_{30}$F$_2$N$_6$O$_5$= 568.582 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 98% pure.

EXAMPLE 100

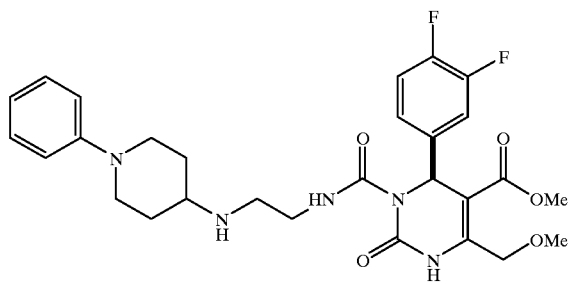

(4S)-4-(3,4-Difluorophenyl)-6-methoxymethyl-2-oxo-3-(2-(1-(phenyl)piperidin-4-ylamino)ethylcarbamoyl)-1,2,3,4-tetrahydropyrimidine-5-carboxylic add methyl ester $^1$H NMR (CDCl$_3$, 400 MHz) consistent with assigned structure.

FABLRMS m/e 558 g/mole (M$^+$+H, C$_{28}$H$_{33}$F$_2$N$_5$O$_5$= 557.599 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

EXAMPLE 101

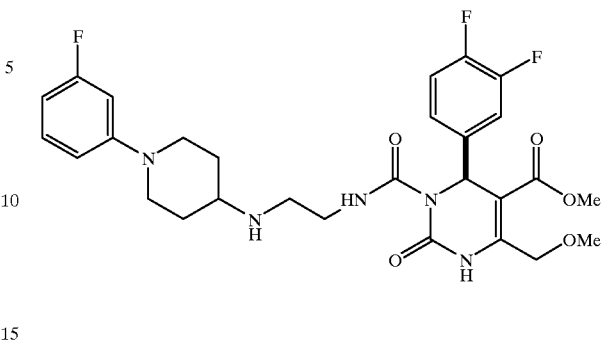

(4S)-4-(3,4-Difluorophenyl)-6-methoxyethyl-2-oxo-3-(2-(1-(3-fluorophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 576 g/mole (M$^+$+H, C$_{28}$H$_{32}$F$_3$N$_5$O$_5$= 575.589 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 98% pure.

EXAMPLE 102

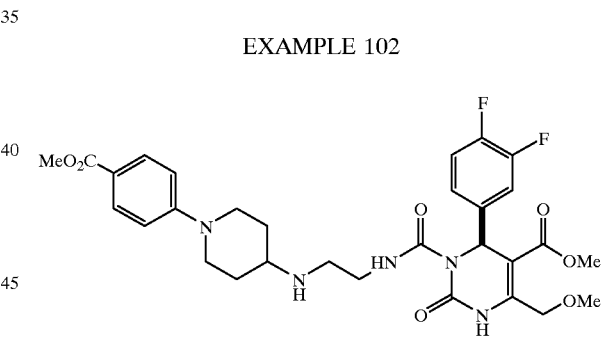

(4S)-4-(3,4-Difluorophenyl)-6-methoxymethyl-2-oxo-3-(2-(1-(4-carboxymethylphenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 616 g/mole (M$^+$+H, C$_{30}$H$_{35}$F$_2$N$_5$O$_7$= 615.635 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; >99% pure.

EXAMPLE 103

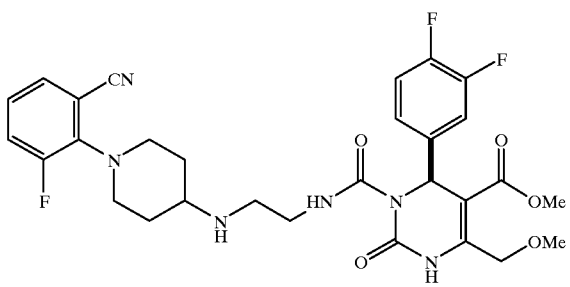

(4S)-4-(3,4-Difluorophenyl)-6-methoxymethyl-2-oxo-3-(2-(1-(2-cyano-6-fluorophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 601 g/mole (M$^+$+H, C$_{29}$H$_{31}$F$_3$N$_6$O$_5$=600.603 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 98.7% pure.

EXAMPLE 104

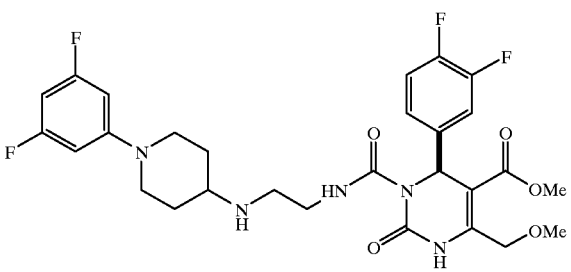

(4S)-4-(3,4-Difluorophenyl)-6-methoxymethyl-2-oxo-3-(2-(1-(3,5-difluorophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLEMS m/e 594 g/mole (M$^+$+H, C$_{28}$H$_{31}$F$_4$N$_5$O$_5$=593.583 g/mole.)

HPLC (Vydac; C18; diameter=4.6 mm; length=150 mm; gradient=H$_2$O [0.1% H3PO$_4$]—CH$_3$CN, 95%–5%, 5%–95%, over 16 minutes, 2 ml/min flow rate) focus=215 nm; 97.8% pure.

EXAMPLE 105

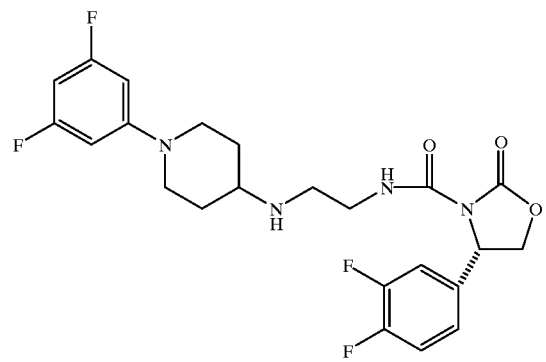

(4S)-4-(3,4-Difluorophenyl)-2-oxo-oxazolidine-3-carboxylic acid (2-(1-(3,5-difluorophenyl)piperidin-4-ylamino)ethyl)amide $^1$H NMR (CDCl$_3$, 400 MHz) consistent with assigned structure.

FABLRMS m/e 481 g/mole (M$^+$+H, C$_{23}$H$_{24}$F$_4$N$_4$O$_3$=480.463 g/mole.)

HPLC (Vydac; C18; diameter=4.6 mm; length 150 mm; gradient=H$_2$O [0.1% H$_3$PO$_4$]—CH$_3$CN, 95%–5%, 5%–95%, over 16 minutes, 2 ml/min flow rate) focus=215 nm; 97.1% pure.

EXAMPLE 106

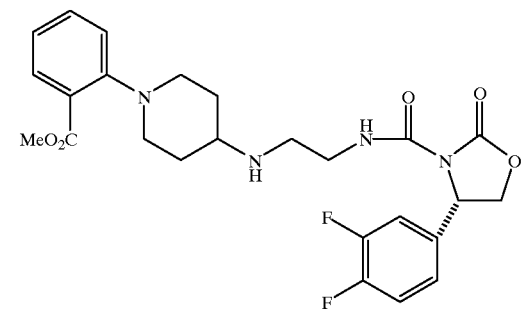

(4S)-4-(3,4-Difluorophenyl)-2-oxo-oxazolidine-3-carboxylic acid (2-(1-(2-carboyxmethylphenyl)piperidin-4-ylamino)ethyl)amide $^1$H NMR (CDCl$_3$, 400 MHz) consistent with assigned structure.

FABLRMS m/e 503 g/mole (M$^+$+H, C$_{25}$H$_{28}$F$_2$N$_4$O$_5$=502.523 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 99.5% pure.

EXAMPLE 107

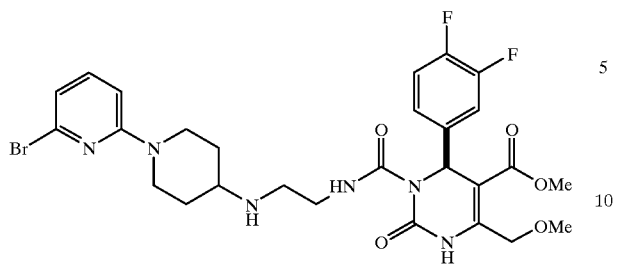

(4S)-4-(3,4-Difluorophenyl)-6-methoxymethyl-2-oxo-3-(2-(2-(6-bromopyridyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 637 g/mole (M$^+$+H, C$_{27}$H$_{31}$F$_2$N$_6$O$_5$= 637.486 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/mn flow rate) focus=215 nm; 99.4% pure.

EXAMPLE 108

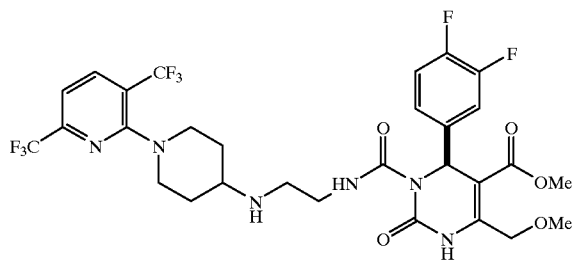

(4S)-4-(3,4-Difluorophenyl)-6-methoxymethyl-2-oxo-3-(2-(2-(3,6-bistrifluoromethylpyridyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 695 g/mole (M$^+$+H, C$_{29}$H$_{30}$F$_8$N$_6$O$_5$= 694.587 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 95.3% pure.

EXAMPLE 109

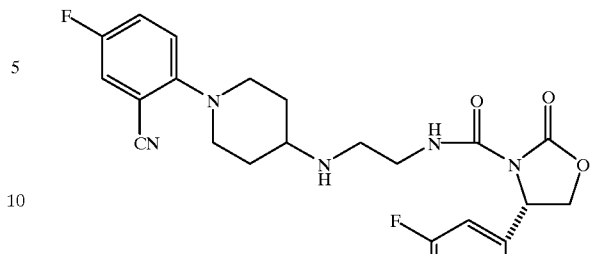

(4S)-4-(3,4-Difluorophenyl)-2-oxo-oxazolidine-3-carboxylic acid (2-(1-(2-cyano-4-fluorophenyl)piperidin-4-ylamino)ethyl)amide $^1$H NMR (CDCl$_3$, 400 MHz) consistent with assigned structure.

FABLRMS m/e 488 g/mole (M$^+$+H, C$_{24}$H$_{24}$F$_2$N$_5$O$_3$= 487.485 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 99.3% pure.

EXAMPLE 110

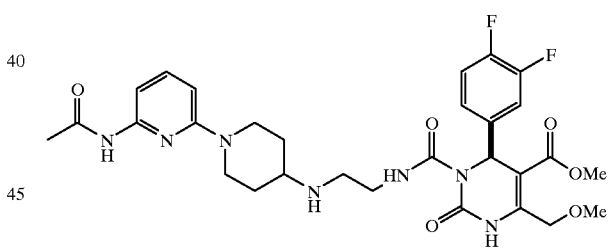

(4S)-4-(3,4-Difluorophenyl)-6-methoxymethyl-2-oxo-3-(2-(2-(6-N-acetylaminopyridyl)piperidine-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 615 g/mole (M$^+$+H, C$_{30}$H$_{36}$F$_2$N$_6$O$_6$= 614.65 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 99.2% pure.

EXAMPLE 111

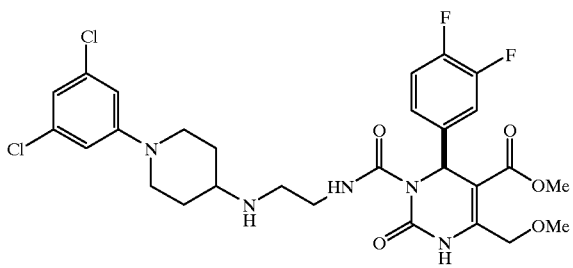

(4S)-4-(3,4-Difluorophenyl)-6-methoxymethyl-2-oxo-3-(2-(2-(3,5-dichlorophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABIRMS m/e 626 g/mole (M$^+$+H, C$_{28}$H$_{31}$Cl$_2$F$_2$N$_5$O$_5$= 626.489 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 96.4% pure.

EXAMPLE 112

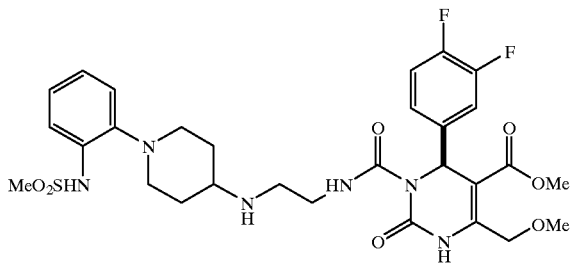

(4S)-4-(3,4-Difluorophenyl)-6-methoxymethyl-2-oxo-3-(2-(2-(2-N-methanesulfonylaminophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 651 g/mole (M$^+$+H, C$_{29}$H$_{36}$F$_2$N$_6$O$_7$S= 650.709 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

EXAMPLE 113

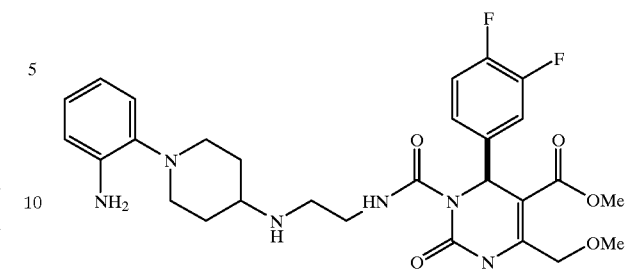

(4S)-4-(3,4-Difluorophenyl)-6-methoxymethyl-2-oxo-3-(2-(2-(2-aminophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 573 g/mole (M$^+$+H, C$_{28}$H$_{34}$F$_2$N$_6$O$_5$= 572.617 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

EXAMPLE 114

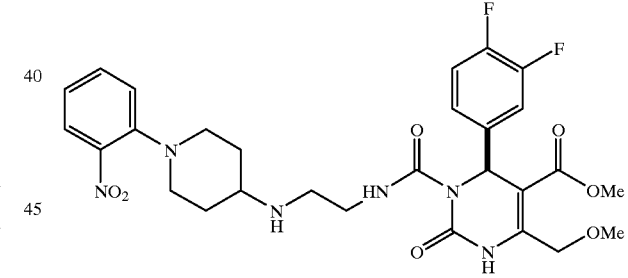

(4S)-4-(3,4-Difluorophenyl)-6-methoxymethyl-2-oxo-3-(2-(2-(2-nitrophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 617 g/mole (M$^+$+H, C$_{29}$H$_{34}$F$_2$N$_6$O$_7$= 616.629 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

EXAMPLE 115

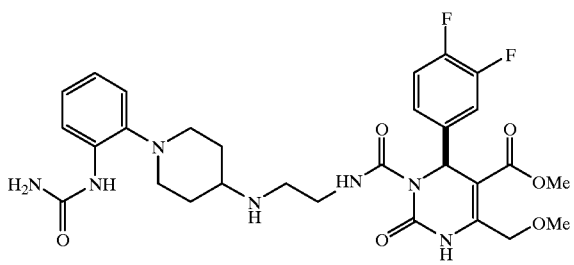

(4S)-4-(3,4-Difluorophenyl)-6-methoxymethyl-2-oxo-3-(2-(2-(2-N-carboxamidoaminophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 616 g/mole (M$^+$+H, C$_{29}$H$_{35}$F$_2$N$_7$O$_6$= 615.644 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 98.4% pure.

EXAMPLE 116

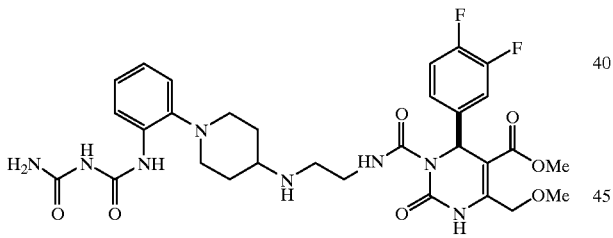

(4S)-4-(3,4-Difluorophenyl)-6-methoxymethyl-2-oxo-3-(2-(2-(2-N-1-imidocarbonic diamidyl)phenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 659 g/mole (M$^+$+H, C$_{30}$H$_{36}$F$_2$N$_8$O$_7$= 658.66 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 96.9% pure.

EXAMPLE 117

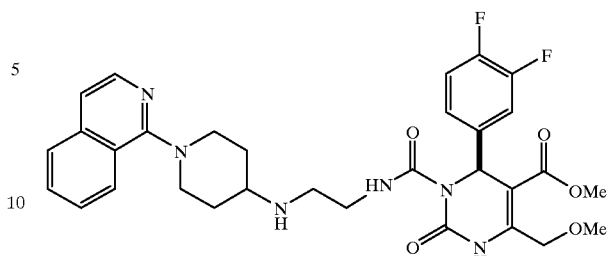

(4S)-4-(3,4-Difuorophenyl)-6-methoxymethyl-2-oxo-3-(2-(2-(1isoquinolinyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 609 g/mole (M$^+$+H, C$_{31}$H$_{34}$F$_2$N$_6$O$_5$= 608.651 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 95% pure.

EXAMPLE 118

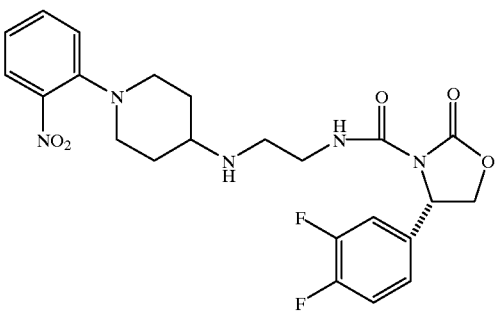

(4S)-4-(3,4-Difluorophenyl)-2-oxo-oxazolidine-3-carboxylic acid (2-(1-(2-nitrophenyl)piperidin-4-ylamino)ethyl)amide $^1$H NMR (CDCl$_3$, 400 MHz) consistent with assigned structure.

FABLRMS m/e 504 g/mole (M$^+$+H, C$_{24}$H$_{27}$F$_2$N$_5$O$_5$= 503.510 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 100% pure.

EXAMPLE 119

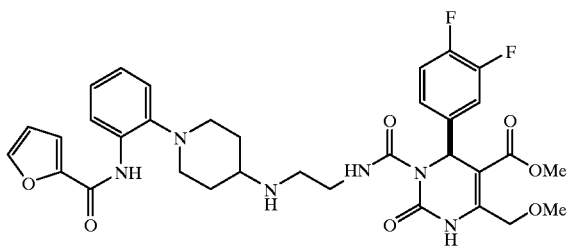

(4S)-4-(3,4-Difluorophenyl)-6-methoxymethyl-2-oxo-3-(2-(2-(2-N-(2-furanyl)carbonylaminophenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 667 g/mole (M$^+$+H, C$_{32}$H$_{36}$F$_2$N$_6$O$_7$= 608.651 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 99% pure.

EXAMPLE 120

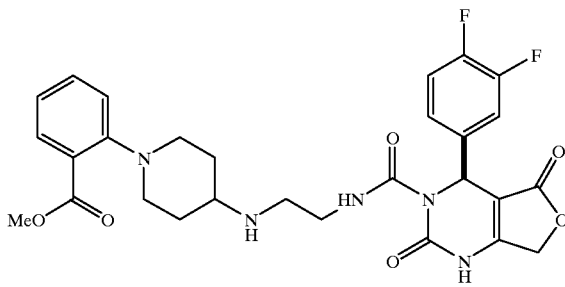

(4S)-4-(3,4-Difluorophenyl)-2-oxo-3-(2-(2-(2-arboxymethylphenyl)piperidin-4-ylamino)ethylcarbamoyl)-1,2,3,4-tetrahydro-4H-furo[3,4d]pyrimidine $^1$H NMR (CDCl$_3$, 400 MHz) consistent with assigned structure.

FABLRMS m/e 570 g/mole (M$^+$+H, C$_{28}$H$_{29}$F$_2$N$_5$O$_6$= 569.571 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nm; 97.9% pure.

EXAMPLE 121

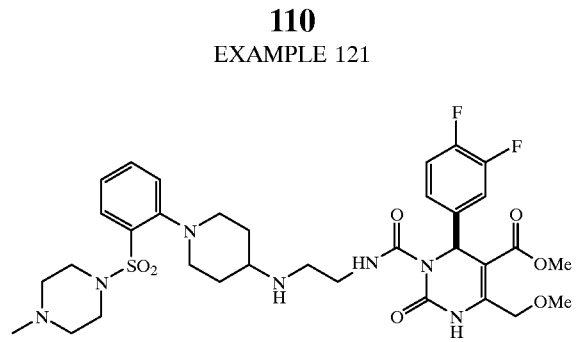

(4S)-4-(3,4-Difluorophenyl)-6-methoxymethyl-2-oxo-3-(2-(2-(4-N-methylpiperazinyl)sulfonylphenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 720 g/mole (M$^+$+H, C$_{33}$H$_{43}$F$_2$N$_7$O$_7$S= 719.816 g/mole.)

HPLC (Vydac; C18; diameter=4.6 mm; length=150 mm; gradient=H$_2$O [0.1% H$_3$PO$_4$]—CH$_3$CN, 95%–5%, 5%–95%, over 16 minutes, 2 ml/min flow rate) focus=215 nrm; 98.5% pure.

EXAMPLE 122

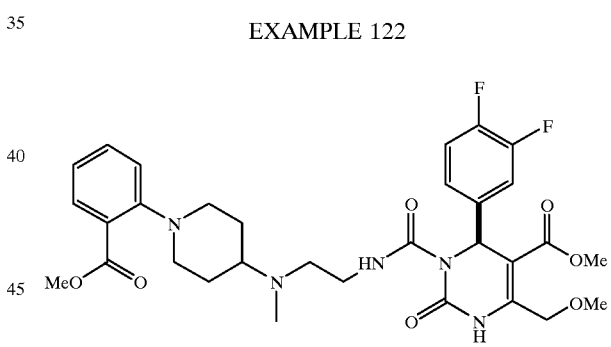

(4S)-4-(3,4-Difluorophenyl)-6-methoxymethyl-2-oxo-3-(2-(2-(2-carboxymethylphenyl)piperidin-4-yl-1-methylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 630 g/mole (M$^{30}$ +H, C$_{31}$H$_{37}$F$_2$N$_5$O$_7$= 629.662 g/mole.)

HPLC (Vydac; C18; diameter=4.6 mm; length=150 mm; gradient=H$_2$O [0.1% H$_3$PO4]—CH$_3$CN, 95%–5%, 5%–95%, over 16 minutes, 2 ml/min flow rate) focus=215 nm; 97.3% pure.

EXAMPLE 123

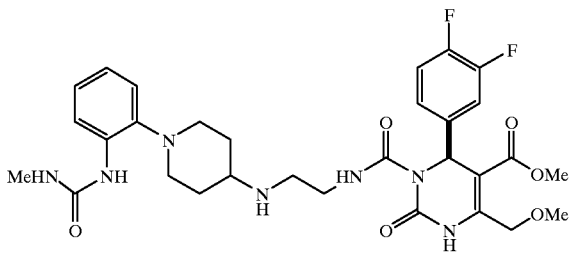

(4S)-4-(3,4-Difluorophenyl)-6-methoxymethyl-2-oxo-3-(2-(2-(1-N-(3-N-methylureyl)phenyl)piperidin-4-ylamino)ethylcarbamoyl)-1,2,3,4-tetrahydropyrimidine-5-carboxylic acid methyl ester $^1$H NMR (CDCl$_3$, 400 MHz) consistent with assigned structure.

FABLRMS m/e 630 g/mole (M$^+$+H, C$_{30}$H$_{37}$F$_2$N$_7$O$_6$= 629.669 g/mole.)

HPLC (Vydac; C18; diameter=4.6 mm; length=150 mm; gradient=H$_2$O [0.1% H$_3$PO4]—CH$_3$CN, 95%–5%, 5%–95%, over 16 minutes, 2 ml/min flow rate) focus=215 nm; 100% pure.

EXAMPLE 124

As a specific embodiment of an oral composition, 100 mg of the compound of Example 9 is formulated with sufficient finely divided lactose to provide a total amount of 580 to 590 mg to fill a size O hard gel capsule.

EXAMPLE 125

Screening Assay: Alpha 1a Adrenereic Receptor Binding

Membranes prepared from the stably transfected human alpha 1a cell line (ATCC CRL 11140) were used to identify compounds that bind to the human alpha 1a adrenergic receptor. These competition binding reactions (total volume=200 μl) contained 50 mM Tris-HCl pH. 7.4,5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values ≦50 nM.

EXAMPLE 126

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 μl) contained 50 mM Tris-HCl pH. 7.4, 5 mM EDTA, 150 at mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 127

Exemplary Counterscreens

1. Assay Title: Dopamine D2, D3, D4 in vitro Screen

The objective of this assay is to eliminate agents which specifically affect binding of [3H] spiperone to cells expressing human dopamine receptors D2, D3 or D4.

Method

Modified from VanTol et al (1991); Nature (Vol 350) Pg 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 μg membranes in a total volume of 500 μl containing 0.2 nM [3H]-spiperone. Non-specific binding is defined using 10 μM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a

The objective of this assay is to eliminate agents which specifically affect binding to cloned human 5HT1a receptor Method Modified from Schelegel and Peroutka Biochemical Pharmacology 35: 1943–1949 (1986).

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 μM propranolol. The assay is terminated after a 1 hour incubation at room temperature by rapid filtration over GF/Cfilters

EXAMPLE 128

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; CaCl$_2$, 2.5 mM; KH$_2$PO$_4$, 1.2 mM; MgSO$_4$, 1.2 mM; NaHCO$_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $C_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 $\mu$M (for rat), 10 $\mu$M (for dog) and 20 $\mu$M (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ ($-\log K_b$) values were obtained from Schild plot when three or more concentrations were tested. When less than three concentrations of antagonist are tested, $K_b$ values are calculated according to the following formula $K_b=[B]/x-1$, where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the so prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four parameter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula:

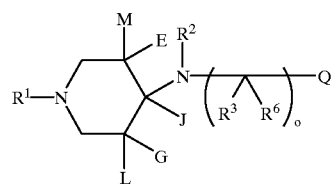

wherein

Q is

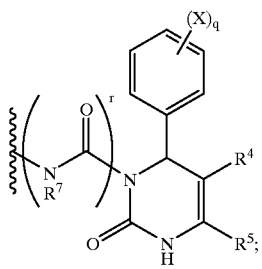

E, G, L and M are each independently selected from hydrogen, $C_{1-8}$ alkyl, $C_{3-8}$ cycloalkyl, $(CH_2)_{0-4}OR^{15}$, $(CH_2)_{0-4}N(R^{16})_2$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{16}$, or $(CH_2)_{0-4}SO_2N(R^{16})_2$;

J is selected from hydrogen, $C_{1-8}$ alkyl, $C_{3-8}$ cycloalkyl, $(CH_2)_{1-4}OR^{15}$, $(CH_2)_{1-4}N(R^{16})_2$, $(CH_2)_{1-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{16}$, or $(CH_2)_{0-4}SO_2N(R^{16})_2$;

$R^1$ is selected from unsubstituted, mono- or poly-substituted phenyl wherein the substituents on the phenyl are independently selected from halogen, $CF_3$, cyano, nitro, $N(R^{16})_2$, $NR^{16}COR^{18}$, $NR^{16}COR^{20}$, $NR^{16}CON(R^{18})_2$, $NR^{16}CONR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$ or $C_{1-4}$ alkyl; or unsubstituted, mono- or poly-substituted pyridyl, pyrazinyl, pyrimidinyl, thienyl, thiazolyl, furanyl, isoquinolinyl, quinazolinyl or naphthyl wherein the substituents on the pyridyl, pyrazinyl, pyrimidinyl, thienyl,thiazolyl, furanyl, isoquinolinyl, quinazolinyl or naphthyl are independently selected from $CF_3$, cyano, nitro, amino, $NR^{16}COR^{18}$, $NR^{16}COR^{20}$, $NR^{16}SO_2R^{18}$, $NR^{16}CONR^{16}CON(R^{18})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$, phenyl $OR^{15}$, halogen, $C_{1-4}$ alkyl or $C_{3-8}$ cycloalkyl;

$R^2$ and $R^7$ are each independently selected from hydrogen, $C_{1-8}$ alkyl, $C_{4-8}$ cycloalkyl, $(CH_2)_{0-4}CO_2R^{16}$, $(CH_2)_{0-4}CON(R^{16})_2$, $(CH_2)_{0-4}COR^{16}$, $(CH_2)_{2-4}OR^{15}$, $(CH_2)_{1-4}CF_3$, $(CH_2)_{0-4}SO_2R^{16}$, $(CH_2)_{0-4}SO_2N(R^{16})_2$ or $(CH_2)_{1-4}CN$;

$R^3$ and $R^6$ are each independently selected from hydrogen, $C_{1-8}$ alkyl, $C_{3-8}$ cycloalkyl, $(CH_2)_{2-4}OR^{15}$ or $(CH_2)_{0-4}CF_3$;

$R^4$ is selected from hydrogen, $(CH_2)_{0-4}COR^{15}$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{15}$ or $(CH_2)_{0-4}SO_2N(R^{16})_2$;

$R^5$ is selected from hydrogen, $C_{1-8}$ alkyl, $C_{3-8}$ cycloalkyl, $(CH_2)_{1-4}OR^{15}$ or $(CH_2)_{0-4}CF_3$;

$R^{15}$ is selected from hydrogen, $C_{1-8}$ alkyl, $C_{3-8}$ cycloalkyl or $(CH_2)_{0-4}CF_3$;

$R^{16}$ and $R^{18}$ are each independently selected from hydrogen, $C_{1-8}$ alkyl, $C_{4-8}$ cycloalkyl or $(CH_2)_{1-4}CF_3$;

$R^{20}$ is furanyl or $C_{1-8}$ alkyl furanyl;

$R^{22}$ is piperazinyl or $C_{1-8}$ alkylpiperazinyl;

each X is independently selected from halogen, cyano, nitro, $C_{1-8}$ alkyl, $C_{3-8}$ cycloalkyl, $(CH_2)_{0-4}OR^{15}$ or $(CH_2)_{0-4}CF_3$;

q is an integer from zero to four;

o is an integer from two to five; and r is an integer from zero to one;

or a pharmaceutically acceptable salt thereof.

2. The compound of claim 1, wherein $R^1$ is selected from unsubstituted, mono- or poly-substituted phenyl wherein the substituents on the phenyl are independently selected from halogen, $CF_3$, cyano, nitro, $N(R^{16})_2$, $NR^{16}COR^{18}$, $NR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$ or $C_{1-4}$ alkyl; or unsubstituted, mono- or poly-substituted pyridyl, pyrazinyl, thienyl, thiazolyl, furanyl, quinazolinyl or naphthyl wherein the substituents on the pyridyl, pyrazinyl, thienyl, furanyl, quinazolinyl or naphthyl are independently selected from $CF_3$, cyano, nitro, amino, $NR^{16}COR^{18}$, $NR^{16}SO_2R^{18}$, $(CH_2)_{0-4}CO_2R_{16}$, $(CH_2)_{0-4}CON(R^{16})_2$, $(CH_2)_{0-4}SO_2N(R^{16})_2$, $(CH_2)_{0-4}SO_2R^{15}$, phenyl, $OR^{15}$, halogen, $C_{1-4}$ alkyl or $C_{3-8}$ cycloalkyl; and $R^4$ is selected from $(CH_2)_{0-4}COR^{15}$, $(CH_2)_{0-4}CN$, $(CH_2)_{0-4}CF_3$, $(CH_2)_{0-4}CO_2R^{16}$, $(CH_2)_{0-4}CON(R^{16})_2$, $(CH_2)_{0-4}SO_2R^{15}$ or $(CH_2)_{0-4}SO_2N(R^{16})_2$;

or a pharmaceutically acceptable salt thereof.

3. The compound of claim 1, of the formula

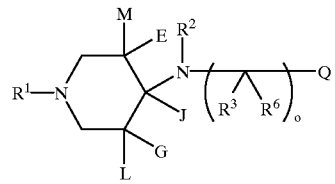

wherein

E, G, L, M and J are each independently selected from hydrogen, $C_{1-8}$ alkyl, $C_{3-8}$ cycloalkyl, or $(CH_2)_{0-4}CF_3$;

$R^1$ is selected from unsubstituted, mono-, di- or tri-substituted phenyl wherein the substituents on the phenyl are independently selected from halogen, $CF_3$, cyano, nitro, $N(R^{16})_2$, $NR^{16}COR^{18}$, $NR^{16}COR^{20}$, $NR^{16}CON(R^{18})_2$, $NR^{16}CONR^{16}CON(R^{18})_2$, $NR^{16}SO_2R^{18}$, $NR^{16}SO_2N(R^{18})_2$, $OR^{15}$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$ or $C_{1-4}$ alkyl; or unsubstituted, mono-, di- or tri-substituted pyridyl, pyrazinyl, pyrimidinyl, thienyl, thiazolyl, furanyl, isoquinolinyl, quinazolinyl or naphthyl wherein the substituents on the pyridyl, pyrazinyl, pyrimidinyl, thienyl, thiazolyl, furanyl, isoquinolinyl, quinazolinyl or naphthyl are independently selected from $CF_3$, cyano, nitro, amino, $NR^{16}COR^{18}$, $NR^{16}COR^{20}$, $NR^{16}SO_2R^{18}$, $NR^{16}CONR^{16}CON(R^{18})_2$, $(CH_2)_{0-4}CO_2R^{16}$, $(CH_2)_{0-4}CON(R^{16})_2$, $(CH_2)_{0-4}SO_2N(R^{16})_2$, $(CH_2)_{0-4}SO_2R^{15}$, $(CH_2)_{0-4}SO_2R^{22}$, phenyl, $OR^{15}$, halogen, $C_{1-4}$ alkyl or $C_{3-8}$ cycloalkyl;

$R^2$ and $R^7$ are each independently selected from hydrogen, $C_{1-8}$ alkyl, $C_{4-8}$ cycloalkyl or $(CH_2)_{1-4}CF_3$; and o is an integer from two to four;

or a pharmaceutically acceptable salt thereof.

4. The compound of claim 3, of the formula

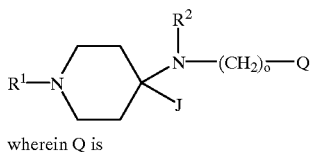

wherein Q is

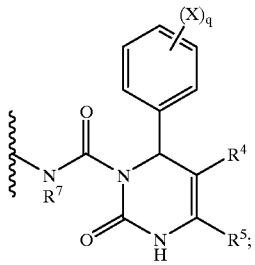

R¹ is selected from unsubstituted, mono-, di- or trisubstituted phenyl wherein the substituents on the phenyl are independently selected from halogen, $CF_3$, cyano, nitro, $N(R^{16})_2$, $NR^{16}COR^{18}$, $NR^{16}COR^{20}$, $NR^{16}CON(R^{18})_2$, $NR^{16}SO_2R^{18}$, $OR^{15}$, $(CH_2)_{0-2}CO_2R^{16}$, $(CH_2)_{0-2}CON(R^{16})_2$, $(CH_2)_{0-2}SO_2R^{15}$, $(CH_2)_{0-2}SO_2N(R^{16})_2$, $(CH_2)_{0-2}SO_2R^{22}$ or $C_{1-4}$ alkyl; or unsubstituted, mono- or di-substituted pyridyl or pyrimidinyl wherein the substituents on the pyridyl or the pyrimidinyl are independently selected from $CF_3$, cyano, nitro, amino, $NR^{16}COR^{18}$, $NR^{16}COR^{20}$, $NR^{16}CON(R^{18})_2$, $NR^{16}SO_2R^{18}$, $(CH_2)_{0-2}CO_2R^{16}$, $(CH_2)_{0-2}CON(R^{16})_2$, $(CH_2)_{0-2}SO_2R^{15}$, $(CH_2)_{0-2}SO_2N(R^{16})_2$, $OR^{15}$, halogen, $(CH_2)_{0-2}SO_2R^{22}$ or $C_{1-4}$ alkyl; or unsubstituted thiazolyl; or unsubstituted isoquinolinyl;

$R^2$ and $R^7$ are each independently selected from hydrogen, $C_{1-6}$ alkyl, $C_{4-6}$ cycloalkyl or $(CH_2)_{1-4}CF_3$;

$R^4$ is selected from hydrogen, $COR^{15}$, $(CH_2)_{0-2}CO_2R^{16}$, $SO_2R^{15}$ or $(CH_2)_{0-2}CON(R^{16})_2$;

$R^5$ is selected from hydrogen, $C_{1-6}$ alkyl, $C_{3-6}$ cycloalkyl, $(CH_2)_{1-3}OR^{15}$ or $(CH_2)_{0-3}CF_3$;

$R^{15}$ is selected from hydrogen, $C_{1-6}$ alkyl, $C_{3-6}$ cycloalkyl or $(CH_2)_{0-2}CF_3$;

$R^{16}$ and $R^{18}$ are each independently selected from hydrogen, $C_{1-6}$ alkyl, $C_{4-6}$ cycloalkyl or $(CH_2)_{1-2}CF_3$;

o is an integer from two to four, p is an integer from one to two; and q is an integer from zero to three;

or a pharmaceutically acceptable salt thereof.

5. The compound of claim 4, selected from the group consisting of 4S-4-(3,4-difluorophenyl)-6-methoxymethyl-2-oxo-3-(2-(2-(4-trifluoromethylpyrmdinyl)-piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-pyrimidinylpiperidin-4-ylamino)ethylcarbamoyl)-1,2, 3,4-tetrahydropyrimidine-5-carboxylic acid methyl ester;

4S-4-(3,4-difluorophenyl)-6-methoxymethyl-2-oxo-3-(2-(2-pyrimidinylpiperidin-4-ylamino)ethylcarbamoyl)-1,2, 3,4-tetrahydropyrimidine-5-carboxylic acid methyl ester;

4S-4-(3,4-difluorophenyl)-6-methoxymethyl-2-oxo-3-(2-(2-thiazolylpiperidin-4-ylamino)ethylcarbamoyl)-1,2,3, 4-tetrahydropyrimidine-5-carboxylic acid methyl ester;

4S-4-(3,4-difluorophenyl)-6-methoxymethyl-2-oxo-3-(2-(2-(1-isoquinolinyl)piperidin-4-ylamino) ethylcarbamoyl)-1,2,3,4,-tetrahydropyrimidine-5-carboxylic acid methyl ester;

and the pharmaceutically acceptable salts thereof.

6. The compound of claim 4, of the formula

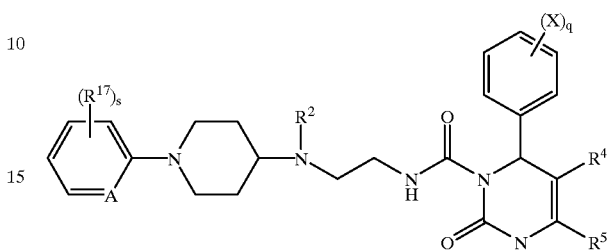

wherein

A is C—R⁷ or N;

$R^2$ is selected from hydrogen or $CH_2CF_3$;

each $R^{17}$ is independently selected from hydrogen, halogen, $CF_3$, cyano, nitro, amino, $NR^{16}COR^{18}$, $NR^{16}CON(R^{18})_2$, $NR^{16}CONR^{16}CON(R^{18})_2$, $NR^{16}SO_2R^{18}$, $NR^{16}COR^{20}$, $OR^{15}$, $CO_2R^{16}$, $CON(R^{16})_2$, $SO_2N(R^{16})_2$, $SO_2R^{15}$ or $C_{1-4}$ alkyl;

each X is halogen; and q and s are each independently an integer from zero to two;

or a pharmaceutically acceptable salt thereof.

7. The compound of claim 6, of the formula

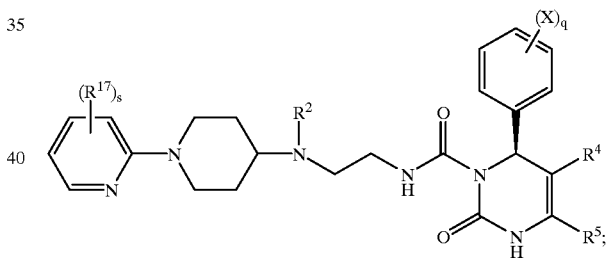

or a pharmaceutically acceptable salt thereof.

8. The compound of claim 7, selected from the group consisting of 4S-4-(3,4-difluorophenyl)-6-methoxymethyl-2-oxo-3-(2-(2-(3-trifluoromethylpyridyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(3-methylpyridyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(5-methylpyridyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(5-trifluoromethylpyridyl)piperidin-4-ylamino) ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(4-trifluoromethylpyridyl)piperidin-4-ylamino)

ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(6-methylpyridinyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(6-bromopyridyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(3,6-bistrifluoromethylpyridyl)-piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(6-N-acetylaminopyridyl)piperidin-4-ylamino)ethylcarbamoyl)-1,2,3,4-tetrahydropyrimidine-5-carboxylic acid methyl ester;

and the pharmaceutically acceptable salts thereof.

9. The compound of claim 6, of the formula

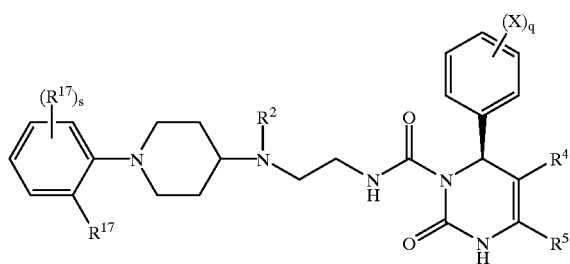

wherein each $R^{17}$ is independently selected from hydrogen, halogen, $CF_3$, cyano, nitro, amino, $NHCONH_2$, $NHCONHCONH_2$, NHCO-furanyl, NHCONH $C_{1-4}$ alkyl, $C_{1-4}$ alkoxy, $OCF_3$, $OCH_2CF_3$, $CO_2$—$C_{1-4}$ alkyl, $CONH_2$, $SO_2NH_2$, $SO_2C_{1-4}$ alkyl, $NHSO_2C_{1-4}$ alkyl, or $C_{1-4}$ alkyl;

or a pharmaceutically acceptable salt thereof.

10. The compound of claim 9, selected from 4-(3,4-difluorophenyl)-6-methoxymethyl-3-(2-(1-(2-nitrophenyl)-piperidin-4-ylamino)ethylcarbamoyl)-2-oxo-1,2,3,4-tetrahydropyrimidine-5-carboxylic acid methyl ester;

3-(2-(1-(2-cyanophenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;

4-(3,4-difluorophenyl)-6-methoxymethyl-2-oxo-3-(2-(1-o-tolylpiperidin-4-ylamino)ethylcarbamoyl)-1,2,3,4-tetrahydropyrimidine-5-carboxylic acid methyl ester;

4-(3,4-difluorophenyl)-6-methoxymethyl-3-(2-(1-(2-methoxyphenyl)piperidin-4-ylamino) ethylcarbamoyl)-2-oxo-1,2,3,4-etrahydropyrimidine-5-carboxyic acid methyl ester;

3-(2-(1-(2cyano-4-trifluoromethylphenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;

3-(2-(1-(2-cyano-4-methylphenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;

3-(2-(1-(4-cyanophenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;

3-(2-(1-(2-cyano-4-fluorophenyl)-piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;

4-(3,4-difluorophenyl)-3-(2-(1-(2-ethoxycarbonylphenyl)piperidin-4-ylamino)ethylcarbamoyl)-6-methoxymethyl-2-oxo-1,2,3,4-tetrahydropyrimidine-5-carboxylic acid methyl ester;

4-(3,4-difluorophenyl)-6-methoxymethyl-2-oxo-3-(2-(1-(2-(2,2,2-trifluoroethoxy)phenyl)piperidin-4-ylamino)ethylcarbamoyl)-1,2,3,4-tetrahydropyrimidine-5-carboxylic acid methyl ester;

3-(2-(1-(2-carbamoylphenyl)piperidin-4-ylamino)ethylcarbamoyl)-4-(3,4-difluorophenyl)-6-methoxymethyl-2-oxo-1,2,3,4-tetrahydropyrimidine-5-carboxylic acid methyl ester;

and the pharmaceutically acceptable salts thereof.

11. The compound of claim 9, selected from the group consisting of 4S-4-(3,4-difluorophenyl)-6-methoxymethyl-2-oxo-3-(2-(1-(2-trifluoromethylphenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(4-methoxyphenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2,4-difluorophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-sulfonamidophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-methanesulfonylphenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-trifluoromethylphenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(phenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(3-fluorophenyl)piperidin-4-ylamino)ethylcarbamoyl)-1,2,3,4-tetrahydropyrirnidine-5-carboxylic acid methyl ester;

4S-4-(3,4-difluorophenyl)-6-methoxymethyl-2-oxo-3-(2-(1-(4-carboxylmethylphenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(2-cyano-5-fluorophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(1-(3,5-difluorophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(3,6-bistrifluoromethylpyridyl)-piperidin-4-ylamino)

ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(3,5-dichlorophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-N-sulfonylmethylaminophenyl)-piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-aminophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-nitrophenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-N-carboxamidoaminophenyl)-piperidin-4-ylamino)ethylcarbamoyl)-1,2,3,4-tetrahydropyrimidine-5-carboxylic acid methyl ester;

4S-4-(3,4-Difluorophenyl)-6-methoxymethyl-2-oxo-3-(2-(2-(2-N-1-imidocarbonic diamidyl)phenyl)piperidin-4-ylamino)ethylcarbamoyl)-1,2,3,4-tetrahydropyrimidine-5-carboxylic acid methyl ester 4S-4-(3,4-difluorophenyl)-6-methoxymethyl-2-oxo-3-(2-(2-(2-N-(2-furanyl)carbonylamino-phenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(4-N-methylpiperazinyl)-sulfonylphenyl)piperidin-4-ylamino)ethylcarbamoyl)-1,2,3,4-tetrahydropyrimidine-5-carboxylic acid methyl ester;

4S-4-(3,4-difluorophenyl)-6-methoxymethyl-2-oxo-3-(2-(2-(2-carboxymethylphenyl)piperidin-4-yl-1-methylamino)ethylcarbamoyl)-1,2,3,4-tetrahydropyrimidine-5-carboxylic acid methyl ester;

(4S)-4-(3,4-Difluorophenyl)-6-methoxymethyl-2-oxo-3-(2-(2-(1-N-(3-N-methylureyl)phenyl)piperidin-4-ylamino)ethylcarbamoyl)-1,2,3,4-tetrahydropyrimidine-5-carboxylic acid methyl ester;

and the pharmaceutically acceptable salts thereof.

12. A pharmaceutical composition comprising the compound of claim 1 and a pharmaceutically acceptable carrier.

13. A method of treating benign prostatic hyperplasia in a subject in need thereof which comprises administering to the subject a therapeutically effective amount of the compound of claim 1.

14. The method of claim 13, wherein the compound additionally does not cause a fall in blood pressure at dosages effective to alleviate benign prostatic hyperplasia.

15. A method of treating benign prostatic hyperplasia in a subject in need thereof which comprises administering a therapeutically effective amount of the composition of claim 12.

16. A method of relaxing lower urinary tract tissue in a subject in need thereof which comprises administering to the subject a therapeutically effective amount of the compound of claim 1.

17. The method of claim 13, wherein the compound additionally does not cause a fall in blood pressure at dosages effective to relax lower urinary tract tissue.

* * * * *